US006004794A

United States Patent [19]
Karran et al.

[11] Patent Number: 6,004,794
[45] Date of Patent: Dec. 21, 1999

[54] HUMAN SERINE PROTEASE

[75] Inventors: Eric Howard Karran, Bishop's Stortford; Helen Elizabeth Clinkenbeard, Hertford; Michael Joseph Browne, Welwyn Garden City; Christopher David Southan, London, all of United Kingdom; Caretha Lee Creasy, Erdenheim; George Pietro Livi, Havertown, both of Pa.

[73] Assignees: SmithKline Beecham Corporation; SmithKline Beecham p.l.c., both of Philadelphia, Pa.

[21] Appl. No.: 08/923,454

[22] Filed: Sep. 4, 1997

Related U.S. Application Data

[60] Provisional application No. 60/032,875, Dec. 13, 1996, provisional application No. 60/027,873, Oct. 25, 1996, and provisional application No. 60/025,436, Sep. 6, 1996.

[51] Int. Cl.$^6$ .............................. C12N 9/64; C12N 15/57; C12N 15/70; C12N 15/85
[52] U.S. Cl. ...................... 435/226; 435/69.1; 435/252.3; 435/320.1; 536/23.2; 536/23.5
[58] Field of Search ................................ 435/69.1, 252.3, 435/320.1, 226; 536/23.2, 23.5

[56] References Cited

FOREIGN PATENT DOCUMENTS

WO 98/01549   1/1998   WIPO .

OTHER PUBLICATIONS

Sherrington et al., "Cloning of a Gene Bearing Missense Mutations in Early–Onset Familial Alzheimer's Disease", *Nature*, vol. 375, pp. 754–760 (1995).

Rogaev et al., "Familial Alzheimer's Disease in Kindreds with Missense Mutations in a Gene on Chromosome 1 Related to the Alzheimer's Disease Type 3 Gene", *Nature*, vol. 376, pp. 775–778 (1995).

Levy–Lahad et al., "Candidate Gene for the Chromosome 1 Familial Alzheimer's Disease Locus", *Science*, vol. 269, pp. 973–977 (1995).

Mercken et al., "Characterization of Human Presenilin 1 Using N–terminal Specific Monoclonal Antibodies: Evidence that Alzheimer Mutations Affect Proteolytic Processing", *FEBS Letters*, vol. 389, pp. 297–303 (1996).

Lipinska, "Sequence Analysis and Regulation of the htrA Gene of *Escherichia coli*: a $6^{32}$–Independent Mechanism of Heat–inducible Transcription", *Nucleic Acids Research*, vol. 16, pp. 10053–10067 (1988).

Ohno, et al., Genbank Accession No. D87258 (1996).

Zumbrunn, J., et al., FEBS Letters, vol. 398, "Primary structure of a putative serine protease specific for IGF–binding proteins", pp. 187–192, 1996.

*Primary Examiner*—Ponnathapura Achutamurthy
*Assistant Examiner*—William W. Moore
*Attorney, Agent, or Firm*—Kirk Baumeister; William T. King

[57] ABSTRACT

Isolated nucleic acids encoding a human serine protease PSP1, protein obtainable from the nucleic acids, recombinant host cells transformed with the nucleic acids, oligonucleotides and primer pairs specific for PSP1 polymorphisms and use of the protein and nucleic acid sequences are disclosed.

14 Claims, 11 Drawing Sheets

```
 41 SGTSDPRARVTYGTPSLWARLSVGVTEPPRACLTSGTPGPRAQLTAVTPDT  90
    .|.  .|::..  :...||..|....  ...  ..
  2 KKTTLALSRLALSLGLALSPLSATAAETSSATTAQQMPSLAPMLEKVMPS   51

91 RTREASENSGTRSRAWLAVALGAGGAVLLLLWGGCRGPPAVLAAVPSPPP  140
    ...  .|.|.  .:::.  ::|:  ...:.  .||  .
 52 VVSINVEGSTTVNTPRMPRNFQQ.......FFGDD....SPFCQEGSPFQ   90

141 ASPRSQYNFIADVVEKTAPAVVYIEILDRHPFLGREVPISNGSGFVVAAD  190
    .||  :|   :::.:  :...  ::::         |||.:::||
 91 SSPFCQ...GGQGGNGGGQQQKFMAL..............GSGVIIDAD  122

191 .GLIVTNAHVVADRRRVRVRLLSGDTYEAVVTAVDPVADIATLRIQTKEP  239
    |.:|||.|||.:   ::|.|  .|  .::|  ::  ||  .|||  :.||..
123 KGYVVTNNEVVDNATVIKVQLSDGRKFDAKMVGKDPRSDIALIQIQNPKN  172

240 LPTLPLGRSADVRQGEFVVAMGSPFALQNTITSGIVSSAQRPARDLGLPQ  289
    |...::  |...|  |::.|::.|.||:.|:||||||..|.   ||..
173 LTAIKMADSDALRVGDYTVGIGNPFGLGETVTSGIVSALGRS....GLNA  218

290 TNVE.YIQTDAAIDFGNSGGPLVNLDGEVIGVNTMKVTA.....GISFAI  333
    .|  |  :|||||||:  |||||:|||||:|:|:||    :.:      ||:|||
219 ENYENFIQTDAAINRGNSGGALVNLNGELIGINTAILAPDGGNIGIGFAI  268

334 PSDRLREF.........LHRGE............................  346
    ||:..:::             :.|||
269 PSNMVKNLTSQMVEYGQVKRGELGIMGTELNSELAKAMKVDAQRGAFVSQ  318

347 .KKNSSSGISG..................SQRRYIGVM....MLTL...  369
    .|||.:  .|           .|  .  :|.|     .|||
319 VLPNSSAAKAGIKAGDVITSLNGKPISSFAALRAQVGTMPVGSKLTLGLL  368

370 .....................SPSILAELQLREPSFPDVQHGVLIHKVIL  398
                  .|.||:.::.  |  |.:  ::||:::|.|
369 RDGKQVNVNLELQQSSQNQVDSSSIPNGIEGAEMSNKGKDQGVVVNNVKT  418

399 GSPAHRAGLRPGDVILAIGEQMVQNAEDVYEAVRTQ.SQLAVQIRRGRET  447
    |.||  .  ||:.|||||::  .:|  |.|.  ...  ...  .  ||  :.|.||
419 GTPAAQIGLKKGDVIIGANQQAVKNIAELRKVLDSKPSVLALNIQRGDRH  468

448 LTLYVTPEVTE  458
    |.:  ...  .::.
469 LPVNAVISLNP  479
```

```
 41 SGTSDPRARVTYGTPSLWARLSVGVTEPRACLTSGTPGPRAQLTAVTPDT  90
    . |. : .|:..:  .  :..||....|....|.. .. |.:. . ..
  2 KKTTLALSRLALSLGLALSPLSATAAETSSATTAQQMPSLAPMLEKVMPS  51

91 RTREASENSGTRSRAWLAVALGAGGAVLLLLWGGGRGPPAVLAAVPSPPP 140
    .. . |.|.|  . ::::: .:..     ::|::    ...:.. .|| .
 52 VVSINVEGSTTVNTPRMPRNFQQ.......FFGDD....SPFCQEGSPFQ  90

141 ASPRSQYNFIADVVEKTAPAVVYIEILDRHPFLGREVPISNGSGFVVAAD 190
    .|| :|      ::..: .:..   ::..:          |||.:::.||
 91 SSPFCQ...GGQGGNGGGQQQKFMAL..............GSGVIIDAD 122

191 .GLIVTNAHVVADRRRVRVRLLSGDTYEAVVTAVDPVADIATLRIQTKEP 239
    |.:|||.|||.:   ::|.| .| .::|  :.: || .||| :.||...
123 KGYVVTNNHVVDNATVIKVQLSDGRKFDAKMVGKDPRSDIALIQIQNPKN 172

240 LPTLPLGRSADVRQGEFVVAMGSPFALQNTITSGIVSSAQRPARDLGLPQ 289
    |..:.:: |..:| |:::.|::|.||:|.:|:||||||. .|.   || .
173 LTAIKMADSDALRVGDYTVGIGNPFGLGETVTSGIVSALGRS....GLNA 218

290 TNVE.YIQTDAAIDFGNSGGPLVNLDGEVIGVNTMKVTA.....GISFAI 333
    .| | :|||||||: |||||:|||:|||:||:||:|| :.:    ||:|||
219 ENYENFIQTDAAINRGNSGGALVNLNGELIGINTAILAPDGGNIGIGFAI 268

334 PSDRLREF.........LHRGE............................ 346
    |||:.::::         :.|||
269 PSNMVKNLTSQMVEYGQVKRGELGIMGTELNSELAKAMKVDAQRGAFVSQ 318

347 .KKNSSSGISG.................SQRRYIGVM....MLTL...  369
     .|||.: .|                  . |  :|.|    .|||
319 VLPNSSAAKAGIKAGDVITSLNGKPISSFAALRAQVGTMPVGSKLTLGLL 368

370 ......................SPSILAELQLREPSFPDVQHGVLIHKVIL 398
                          |.||:.::: || | .: ::||:::.|
369 RDGKQVNVNLELQQSSQNQVDSSSIFNGIEGAEMSNKGKDQGVVVNNVKT 418

399 GSPAHRAGLRPGDVILAIGEQMVQNAEDVYEAVRTQ.SQLAVQIRRGRET 447
    |.||  ||:.|||::|  |.| ...:| |.| ...:. .. | ||:.|.||
419 GTPAAQIGLKKGDVIIGANQQAVKNIAELRKVLDSKPSVLALNIQRGDRH 468

448 LTLYVTPEVTE 458
    |.: .. .:..
469 LPVNAVISLNP 479
```

FIGURE 1/3

```
            1                                                    50
PSP1-2   CGTGGATCCC GAGAAAGAGG CGCAGGACGA GGAGGCAGAA CCCGACTGGC
PSP1-1   CGTGGATCCC GAGAAAGAGG CGCAGGACGA GGAGGCAGAA CCCGACTGGC
PSP1-3   CGTGGATCCC GAGAAAGAGG CGCAGGACGA GGAGGCAGAA CCCGACTGGC
PSP1-4   CGTGGATCCC GAGAAAGAGG CGCAGGACGA GGAGGCAGAA CCCGACTGGC 51                                                  100
PSP1-2   GCGTAGAGCA GCAGCACGAG CAGTAGGAAG CAGTCACCCG GAAGCCTGGG
PSP1-1   GCGTAGAGCA GCAGCACGAG CAGTAGGAAG CAGTCACCCG GAAGCCTGGG
PSP1-3   GCGTAGAGCA GCAGCACGAG CAGTAGGAAG CAGTCACCCG GAAGCCTGGG
PSP1-4   GCGTAGAGCA GCAGCACGAG CAGTAGGAAG CAGTCACCCG GAAGCCTGGG 101                                                 150
PSP1-2   GGCGAGAGGC GAAGTGGTCA GGCGCCGAAG GCCGAGAGCA CGCGGGGATC
PSP1-1   GGCGAGAGGC GAAGTGGTCA GGCGCCGAAG GCCGAGAGCA CGCGGGGATC
PSP1-3   GGCGAGAGGC GAAGTGGTCA GGCGCCGAAG GCCGAGAGCA CGCGGGGATC
PSP1-4   GGCGAGAGGC GAAGTGGTCA GGCGCCGAAG GCCGAGAGCA CGCGGGGATC 151                                                 200
PSP1-2   GGTCTCTTCC CGCCGGGTCT CTTACCGGTG CGAGTCAAAG AGCCGCTCCG
PSP1-1   GGTCTCTTCC CGCCGGGTCT CTTACCGGTG CGAGTCAAAG AGCCGCTCCG
PSP1-3   GGTCTCTTCC CGCCGGGTCT CTTACCGGTG CGAGTCAAAG AGCCGCTCCG
PSP1-4   GGTCTCTTCC CGCCGGGTCT CTTACCGGTG CGAGTCAAAG AGCCGCTCCG 201                                                 250
PSP1-2   GCCCCGGCCC TGAGGGAAGC TCCATAACTG CTGCTTCAGG AGCGCCCGGC
PSP1-1   GCCCCGGCCC TGAGGGAAGC TCCATAACTG CTGCTTCAGG AGCGCCCGGC
PSP1-3   GCCCCGGCCC TGAGGGAAGC TCCATAACTG CTGCTTCAGG AGCGCCCGGC
PSP1-4   GCCCCGGCCC TGAGGGAAGC TCCATAACTG CTGCTTCAGG AGCGCCCGGC 251                                                 300
PSP1-2   CGTCGCCGCC GCCGCCATTT TCGCGCCCGG CCGCAGGGGC TCTTGGGAAG
PSP1-1   CGTCGCCGCC GCCGCCATTT TCGCGCCCGG CCGCAGGGGC TCTTGGGAAG
PSP1-3   CGTCGCCGCC GCCGCCATTT TCGCGCCCGG CCGCAGGGGC TCTTGGGAAG
PSP1-4   CGTCGCCGCC GCCGCCATTT TCGCGCCCGG CCGCAGGGGC TCTTGGGAAG
```

FIGURE 2A/3

```
              301                                                        350
PSP1-2   GCGGAGTCTT  TGGGCATCCG  CCCGGGGTGA  GGGGACCCGA  AGTCCTGAGG
PSP1-1   GCGGAGTCTT  TGGGCATCCG  CCCGGGGTGA  GGGGACCCGA  AGTCCTGAGG
PSP1-3   GCGGAGTCTT  TGGGCATCCG  CCCGGGGTGA  GGGGACCCGA  AGTCCTGAGG
PSP1-4   GCGGAGTCTT  TGGGCATCCG  CCCGGGGTGA  GGGGACCCGA  AGTCCTGAGG 351                                                        400
PSP1-2   CGCGCCGGAA  GGGCTAGCGG  TCCCAGCATA  CCCCGCGGCC  CCTTGGGCCG
PSP1-1   CGCGCCGGAA  GGGCTAGCGG  TCCCAGCATA  CCCCGCGGCC  CCTTGGGCCG
PSP1-3   CGCGCCGGAA  GGGCTAGCGG  TCCCAGCATA  CCCCGCGGCC  CCTTGGGCCG
PSP1-4   CGCGCCGGAA  GGGCTAGCGG  TCCCAGCATA  CCCCGCGGCC  CCTTGGGCCG 401                                                        450
PSP1-2   TCTCACAACT  CGCGTCCGGC  GGAGACCACA  ATTCCCGGCA  TTCGTGGGGC
PSP1-1   TCTCACAACT  CGCGTCCGGC  GGAGACCACA  ATTCCCGGCA  TTCGTGGGGC
PSP1-3   TCTCACAACT  CGCGTCCGGC  GGAGACCACA  ATTCCCGGCA  TTCGTGGGGC
PSP1-4   TCTCACAACT  CGCGTCCGGC  GGAGACCACA  ATTCCCGGCA  TTCGTGGGGC 451                                                        500
PSP1-2   AGGGAGGAGT  CGGCCTCCCG  GAATCCTGGT  CCCGGCGTGC  ACTTCTGAAG
PSP1-1   AGGGAGGAGT  CGGCCTCCCG  GAATCCTGGT  CCCGGCGTGC  ACTTCTGAAG
PSP1-3   AGGGAGGAGT  CGGCCTCCCG  GAATCCTGGT  CCCGGCGTGC  ACTTCTGAAG
PSP1-4   AGGGAGGAGT  CGGCCTCCCG  GAATCCTGGT  CCCGGCGTGC  ACTTCTGAAG 501                                                        550
PSP1-2   GACTTCAGGT  ACCGGCGTGC  CCCGCGTCCT  ACTGTCCGCC  TGCTCGCGTC
PSP1-1   GACTTCAGGT  ACCGGCGTGC  CCCGCGTCCT  ACTGTCCGCC  TGCTCGCGTC
PSP1-3   GACTTCAGGT  ACCGGCGTGC  CCCGCGTCCT  ACTGTCCGCC  TGCTCGCGTC
PSP1-4   GACTTCAGGT  ACCGGCGTGC  CCCGCGTCCT  ACTGTCCGCC  TGCTCGCGTC 551                                                        600
PSP1-2   CTGGGTGCCG  CCTCTGAGTA  GGGCGGGCGA  GGAGGCAGCC  AAGGCGGAGC
PSP1-1   CTGGGTGCCG  CCTCTGAGTA  GGGCGGGCGA  GGAGGCAGCC  AAGGCGGAGC
PSP1-3   CTGGGTGCCG  CCTCTGAGTA  GGGCGGGCGA  GGAGGCAGCC  AAGGCGGAGC
PSP1-4   CTGGGTGCCG  CCTCTGAGTA  GGGCGGGCGA  GGAGGCAGCC  AAGGCGGAGC
```

FIGURE 2B/3

```
        601                                                    650
PSP1-2  TGATGGCTGC GCCGAGGGCG GGGCGGGGTG CAGGCTGGAG CCTTCGGGCA
PSP1-1  TGATGGCTGC GCCGAGGGCG GGGCGGGGTG CAGGCTGGAG CCTTCGGGCA
PSP1-3  TGATGGCTGC GCCGAGGGCG GGGCGGGGTG CAGGCTGGAG CCTTCGGGCA
PSP1-4  TGATGGCTGC GCCGAGGGCG GGGCGGGGTG CAGGCTGGAG CCTTCGGGCA 651                                                    700
PSP1-2  TGGCGGGCTT TGGGGGGCAT TTGCTGGGGG AGGAGACCCC GTTTGACCCC
PSP1-1  TGGCGGGCTT TGGGGGGCAT TCGCTGGGGG AGGAGACCCC GTTTGACCCC
PSP1-3  TGGCGGGCTT TGGGGGGCAT TCGCTGGGGG AGGAGACCCC GTTTGACCCC
PSP1-4  TGGCGGGCTT TGGGGGGCAT TCGCTGGGGG AGGAGACCCC GTTTGACCCC 701                                                    750
PSP1-2  TGACCTCCGG GCCCTGCTGA CGTCAGGAAC TTCTGACCCC CGGGCCCGAG
PSP1-1  TGACCTCCGG GCCCTGCTGA CGTCAGGAAC TTCTGACCCC CGGGCCCGAG
PSP1-3  TGACCTCCGG GCCCTGCTGA CGTCAGGAAC TTCTGACCCC CGGGCCCGAG
PSP1-4  TGACCTCCGG GCCCTGCTGA CGTCAGGAAC TTCTGACCCC CGGGCCCGAG 751                                                    800
PSP1-2  TGACTTATGG GACCCCCAGT CTCTGGGCCC GGTTGTCTGT TGGGGTCACT
PSP1-1  TGACTTATGG GACCCCCAGT CTCTGGGCCC GGTTGTCTGT TGGGGTCACT
PSP1-3  TGACTTATGG GACCCCCAGT CTCTGGGCCC GGTTGTCTGT TGGGGTCACT
PSP1-4  TGACTTATGG GACCCCCAGT CTCTGGGCCC GGTTGTCTGT TGGGGTCACT 801                                                    850
PSP1-2  GAACCCCGAG CATGCCTGAC GTCTGGGACC CCGGGTCCCC GGGCACAACT
PSP1-1  GAACCCCGAG CATGCCTGAC GTCTGGGACC CCGGGTCCCC GGGCACAACT
PSP1-3  GAACCCCGAG CATGCCTGAC GTCTGGGACC CCGGGTCCCC GGGCACAACT
PSP1-4  GAACCCCGAG CATGCCTGAC GTCTGGGACC CCGGGTCCCC GGGCACAACT 851                                                    900
PSP1-2  GACTGCGGTG ACCCCAGATA CCAGGACCCG GGAGGCCTCA GAGAACTCTG
PSP1-1  GACTGCGGTG ACCCCAGATA CCAGGACCCG GGAGGCCTCA GAGAACTCTG
PSP1-3  GACTGCGGTG ACCCCAGATA CCAGGACCCG GGAGGCCTCA GAGAACTCTG
PSP1-4  GACTGCGGTG ACCCCAGATA CCAGGACCCG GGAGGCCTCA GAGAACTCTG
```

FIGURE 2C/3

```
        901                                                      950
PSP1-2  GAACCCGTTC GCGCGCGTGG CTGGCGGTGG CGCTGGGCGC TGGGGGGGCA
PSP1-1  GAACCCGTTC GCGCGCGTGG CTGGCGGTGG CGCTGGGCGC TGGGGGGGCA
PSP1-3  GAACCCGTTC GCGCGCGTGG CTGGCGGTGG CGCTGGGCGC TGGGGGGGCA
PSP1-4  GAACCCGTTC GCGCGCGTGG CTGGCGGTGG CGCTGGGCGC TGGGGGGGCA 951                                                     1000
PSP1-2  GTGCTGTTGT TGTTGTGGGG CGGGGGTCGG GGTCCTCCGG CCGTCCTCGC
PSP1-1  GTGCTGTTGT TGTTGTGGGG CGGGGGTCGG GGTCCTCCGG CCGTCCTCGC
PSP1-3  GTGCTGTTGT TGTTGTGGGG CGGGGGTCGG GGTCCTCCGG CCGTCCTCGC
PSP1-4  GTGCTGTTGT TGTTGTGGGG CGGGGGTCGG GGTCCTCCGG CCGTCCTCGC 1001                                                    1050
PSP1-2  CGCCGTCCCT AGCCCGCCGC CCGCTTCTCC CCGGAGTCAG TACAACTTCA
PSP1-1  CGCCGTCCCT AGCCCGCCGC CCGCTTCTCC CCGGAGTCAG TACAACTTCA
PSP1-3  CGCCGTCCCT AGCCCGCCGC CCGCTTCTCC CCGGAGTCAG TACAACTTCA
PSP1-4  CGCCGTCCCT AGCCCGCCGC CCGCTTCTCC CCGGAGTCAG TACAACTTCA 1051                                                    1100
PSP1-2  TCGCAGATGT GGTGGAGAAG ACAGCACCTG CCGTGGTCTA TATCGAGATC
PSP1-1  TCGCAGATGT GGTGGAGAAG ACAGCACCTG CCGTGGTCTA TATCGAGATC
PSP1-3  TCGCAGATGT GGTGGAGAAG ACAGCACCTG CCGTGGTCTA TATCGAGATC
PSP1-4  TCGCAGATGT GGTGGAGAAG ACAGCACCTG CCGTGGTCTA TATCGAGATC 1101                                                    1150
PSP1-2  CTGGACCGGC ACCCTTTCTT GGGCCGCGAG GTCCCTATCT CGAACGGCTC
PSP1-1  CTGGACCGGC ACCCTTTCTT GGGCCGCGAG GTCCCTATCT CGAACGGCTC
PSP1-3  CTGGACCGGC ACCCTTTCTT GGGCCGCGAG GTCCCTATCT CGAACGGCTC
PSP1-4  CTGGACCGGC ACCCTTTCTT GGGCCGCGAG GTCCCTATCT CGAACGGCTC 1151                                                    1200
PSP1-2  AGGATTCGTG GTGGCTGCCG ATGGGCTCAT TGTCACCAAC GCCCATGTGG
PSP1-1  AGGATTCGTG GTGGCTGCCG ATGGGCTCAT TGTCACCAAC GCCCATGTGG
PSP1-3  AGGATTCGTG GTGGCTGCCG ATGGGCTCAT TGTCACCAAC GCCCATGTGG
PSP1-4  AGGATTCGTG GTGGCTGCCG ATGGGCTCAT TGTCACCAAC GCCCATGTGG
```

FIGURE 2D/3

```
        1201                                                       1250
PSP1-2  TGGCTGATCG GCGCAGAGTC CGTGTGAGAC TGCTAAGCGG CGACACGTAT
PSP1-1  TGGCTGATCG GCGCAGAGTC CGTGTGAGAC TGCTAAGCGG CGACACGTAT
PSP1-3  TGGCTGATCG GCGCAGAGTC CGTGTGAGAC TGCTAAGCGG CGACACGTAT
PSP1-4  TGGCTGATCG GCGCAGAGTC CGTGTGAGAC TGCTAAGCGG CGACACGTAT 1251                                                       1300
PSP1-2  GAGGCCGTGG TCACAGCTGT GGATCCCGTG GCAGACATCG CAACGCTGAG
PSP1-1  GAGGCCGTGG TCACAGCTGT GGATCCCGTG GCAGACATCG CAACGCTGAG
PSP1-3  GAGGCCGTGG TCACAGCTGT GGATCCCGTG GCAGACATCG CAACGCTGAG
PSP1-4  GAGGCCGTGG TCACAGCTGT GGATCCCGTG GCAGACATCG CAACGCTGAG 1301                                                       1350
PSP1-2  GATTCAGACT AAGGAGCCTC TCCCCACGCT GCCTCTGGGA CGCTCAGCTG
PSP1-1  GATTCAGACT AAGGAGCCTC TCCCCACGCT GCCTCTGGGA CGCTCAGCTG
PSP1-3  GATTCAGACT AAGGAGCCTC TCCCCACGCT GCCTCTGGGA CGCTCAGCTG
PSP1-4  GATTCAGACT AAGGAGCCTC TCCCCACGCT GCCTCTGGGA CGCTCAGCTG 1351                                                       1400
PSP1-2  ATGTCCGGCA AGGGGAGTTT GTTGTTGCCA TGGGAAGTCC CTTTGCACTG
PSP1-1  ATGTCCGGCA AGGGGAGTTT GTTGTTGCCA TGGGAAGTCC CTTTGCACTG
PSP1-3  ATGTCCGGCA AGGGGAGTTT GTTGTTGCCA TGGGAAGTCC CTTTGCACTG
PSP1-4  ATGTCCGGCA AGGGGAGTTT GTTGTTGCCA TGGGAAGTCC CTTTGCACTG 1401                                                       1450
PSP1-2  CAGAACACGA TCACATCCGG CATTGTTAGC TCTGCTCAGC GTCCAGCCAG
PSP1-1  CAGAACACGA TCACATCCGG CATTGTTAGC TCTGCTCAGC GTCCAGCCAG
PSP1-3  CAGAACACGA TCACATCCGG CATTGTTAGC TCTGCTCAGC GTCCAGCCAG
PSP1-4  CAGAACACGA TCACATCCGG CATTGTTAGC TCTGCTCAGC GTCCAGCCAG 1451                                                       1500
PSP1-2  AGACCTGGGA CTCCCCCAAA CCAATGTGGA ATACATTCAA ACTGATGCAG
PSP1-1  AGACCTGGGA CTCCCCCAAA CCAATGTGGA ATACATTCAA ACTGATGCAG
PSP1-3  AGACCTGGGA CTCCCCCAAA CCAATGTGGA ATACATTCAA ACTGATGCAG
PSP1-4  AGACCTGGGA CTCCCCCAAA CCAATGTGGA ATACATTCAA ACTGATGCAG
```

FIGURE 2E/3

```
        1501                                                    1550
PSP1-2  CTATTGATTT TGGAAACTCT GGAGGTCCCC TGGTTAACCT ..........
PSP1-1  CTATTGATTT TGGAAACTCT GGAGGTCCCC TGGTTAACCT ..........
PSP1-3  CTATTGATTT TGGAAACTCT GGAGGTCCCC TGGTTAACCT GGTGAGTGAG
PSP1-4  CTATTGATTT TGGAAACTCT GGAGGTCCCC TGGTTAACCT ..........

1551                                                    1600
PSP1-2  .......... .......... .......... .......... ..........
PSP1-1  .......... .......... .......... .......... ..........
PSP1-3  ACATCCTTCC TTCCAAGAAT CCCTGCCCCA GGTCAGTGTG GGAAGGGTAG
PSP1-4  .......... .......... .......... .......... ..........

1601                                                    1650
PSP1-2  .......... .......... .......... .......... ..........
PSP1-1  .......... .......... .......... .......... ..........
PSP1-3  GTTTCCCCTA ATTCAAGGAT GTTTGGTCAA GTTTCTGAGC AGTTCTTTGT
PSP1-4  .......... .......... .......... .......... ..........

1651                                                    1700
PSP1-2  .......... .......... .......... .......... ..........
PSP1-1  .......... .......... .......... .......... ..........
PSP1-3  TGGCTATCTC TCAATATCCA ACCAGATCTC CCCAACACTT GCTGGTACTT
PSP1-4  .......... .......... .......... .......... ..........

1701                                                    1750
PSP1-2  .......... .......... .......... .......... ..........
PSP1-1  .......... .......... .......... .......... ..........
PSP1-3  TTGTTCGGGT GCCCCCATCC CCTACTATTT GTTTAGGCTA GGGAACTGGG
PSP1-4  .......... .......... .......... .....GGCTA GGGAACTGGG 1751                                                    1800
PSP1-2  .......... .....GGATG GGGAGGTGAT TGGAGTGAAC ACCATGAAGG
PSP1-1  .......... .....GGATG GGGAGGTGAT TGGAGTGAAC ACCATGAAGG
PSP1-3  GGCTGTATCC CTGCAGGATG GGGAGGTGAT TGGAGTGAAC ACCATGAAGG
PSP1-4  GGCTGTATCC CTGCAGGATG GGGAGGTGAT TGGAGTGAAC ACCATGAAGG
```

FIGURE 2F/3

```
        1801                                                    1850
PSP1-2  TCACAGCTGG AATCTCCTTT GCCATCCCTT CTGATCGTCT TCGAGAGTTT
PSP1-1  TCACAGCTGG AATCTCCTTT GCCATCCCTT CTGATCGTCT TCGAGAGTTT
PSP1-3  TCACAGCTGG AATCTCCTTT GCCATCCCTT CTGATCGTCT TCGAGAGTTT
PSP1-4  TCACAGCTGG AATCTCCTTT GCCATCCCTT CTGATCGTCT TCGAGAGTTT 1851                                                    1900
PSP1-2  CTGCATCGTG GGGAAAAGAA GAATTCCTCC TCCGGAATCA GTGGGTCCCA
PSP1-1  CTGCATCGTG GGGAAAAGAA GAATTCCTCC TCCGGAATCA GTGGGTCCCA
PSP1-3  CTGCATCGTG GGGAAAAGAA GAATTCCTCC TCCGGAATCA GTGGGTCCCA
PSP1-4  CTGCATCGTG GGGAAAAGAA GAATTCCTCC TCCGGAATCA GTGGGTCCCA 1901                                                    1950
PSP1-2  GCGGCGCTAC ATTGGGGTGA TGATGCTGAC CCTGAGTCCC AGCATCCTTG
PSP1-1  GCGGCGCTAC ATTGGGGTGA TGATGCTGAC CCTGAGTCCC AGCATCCTTG
PSP1-3  GCGGCGCTAC ATTGGGGTGA TGATGCTGAC CCTGAGTCCC AGCATCCTTG
PSP1-4  GCGGCGCTAC ATTGGGGTGA TGATGCTGAC CCTGAGTCCC A.........

1951                                                    2000
PSP1-2  CTGAACTACA GCTTCGAGAA CCAAGCTTTC CCGATGTTCA GCATGGTGTA
PSP1-1  CTGAACTACA GCTTCGAGAA CCAAGCTTTC CCGATGTTCA GCATGGTGTA
PSP1-3  CTGAACTACA GCTTCGAGAA CCAAGCTTTC CCGATGTTCA GCATGGTGTA
PSP1-4  .......... .......... .......... .......... ..........

2001                                                    2050
PSP1-2  CTCATCCATA AAGTCATCCT GGGCTCCCCT GCACACCGGG CTGGTCTGCG
PSP1-1  CTCATCCATA AAGTCATCCT GGGCTCCCCT GCACACCGGG CTGGTCTGCG
PSP1-3  CTCATCCATA AAGTCATCCT GGGCTCCCCT GCACACCGGG CTGGTCTGCG
PSP1-4  .......... .......... .......... .......GGG CTGGTCTGCG 2051                                                    2100
PSP1-2  GCCTGGTGAT GTGATTTTGG CCATTGGGGA GCAGATGGTA CAAAATGCTG
PSP1-1  GCCTGGTGAT GTGATTTGG CCATTGGGGA GCAGATGGTA CAAAATGCTG
PSP1-3  GCCTGGTGAT GTGATTTTGG CCATTGGGGA GCAGATGGTA CAAAATGCTG
PSP1-4  GCCTGGTGAT GTGATTTTGG CCATTGGGGA GCAGATGGTA CAAAATGCTG
```

FIGURE 2G/3

```
        2101                                                    2150
PSP1-2  AAGATGTTTA TGAAGCTGTT CGAACCCAAT CCCAGTTGGC AGTGCAGATC
PSP1-1  AAGATGTTTA TGAAGCTGTT CGAACCCAAT CCCAGTTGGC AGTGCAGATC
PSP1-3  AAGATGTTTA TGAAGCTGTT CGAACCCAAT CCCAGTTGGC AGTGCAGATC
PSP1-4  AAGATGTTTA TGAAGCTGTT CGAACCCAAT CCCAGTTGGC AGTGCAGATC 2151                                                    2200
PSP1-2  CGGCGGGGAC GAGAAACACT GACCTTATAT GTGACCCCTG AGGTCACAGA
PSP1-1  CGGCGGGGAC GAGAAACACT GACCTTATAT GTGACCCCTG AGGTCACAGA
PSP1-3  CGGCGGGGAC GAGAAACACT GACCTTATAT GTGACCCCTG AGGTCACAGA
PSP1-4  CGGCGGGGAC GAGAAACACT GACCTTATAT GTGACCCCTG AGGTCACAGA 2201                                                    2250
PSP1-2  ATGAATAGAT CACCAAGAGT ATGAGGCTCC TGCTCTGATT TCCTCCTTGC
PSP1-1  ATGAATAGAT CACCAAGAGT ATGAGGCTCC TGCTCTGATT TCCTCCTTGC
PSP1-3  ATGAATAGAT CACCAAGAGT ATGAGGCTCC TGCTCTGATT TCCTCCTTGC
PSP1-4  ATGAATAGAT CACCAAGAGT ATGAGGCTCC TGCTCTGATT TCCTCCTTGC 2251                                                    2300
PSP1-2  CTTTCTGGCT GAGGTTCTGA GGGCACCGAG ACAGAGGGTT AAATGAACCA
PSP1-1  CTTTCTGGCT GAGGTTCTGA GGGCACCGAG ACAGAGGGTT AAATGAACCA
PSP1-3  CTTTCTGGCT GAGGTTCTGA GGGCACCGAG ACAGAGGGTT AAATGAACCA
PSP1-4  CTTTCTGGCT GAGGTTCTGA GGGCACCGAG ACAGAGGGTT AAATGAACCA 2301                                                    2350
PSP1-2  GTGGGGGCAG GTCCCTCCAA CCACCAGCAC TGACTCCTGG GCTCTGAAGA
PSP1-1  GTGGGGGCAG GTCCCTCCAA CCACCAGCAC TGACTCCTGG GCTCTGAAGA
PSP1-3  GTGGGGGCAG GTCCCTCCAA CCACCAGCAC TGACTCCTGG GCTCTGAAGA
PSP1-4  GTGGGGGCAG GTCCCTCCAA CCACCAGCAC TGACTCCTGG GCTCTGAAGA 2351                                                    2400
PSP1-2  ATCACAGAAA CACTTTTTAT ATAAAATAAA ATTATACCTA GCAACATAAA
PSP1-1  ATCACAGAAA CACTTTTTAT ATAAAATAAA ATTATACCTA GCAACATAAA
PSP1-3  ATCACAGAAA CACTTTTTAT ATAAAATAAA ATTATACCTA GCAACATATT
PSP1-4  ATCACAGAAA CACTTTTTAT ATAAAATAAA ATTATACCTA GCAAAAAAAA
```

FIGURE 2H/3

```
        2401                                                      2450
PSP1-2  AAAAAAAAAA AA........ .......... .......... ..........
PSP1-1  AAAAAAAAAA AA........ .......... .......... ..........
PSP1-3  ATAGTAAAAA ATGAGGTGGG AGGGCTGGAT CTTTTCCCCC ACCAAAAGGC
PSP1-4  AAAAAAAAAA AAAAAAAAAA AAAAAAAAAA AAAAA..... ..........

2451                                                      2500
PSP1-2  .......... .......... .......... .......... ..........
PSP1-1  .......... .......... .......... .......... ..........
PSP1-3  TAGAGGTAAA GCTGTATCCC CCTAAACTTA GGGGAGATAC TGGAGCTGAC
PSP1-4  .......... .......... .......... .......... ..........

2501                                                      2550
PSP1-2  .......... .......... .......... .......... ..........
PSP1-1  .......... .......... .......... .......... ..........
PSP1-3  CATCCTGACC TCCTATTAAA GAAAATGAGC TGCTGAAAAA AAAAAAAAAA
PSP1-4  .......... .......... .......... .......... ..........

2551
PSP1-2  .
PSP1-1  .
PSP1-3  A
PSP1-4  .
```

FIGURE 2I/3

```
  1 MAAP......RAGRGAGWSLRAWRALGGIRWGRRPRLTPDLRALLTSGTS  44
    :|||      ||||:|.:       ||. :. .:| .|:       .. ..
 16 LAAPASAQLSRAGRSAPL......AAGCPDRCEPARCPPQ.....PEHCE  54

45 DPRARVTYGTPSLWARLSVGVTEPRACLTSGTPGPRAQLTAV......TP  88
    :.|||  .:|...:       .|..|. ||   :.|.. :  ..|    .:
 55 GGRARDACGCCEV.....CGAPEGAACGLQEGPCGEGLQCVVPFGVPASA  99

89 DTRTREASENSGTRSRAWLAVALGAGGAVLLLLWGGG.......RGPPAV 131
    ..| |....: :.. |.. :... :.. || |  |::::      |.|. |
100 TVRRAQAGLCVCASSEPVCGSDANTYANLCQLRAASRRSERLHRPPVIV  149

132 LAAVPSPP....PASPRSQYNFIADVVEKTAPAVVYIEILDRHPFLGREV 177
    |.. .:: ..    |.|  | .||||||||||.|||||.||:: : ||   |||
150 LQRGACGQGQEDPNSLRHKYNFIADVVEKIAPAVVHIELFRKLPFSKREV 199

178 PISNGSGFVVAADGLIVTNAHVVADRRRVRVRLLSGDTYEAVVTAVDPVA 227
    |:..||||:|..||||||||||||.:::||:| | .|.|||| :..||. |
200 PVASGSGFIVSEDGLIVTNAHVVTNKHRVKVELKNGATYEAKIKDVDEKA 249

228 DIATLRIQTKEPLPTLPLGRSADVRQGEFVVAMGSPFALQNTITSGIVSS 277
    ||| ::|: .:.||.| ||||.:::|.|||||||:||||.||||:|.||||.
250 DIALIKIDHQGKLPVLLLGRSSELRPGEFVVAIGSPFSLQNTVTTGIVST 299

278 AQRPARDLGLPQTNVEYIQTDAAIDFGNSGGPLVNLDGEVIGVNTMKVTA 327
    .||.:::|||...:::||||||| |::|||||||||||||||||:||:||||
300 TQRGGKELGLRNSDMDYIQTDAIINYGNSGGPLVNLDGEVIGINTLKVTA 349

328 GISFAIPSDRLREFLHRGEKKNSSSGISGSQRRYIGVMMLTLSPSILAEL 377
    ||||||||||:::.||    :...:  ..|  . ..:::|||:.|:.|..|   ||
350 GISFAIPSDKIKKFLTESHDRQ.AKGKAITKKKYIGIRMMSLTSSKAKEL 398

378 QLREPSFPDVQHGVLIHKVILGSPAHRAGLRPGDVILAIGEQMVQNAEDV 427
    . |...||||   |..| .|| :.||. :||:...|||:.|.:| | .|:||
399 KDRHRDFPDVISGAYIIEVIPDTPAEAGGLKENDVIISINGQSVVSANDV 448

428 YEAVRTQSQLAVQIRRGRETLTLYVTPEVTE 458
    :..:: :| |.: :|||.|.: : |.||  .:
449 SDVIKRESTLNMVVRRGNEDIMITVIPEEID 479
```

FIGURE 3/3

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:

(A) LENGTH: 732 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

```
GGGACTCCCC CAAACCAATG TGGAATACAT TCAAACTGAT GCAGCTATTG ATTTTGGAAA      60

CTCTGGAGGT CCCCTGGTTA ACCTGGATGG GGAGGTGATT GGAGTGAACA CCATGAAGGT     120

CACAGCTGGA ATCTCCTTTG CCATCCCTTC TGATCGTCTT CGAGAGTTTC TGCATCGTGG     180

GGAAAAGAAG AATTCCTCCT CCGGAATCAG TGGGTCCCAG CGGCGCTACA TTGGGGTGAT     240

GATGCTGACC CTGAGTCCCA GCATCCTTGC TGAACTACAG CTTCGAGAAC CAAGCTTTCC     300

CGATGTTCAG CATGGTGTAC TCATCCATAA AGTCATCCTG GGCTCCCCTG CACACCGGGC     360

TGGTCTGCGG CCTGGTGATG TGATTTTGGC CATTGGGGAG CAGATGGTAC AAAATGCTGA     420

AGATGTTTAT GAAGCTGTTC GAACCCAATC CCAGTTGGCA GTGCAGATCC GGCGGGGACG     480

AGAAACACTG ACCTTATATG TGACCCCTGA GGTCACAGAA TGAATAGATC ACCAAGAGTA     540

TGAGGCTCCT GCTCTGATTT CCTCCTTGCC TTTCTGGCTG AGGTTCTGAG GCACCGAGA      600

CAGAGGGTTA AATGAACCAG TGGGGGCAGG TCCCTCCAAC CACCAGCACT GACTCCTGGG     660

CTCTGAAGAA TCACAGAAAC ACTTTTTATA TAAAATAAAA TTATACCTAG CAACAAAAAA     720

AAAAAAAAAA AA                                                         732
```

(2) INFORMATION FOR SEQ ID NO:2:

(i) SEQUENCE CHARACTERISTICS:
        (A) LENGTH: 173 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:2:

```
Gly Leu Pro Gln Thr Asn Val Glu Tyr Ile Gln Thr Asp Ala Ala Ile
 1               5                  10                  15

Asp Phe Gly Asn Ser Gly Gly Pro Leu Val Asn Leu Asp Gly Glu Val
                20                  25                  30

Ile Gly Val Asn Thr Met Lys Val Thr Ala Gly Ile Ser Phe Ala Ile
            35                  40                  45

Pro Ser Asp Arg Leu Arg Glu Phe Leu His Arg Gly Glu Lys Lys Asn
        50                  55                  60

Ser Ser Ser Gly Ile Ser Gly Ser Gln Arg Arg Tyr Ile Gly Val Met
65                  70                  75                  80
```

```
Met Leu Thr Leu Ser Pro Ser Ile Leu Ala Glu Leu Gln Leu Arg Glu
                    85                  90                  95

Pro Ser Phe Pro Asp Val Gln His Gly Val Leu Ile His Lys Val Ile
            100                 105                 110

Leu Gly Ser Pro Ala His Arg Ala Gly Leu Arg Pro Gly Asp Val Ile
        115                 120                 125

Leu Ala Ile Gly Glu Gln Met Val Gln Asn Ala Glu Asp Val Tyr Glu
    130                 135                 140

Ala Val Arg Thr Gln Ser Gln Leu Ala Val Gln Ile Arg Arg Gly Arg
145                 150                 155                 160

Glu Thr Leu Thr Leu Tyr Val Thr Pro Glu Val Thr Glu
                165                 170
```

(2) INFORMATION FOR SEQ ID NO:3:

(i) SEQUENCE CHARACTERISTICS:
        (A) LENGTH: 1787 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

```
CCCAGTCTCT GGGCCCGGTT GTCTGTTGGG GTCACTGAAC CCCGAGCATG CCTGACGTCT    60

GGGACCCCGG GTCCCCGGGC ACAACTGACT GCGGTGACCC CAGATACCAG GACCCGGGAG   120

GCCTCAGAGA ACTCTGGAAC CCGTTCGCGC GCGTGGCTGG CGGTGGCGCT GGGCGCTGGG   180

GGGGCAGTGC TGTTGTTGTT GTGGGGCGGG GGTCGGGGTC CTCCGGCCGT CCTCGCCGCC   240

GTCCCTAGCC CGCCGCCCGC TTCTCCCCGG AGTCAGTACA ACTTCATCGC AGATGTGGTG   300

GAGAAGACAG CACCTGCCGT GGTCTATATC GAGATCCTGG ACCGGCACCC TTTCTTGGGC   360

CGCGAGGTCC CTATCTCGAA CGGCTCAGGA TTCGTGGTGG CTGCCGATGG GCTCATTGTC   420

ACCAACGCCC ATGTGGTGGC TGATCGGCGC AGAGTCCGTG TGAGACTGCT AAGCGGCGAC   480

ACGTATGAGG CCGTGGTCAC AGCTGTGGAT CCCGTGGCAG ACATCGCAAC GCTGAGGATT   540

CAGACTAAGG AGCCTCTCCC CACGCTGCCT CTGGGACGCT CAGCTGATGT CCGGCAAGGG   600

GAGTTTGTTG TTGCCATGGG AAGTCCCTTT GCACTGCAGA ACACGATCAC ATCCGGCATT   660

GTTAGCTCTG CTCAGCGTCC AGCCAGAGAC CTGGGACTCC CCCAAACCAA TGTGGAATAC   720

ATTCAAACTG ATGCAGCTAT TGATTTTGGA AACTCTGGAG GTCCCCTGGT TAACCTGGTG   780

AGTGAGACAT CCTTCCTTCC AAGAATCCCT GCCCCAGGTC AGTGTGGGAA GGGTAGGTTT   840

CCCCTAATTC AAGGATGTTT GGTCAAGTTT CTGAGCAGTT CTTTGTTGGC TATCTCTCAA   900

TATCCAACCA GATCTCCCCA ACACTTGCTG GTACTTTTGT TCGGGTGCCC CCATCCCCTA   960

CTATTTGTTT AGGCTAGGGA ACTGGGGGCT GTATCCCTGC AGGATGGGGA GGTGATTGGA  1020

GTGAACACCA TGAAGGTCAC AGCTGGAATC TCCTTTGCCA TCCCTTCTGA TCGTCTTCGA  1080

GAGTTTCTGC ATCGTGGGGA AAAGAAGAAT TCCTCCTCCG GAATCAGTGG GTCCCAGCGG  1140

CGCTACATTG GGGTGATGAT GCTGACCCTG AGTCCCAGCA TCCTTGCTGA ACTACAGCTT  1200
```

```
CGAGAACCAA GCTTTCCCGA TGTTCAGCAT GGTGTACTCA TCCATAAAGT CATCCTGGGC    1260

TCCCCTGCAC ACCGGGCTGG TCTGCGGCCT GGTGATGTGA TTTTGGCCAT TGGGGAGCAG    1320

ATGGTACAAA ATGCTGAAGA TGTTTATGAA GCTGTTCGAA CCCAATCCCA GTTGGCAGTG    1380

CAGATCCGGC GGGGACGAGA AACACTGACC TTATATGTGA CCCCTGAGGT CACAGAATGA    1440

ATAGATCACC AAGAGTATGA GGCTCCTGCT CTGATTTCCT CCTTGCCTTT CTGGCTGAGG    1500

TTCTGAGGGC ACCGAGACAG AGGGTTAAAT GAACCAGTGG GGGCAGGTCC CTCCAACCAC    1560

CAGCACTGAC TCCTGGGCTC TGAAGAATCA CAGAAACACT TTTTATATAA AATAAAATTA    1620

TACCTAGCAA CATATTATAG TAAAAAATGA GGTGGGAGGG CTGGATCTTT TCCCCCACCA    1680

AAAGGCTAGA GGTAAAGCTG TATCCCCCTA AACTTAGGGG AGATACTGGA GCTGACCATC    1740

CTGACCTCCT ATTAAAGAAA ATGAGCTGCT GAAAAAAAAA AAAAAA                   1787
```

(2) INFORMATION FOR SEQ ID NO:4:

(i) SEQUENCE CHARACTERISTICS:
        (A) LENGTH: 323 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:4:

```
Pro Ser Leu Trp Ala Arg Leu Ser Val Gly Val Thr Glu Pro Arg Ala
 1               5                  10                  15

Cys Leu Thr Ser Gly Thr Pro Gly Pro Arg Ala Gln Leu Thr Ala Val
                20                  25                  30

Thr Pro Asp Thr Arg Thr Arg Glu Ala Ser Glu Asn Ser Gly Thr Arg
            35                  40                  45

Ser Arg Ala Trp Leu Ala Val Ala Leu Gly Ala Gly Gly Ala Val Leu
50                  55                  60

Leu Leu Leu Trp Gly Gly Gly Arg Gly Pro Pro Ala Val Leu Ala Ala
65                  70                  75                  80

Val Pro Ser Pro Pro Ala Ser Pro Arg Ser Gln Tyr Asn Phe Ile
                85                  90                  95

Ala Asp Val Val Glu Lys Thr Ala Pro Ala Val Val Tyr Ile Glu Ile
                100                 105                 110

Leu Asp Arg His Pro Phe Leu Gly Arg Glu Val Pro Ile Ser Asn Gly
            115                 120                 125

Ser Gly Phe Val Val Ala Ala Asp Gly Leu Ile Val Thr Asn Ala His
        130                 135                 140

Val Val Ala Asp Arg Arg Arg Val Arg Val Arg Leu Leu Ser Gly Asp
145                 150                 155                 160

Thr Tyr Glu Ala Val Val Thr Ala Val Asp Pro Val Ala Asp Ile Ala
                165                 170                 175

Thr Leu Arg Ile Gln Thr Lys Glu Pro Leu Pro Thr Leu Pro Leu Gly
            180                 185                 190

Arg Ser Ala Asp Val Arg Gln Gly Glu Phe Val Val Ala Met Gly Ser
        195                 200                 205
```

```
Pro Phe Ala Leu Gln Asn Thr Ile Thr Ser Gly Ile Val Ser Ser Ala
    210                 215                 220

Gln Arg Pro Ala Arg Asp Leu Gly Leu Pro Gln Thr Asn Val Glu Tyr
225                 230                 235                 240

Ile Gln Thr Asp Ala Ala Ile Asp Phe Gly Asn Ser Gly Gly Pro Leu
                245                 250                 255

Val Asn Leu Val Ser Glu Thr Ser Phe Leu Pro Arg Ile Pro Ala Pro
            260                 265                 270

Gly Gln Cys Gly Lys Gly Arg Phe Pro Leu Ile Gln Gly Cys Leu Val
        275                 280                 285

Lys Phe Leu Ser Ser Ser Leu Leu Ala Ile Ser Gln Tyr Pro Thr Arg
    290                 295                 300

Ser Pro Gln His Leu Leu Val Leu Leu Phe Gly Cys Pro His Pro Leu
305                 310                 315                 320

Leu Phe Val
```

(2) INFORMATION FOR SEQ ID NO:5:

(i) SEQUENCE CHARACTERISTICS:
        (A) LENGTH: 1503 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

```
CTTCGGGCAT GGCGGGCTTT GGGGGGCATT CGCTGGGGGA GGAGACCCCG TTTGACCCCT    60

GACCTCCGGG CCCTGCTGAC GTCAGGAACT TCTGACCCCC GGGCCCGAGT GACTTATGGG   120

ACCCCCAGTC TCTGGGCCCG GTTGTCTGTT GGGGTCACTG AACCCCGAGC ATGCCTGACG   180

TCTGGGACCC CGGGTCCCCG GCACAACTG ACTGCGGTGA CCCCAGATAC CAGGACCCGG    240

GAGGCCTCAG AGAACTCTGG AACCCGTTCG CGCGCGTGGC TGGCGGTGGC GCTGGGCGCT   300

GGGGGGGCAG TGCTGTTGTT GTTGTGGGGC GGGGGTCGGG GTCCTCCGGC CGTCCTCGCC   360

GCCGTCCCTA GCCCGCCGCC CGCTTCTCCC CGGAGTCAGT ACAACTTCAT CGCAGATGTG   420

GTGGAGAAGA CAGCACCTGC CGTGGTCTAT ATCGAGATCC TGGACCGGCA CCCTTTCTTG   480

GGCCGCGAGG TCCCTATCTC GAACGGCTCA GGATTCGTGG TGGCTGCCGA TGGGCTCATT   540

GTCACCAACG CCCATGTGGT GGCTGATCGG CGCAGAGTCC GTGTGAGACT GCTAAGCGGC   600

GACACGTATG AGGCCGTGGT CACAGCTGTG GATCCCGTGG CAGACATCGC AACGCTGAGG   660

ATTCAGACTA AGGAGCCTCT CCCCACGCTG CCTCTGGGAC GCTCAGCTGA TGTCCGGCAA   720

GGGGAGTTTG TTGTTGCCAT GGGAAGTCCC TTTGCACTGC AGAACACGAT CACATCCGGC   780

ATTGTTAGCT CTGCTCAGCG TCCAGCCAGA GACCTGGGAC TCCCCCAAAC CAATGTGGAA   840

TACATTCAAA CTGATGCAGC TATTGATTTT GGAAACTCTG GAGGTCCCCT GGTTAACCTG   900

GCTAGGGAAC TGGGGGCTGT ATCCCTGCAG GATGGGGAGG TGATTGGAGT GAACACCATG   960

AAGGTCACAG CTGGAATCTC CTTTGCCATC CCTTCTGATC GTCTTCGAGA GTTTCTGCAT  1020

CGTGGGGAAA AGAAGAATTC CTCCTCCGGA ATCAGTGGGT CCCAGCGGCG CTACATTGGG  1080
```

```
GTGATGATGC TGACCCTGAG TCCCAGGGCT GGTCTGCGGC CTGGTGATGT GATTTTGGCC    1140

ATTGGGGAGC AGATGGTACA AAATGCTGAA GATGTTTATG AAGCTGTTCG AACCCAATCC    1200

CAGTTGGCAG TGCAGATCCG GCGGGGACGA GAAACACTGA CCTTATATGT GACCCCTGAG    1260

GTCACAGAAT GAATAGATCA CCAAGAGTAT GAGGCTCCTG CTCTGATTTC CTCCTTGCCT    1320

TTCTGGCTGA GGTTCTGAGG GCACCGAGAC AGAGGGTTAA ATGAACCAGT GGGGCAGGT     1380

CCCTCCAACC ACCAGCACTG ACTCCTGGGC TCTGAAGAAT CACAGAAACA CTTTTTATAT    1440

AAAATAAAAT TATACCTAGC AAAAAAAAAA AAAAAAAAAA AAAAAAAAAA AAAAAAAAA     1500

AAA                                                                 1503
```

(2) INFORMATION FOR SEQ ID NO:6:

(i) SEQUENCE CHARACTERISTICS:
        (A) LENGTH: 423 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:6:

```
Leu Arg Ala Trp Arg Ala Leu Gly Gly Ile Arg Trp Gly Arg Arg Pro
 1               5                  10                  15

Arg Leu Thr Pro Asp Leu Arg Ala Leu Leu Thr Ser Gly Thr Ser Asp
            20                  25                  30

Pro Arg Ala Arg Val Thr Tyr Gly Thr Pro Ser Leu Trp Ala Arg Leu
        35                  40                  45

Ser Val Gly Val Thr Glu Pro Arg Ala Cys Leu Thr Ser Gly Thr Pro
50                  55                  60

Gly Pro Arg Ala Gln Leu Thr Ala Val Thr Pro Asp Thr Arg Thr Arg
65                  70                  75                  80

Glu Ala Ser Glu Asn Ser Gly Thr Arg Ser Arg Ala Trp Leu Ala Val
                85                  90                  95

Ala Leu Gly Ala Gly Ala Val Leu Leu Leu Trp Gly Gly Gly
            100                 105                 110

Arg Gly Pro Pro Ala Val Leu Ala Ala Val Pro Ser Pro Pro Ala
        115                 120                 125

Ser Pro Arg Ser Gln Tyr Asn Phe Ile Ala Asp Val Glu Lys Thr
    130                 135                 140

Ala Pro Ala Val Val Tyr Ile Glu Ile Leu Asp Arg His Pro Phe Leu
145                 150                 155                 160

Gly Arg Glu Val Pro Ile Ser Asn Gly Ser Gly Phe Val Val Ala Ala
                165                 170                 175

Asp Gly Leu Ile Val Thr Asn Ala His Val Val Ala Asp Arg Arg
            180                 185                 190

Val Arg Val Arg Leu Leu Ser Gly Asp Thr Tyr Glu Ala Val Val Thr
        195                 200                 205

Ala Val Asp Pro Val Ala Asp Ile Ala Thr Leu Arg Ile Gln Thr Lys
    210                 215                 220
```

```
Glu Pro Leu Pro Thr Leu Pro Leu Gly Arg Ser Ala Asp Val Arg Gln
225                 230                 235                 240

Gly Glu Phe Val Val Ala Met Gly Ser Pro Phe Ala Leu Gln Asn Thr
            245                 250                 255

Ile Thr Ser Gly Ile Val Ser Ser Ala Gln Arg Pro Ala Arg Asp Leu
                260                 265                 270

Gly Leu Pro Gln Thr Asn Val Glu Tyr Ile Gln Thr Asp Ala Ala Ile
            275                 280                 285

Asp Phe Gly Asn Ser Gly Gly Pro Leu Val Asn Leu Ala Arg Glu Leu
            290                 295                 300

Gly Ala Val Ser Leu Gln Asp Gly Glu Val Ile Gly Val Asn Thr Met
305                 310                 315                 320

Lys Val Thr Ala Gly Ile Ser Phe Ala Ile Pro Ser Asp Arg Leu Arg
                325                 330                 335

Glu Phe Leu His Arg Gly Glu Lys Lys Asn Ser Ser Ser Gly Ile Ser
            340                 345                 350

Gly Ser Gln Arg Arg Tyr Ile Gly Val Met Met Leu Thr Leu Ser Pro
            355                 360                 365

Arg Ala Gly Leu Arg Pro Gly Asp Val Ile Leu Ala Ile Gly Glu Gln
            370                 375                 380

Met Val Gln Asn Ala Glu Asp Val Tyr Glu Ala Val Arg Thr Gln Ser
385                 390                 395                 400

Gln Leu Ala Val Gln Ile Arg Arg Gly Arg Glu Thr Leu Thr Leu Tyr
                405                 410                 415

Val Thr Pro Glu Val Thr Glu
            420
```

(2) INFORMATION FOR SEQ ID NO:7:

(i) SEQUENCE CHARACTERISTICS:
        (A) LENGTH: 1835 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 251...1624
        (D) OTHER INFORMATION:

(xi) SEQUENCE DESCRIPTION: SEQ ID NO:7:

```
GGCCGGAAGG GCTAGCGGTC CCAGCATACC CCGCGGCCCC TTGGGCCGTC TCACAACTCG      60

CGTCCGGCGG AGACCACAAT TCCCGGCATT CGTGGGGCAT GGAGGAGTCG GCCTCCCGGA     120

ATCCTGGTCC CGGCGTGCAC TTCTGAAGGA CTTCAGGTAC CGGCGTGCCC CGCGTCCTAC     180

TGTCCGCCTG CTCGCGTCCT GGGTGCCGCC TCTGAGTAGG GCGGGCGAGG AGGCAGCCAA     240

GGCGGAGCTG ATG GCT GCG CCG AGG GCG GGG CGG GGT GCA GGC TGG AGC        289
           Met Ala Ala Pro Arg Ala Gly Arg Gly Ala Gly Trp Ser
             1               5                  10

CTT CGG GCA TGG CGG GCT TTG GGG GGC ATT TGC TGG GGG AGG AGA CCC       337
Leu Arg Ala Trp Arg Ala Leu Gly Gly Ile Cys Trp Gly Arg Arg Pro
 15                  20                  25
```

| | |
|---|---:|
| CGT TTG ACC CCT GAC CTC CGG GCC CTG CTG ACG TCA GGA ACT TCT GAC<br>Arg Leu Thr Pro Asp Leu Arg Ala Leu Leu Thr Ser Gly Thr Ser Asp<br>30                      35                    40                    45 | 385 |
| CCC CGG GCC CGA GTG ACT TAT GGG ACC CCC AGT CTC TGG GCC CGG TTG<br>Pro Arg Ala Arg Val Thr Tyr Gly Thr Pro Ser Leu Trp Ala Arg Leu<br>                    50                    55                    60 | 433 |
| TCT GTT GGG GTC ACT GAA CCC CGA GCA TGC CTG ACG TCT GGG ACC CCG<br>Ser Val Gly Val Thr Glu Pro Arg Ala Cys Leu Thr Ser Gly Thr Pro<br>                    65                    70                    75 | 481 |
| GGT CCC CGG GCA CAA CTG ACT GCG GTG ACC CCA GAT ACC AGG ACC CGG<br>Gly Pro Arg Ala Gln Leu Thr Ala Val Thr Pro Asp Thr Arg Thr Arg<br>       80                    85                    90 | 529 |
| GAG GCC TCA GAG AAC TCT GGA ACC CGT TCG CGC GCG TGG CTG GCG GTG<br>Glu Ala Ser Glu Asn Ser Gly Thr Arg Ser Arg Ala Trp Leu Ala Val<br>       95                   100                 105 | 577 |
| GCG CTG GGC GCT GGG GGG GCA GTG CTG TTG TTG TTG TGG GGC GGG GGT<br>Ala Leu Gly Ala Gly Gly Ala Val Leu Leu Leu Leu Trp Gly Gly Gly<br>110                   115                 120                 125 | 625 |
| CGG GGT CCT CCG GCC GTC CTC GCC GCC GTC CCT AGC CCG CCG CCC GCT<br>Arg Gly Pro Pro Ala Val Leu Ala Ala Val Pro Ser Pro Pro Pro Ala<br>                   130                 135                 140 | 673 |
| TCT CCC CGG AGT CAG TAC AAC TTC ATC GCA GAT GTG GTG GAG AAG ACA<br>Ser Pro Arg Ser Gln Tyr Asn Phe Ile Ala Asp Val Val Glu Lys Thr<br>             145                 150                 155 | 721 |
| GCA CCT GCC GTG GTC TAT ATC GAG ATC CTG GAC CGG CAC CCT TTC TTG<br>Ala Pro Ala Val Val Tyr Ile Glu Ile Leu Asp Arg His Pro Phe Leu<br>           160                 165                 170 | 769 |
| GGC CGC GAG GTC CCT ATC TCG AAC GGC TCA GGA TTC GTG GTG GCT GCC<br>Gly Arg Glu Val Pro Ile Ser Asn Gly Ser Gly Phe Val Val Ala Ala<br>175                   180                 185 | 817 |
| GAT GGG CTC ATT GTC ACC AAC GCC CAT GTG GTG GCT GAT CGG CGC AGA<br>Asp Gly Leu Ile Val Thr Asn Ala His Val Val Ala Asp Arg Arg Arg<br>190                   195                 200                 205 | 865 |
| GTC CGT GTG AGA CTG CTA AGC GGC GAC ACG TAT GAG GCC GTG GTC ACA<br>Val Arg Val Arg Leu Leu Ser Gly Asp Thr Tyr Glu Ala Val Val Thr<br>             210                 215                 220 | 913 |
| GCT GTG GAT CCC GTG GCA GAC ATC GCA ACG CTG AGG ATT CAG ACT AAG<br>Ala Val Asp Pro Val Ala Asp Ile Ala Thr Leu Arg Ile Gln Thr Lys<br>           225                 230                 235 | 961 |
| GAG CCT CTC CCC ACG CTG CCT CTG GGA CGC TCA GCT GAT GTC CGG CAA<br>Glu Pro Leu Pro Thr Leu Pro Leu Gly Arg Ser Ala Asp Val Arg Gln<br>           240                 245                 250 | 1009 |
| GGG GAG TTT GTT GTT GCC ATG GGA AGT CCC TTT GCA CTG CAG AAC ACG<br>Gly Glu Phe Val Val Ala Met Gly Ser Pro Phe Ala Leu Gln Asn Thr<br>255                   260                 265 | 1057 |
| ATC ACA TCC GGC ATT GTT AGC TCT GCT CAG CGT CCA GCC AGA GAC CTG<br>Ile Thr Ser Gly Ile Val Ser Ser Ala Gln Arg Pro Ala Arg Asp Leu<br>270                   275                 280                 285 | 1105 |
| GGA CTC CCC CAA ACC AAT GTG GAA TAC ATT CAA ACT GAT GCA GCT ATT<br>Gly Leu Pro Gln Thr Asn Val Glu Tyr Ile Gln Thr Asp Ala Ala Ile<br>             290                 295                 300 | 1153 |
| GAT TTT GGA AAC TCT GGA GGT CCC CTG GTT AAC CTG GAT GGG GAG GTG<br>Asp Phe Gly Asn Ser Gly Gly Pro Leu Val Asn Leu Asp Gly Glu Val<br>           305                 310                 315 | 1201 |
| ATT GGA GTG AAC ACC ATG AAG GTC ACA GCT GGA ATC TCC TTT GCC ATC<br>Ile Gly Val Asn Thr Met Lys Val Thr Ala Gly Ile Ser Phe Ala Ile<br>320                   325                 330 | 1249 |

```
CCT TCT GAT CGT CTT CGA GAG TTT CTG CAT CGT GGG GAA AAG AAG AAT         1297
Pro Ser Asp Arg Leu Arg Glu Phe Leu His Arg Gly Glu Lys Lys Asn
    335                 340                 345

TCC TCC TCC GGA ATC AGT GGG TCC CAG CGG CGC TAC ATT GGG GTG ATG         1345
Ser Ser Ser Gly Ile Ser Gly Ser Gln Arg Arg Tyr Ile Gly Val Met
350                 355                 360                 365

ATG CTG ACC CTG AGT CCC AGC ATC CTT GCT GAA CTA CAG CTT CGA GAA         1393
Met Leu Thr Leu Ser Pro Ser Ile Leu Ala Glu Leu Gln Leu Arg Glu
            370                 375                 380

CCA AGC TTT CCC GAT GTT CAG CAT GGT GTA CTC ATC CAT AAA GTC ATC         1441
Pro Ser Phe Pro Asp Val Gln His Gly Val Leu Ile His Lys Val Ile
                385                 390                 395

CTG GGC TCC CCT GCA CAC CGG GCT GGT CTG CGG CCT GGT GAT GTG ATT         1489
Leu Gly Ser Pro Ala His Arg Ala Gly Leu Arg Pro Gly Asp Val Ile
            400                 405                 410

TTG GCC ATT GGG GAG CAG ATG GTA CAA AAT GCT GAA GAT GTT TAT GAA         1537
Leu Ala Ile Gly Glu Gln Met Val Gln Asn Ala Glu Asp Val Tyr Glu
        415                 420                 425

GCT GTT CGA ACC CAA TCC CAG TTG GCA GTG CAG ATC CGG CGG GGA CGA         1585
Ala Val Arg Thr Gln Ser Gln Leu Ala Val Gln Ile Arg Arg Gly Arg
430                 435                 440                 445

GAA ACA CTG ACC TTA TAT GTG ACC CCT GAG GTC ACA GAA TGAATAGATC ACC      1637
Glu Thr Leu Thr Leu Tyr Val Thr Pro Glu Val Thr Glu
                450                 455

AAGAGTATGA GGCTCCTGCT CTGATTTCCT CCTTGCCTTT CTGGCTGAGG TTCTGAGGGC       1697

ACCGAGACAG AGGGTTAAAT GAACCAGTGG GGGCAGGTCC CTCCAACCAC CAGCACTGAC       1757

TCCTGGGCTC TGAAGAATCA CAGAAACACT TTTTATATAA AATAAAATTA TACCTAGCAA       1817

CATAAAAAAA AAAAAAAA                                                     1835

(2) INFORMATION FOR SEQ ID NO:8:

(i) SEQUENCE CHARACTERISTICS:
        (A) LENGTH: 458 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:8:

Met Ala Ala Pro Arg Ala Gly Arg Gly Ala Gly Trp Ser Leu Arg Ala
 1               5                  10                  15

Trp Arg Ala Leu Gly Gly Ile Cys Trp Gly Arg Pro Arg Leu Thr
            20                  25                  30

Pro Asp Leu Arg Ala Leu Leu Thr Ser Gly Thr Ser Asp Pro Arg Ala
         35                  40                  45

Arg Val Thr Tyr Gly Thr Pro Ser Leu Trp Ala Arg Leu Ser Val Gly
     50                  55                  60

Val Thr Glu Pro Arg Ala Cys Leu Thr Ser Gly Thr Pro Gly Pro Arg
65                  70                  75                  80

Ala Gln Leu Thr Ala Val Thr Pro Asp Thr Arg Thr Arg Glu Ala Ser
                85                  90                  95
```

```
Glu Asn Ser Gly Thr Arg Ser Arg Ala Trp Leu Ala Val Ala Leu Gly
            100                 105                 110

Ala Gly Gly Ala Val Leu Leu Leu Trp Gly Gly Arg Gly Pro
        115                 120                 125

Pro Ala Val Leu Ala Ala Val Pro Ser Pro Pro Ala Ser Pro Arg
130                 135                 140

Ser Gln Tyr Asn Phe Ile Ala Asp Val Val Glu Lys Thr Ala Pro Ala
145                 150                 155                 160

Val Val Tyr Ile Glu Ile Leu Asp Arg His Pro Phe Leu Gly Arg Glu
                165                 170                 175

Val Pro Ile Ser Asn Gly Ser Gly Phe Val Ala Ala Asp Gly Leu
            180                 185                 190

Ile Val Thr Asn Ala His Val Val Ala Asp Arg Arg Val Arg Val
        195                 200                 205

Arg Leu Leu Ser Gly Asp Thr Tyr Glu Ala Val Thr Ala Val Asp
        210                 215                 220

Pro Val Ala Asp Ile Ala Thr Leu Arg Ile Gln Thr Lys Glu Pro Leu
225                 230                 235                 240

Pro Thr Leu Pro Leu Gly Arg Ser Ala Asp Val Arg Gln Gly Glu Phe
                245                 250                 255

Val Val Ala Met Gly Ser Pro Phe Ala Leu Gln Asn Thr Ile Thr Ser
            260                 265                 270

Gly Ile Val Ser Ser Ala Gln Arg Pro Ala Arg Asp Leu Gly Leu Pro
        275                 280                 285

Gln Thr Asn Val Glu Tyr Ile Gln Thr Asp Ala Ala Ile Asp Phe Gly
        290                 295                 300

Asn Ser Gly Gly Pro Leu Val Asn Leu Asp Gly Glu Val Ile Gly Val
305                 310                 315                 320

Asn Thr Met Lys Val Thr Ala Gly Ile Ser Phe Ala Ile Pro Ser Asp
                325                 330                 335

Arg Leu Arg Glu Phe Leu His Arg Gly Glu Lys Lys Asn Ser Ser Ser
            340                 345                 350

Gly Ile Ser Gly Ser Gln Arg Arg Tyr Ile Gly Val Met Met Leu Thr
        355                 360                 365

Leu Ser Pro Ser Ile Leu Ala Glu Leu Gln Leu Arg Glu Pro Ser Phe
        370                 375                 380

Pro Asp Val Gln His Gly Val Leu Ile His Lys Val Ile Leu Gly Ser
385                 390                 395                 400

Pro Ala His Arg Ala Gly Leu Arg Pro Gly Asp Val Ile Leu Ala Ile
                405                 410                 415

Gly Glu Gln Met Val Gln Asn Ala Glu Asp Val Tyr Glu Ala Val Arg
            420                 425                 430

Thr Gln Ser Gln Leu Ala Val Gln Ile Arg Arg Gly Arg Glu Thr Leu
        435                 440                 445

Thr Leu Tyr Val Thr Pro Glu Val Thr Glu
        450                 455

(2) INFORMATION FOR SEQ ID NO:9:

(i) SEQUENCE CHARACTERISTICS:
        (A) LENGTH: 2764 base pairs
        (B) TYPE: nucleic acid
        (C) STRANDEDNESS: single
        (D) TOPOLOGY: linear (ii) MOLECULE TYPE: cDNA
```

(iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

```
TGGGACAGGC AGCTCCGGGG TCCGCGGTTT CACATCGGAA ACAAAACAGC GGCTGGTCTG      60
GAAGGAACCT GAGCTACGAG CCGCGGCGGC AGCGGGGCGG CGGGGAAGCG TATACCTAAT     120
CTGGGAGCCT GCAAGTGACA ACAGCCTTTG CGGTCCTTAG ACAGCTTGGC CTGGAGGAGA     180
ACACATGAAA GAAAGAACCT CAAGAGGCTT TGTTTTCTGT GAAACAGTAT TTCTATACAG     240
TTGCTCCAAT GACAGAGTTA CCTGCACCGT TGTCCTACTT CCAGAATGCA CAGATGTCTG     300
AGGACAACCA CCTGAGCAAT ACTGTACGTA GCCAGAATGA CAATAGAAA CGGCAGGAGC      360
ACAACGACAG ACGGAGCCTT GGCCACCCTG AGCCATTATC TAATGGACGA CCCCAGGGTA     420
ACTCCCGGCA GGTGGTGGAG CAAGATGAGG AAGAAGATGA GGAGCTGACA TTGAAATATG     480
GCGCCAAGCA TGTGATCATG CTCTTTGTCC CTGTGACTCT CTGCATGGTG GTGGTCGTGG     540
CTACCATTAA GTCAGTCAGC TTTTATACCC GGAAGGATGG GCAGCTAATC TATACCCCAT     600
TCACAGAAGA TACCGAGACT GTGGGCCAGA GAGCCCTGCA CTCAATTCTG AATGCTGCCA     660
TCATGATCAG TGTCATTGTT GTCATGACTA TCCTCCTGGT GGTTCTGTAT AAATACAGGT     720
GCTATAAGGT CATCCATGCC TGGCTTATTA TATCATCTCT ATTGTTGCTG TTCTTTTTTT     780
CATTCATTTA CTTGGGGGAA GTGTTTAAAA CCTATAACGT TGCTGTGGAC TACATTACTG     840
TTGCACTCCT GATCTGGAAT TTTGGTGTGG TGGGAATGAT TTCCATTCAC TGGAAAGGTC     900
CACTTCGACT CCAGCAGGCA TATCTCATTA TGATTAGTGC CCTCATGGCC CTGGTGTTTA     960
TCAAGTACCT CCCTGAATGG ACTGCGTGGC TCATCTTGGC TGTGATTTCA GTATATGATT    1020
TAGTGGCTGT TTTGTGTCCG AAAGGTCCAC TTCGTATGCT GGTTGAAACA GCTCAGGAGA    1080
GAAATGAAAC GCTTTTTCCA GCTCTCATTT ACTCCTCAAC AATGGTGTGG TTGGTGAATA    1140
TGGCAGAAGG AGACCCGGAA GCTCAAAGGA GAGTATCCAA AAATTCCAAG TATAATGCAG    1200
AAAGCACAGA AAGGGAGTCA CAAGACACTG TTGCAGAGAA TGATGATGGC GGGTTCAGTG    1260
AGGAATGGGA AGCCCAGAGG GACAGTCATC TAGGGCCTCA TCGCTCTACA CCTGAGTCAC    1320
GAGCTGCTGT CCAGGAACTT TCCAGCAGTA TCCTCGCTGG TGAAGACCCA GAGGAAAGGG    1380
GAGTAAAACT TGGATTGGGA GATTTCATTT TCTACAGTGT TCTGGTTGGT AAAGCCTCAG    1440
CAACAGCCAG TGGAGACTGG AACACAACCA TAGCCTGTTT CGTAGCCATA TTAATTGGTT    1500
TGTGCCTTAC ATTATTACTC CTTGCCATTT TCAAGAAAGC ATTGCCAGCT CTTCCAATCT    1560
CCATCACCTT TGGGCTTGTT TTCTACTTTG CCACAGATTA TCTTGTACAG CCTTTTATGG    1620
ACCAATTAGC ATTCCATCAA TTTTATATCT AGCATATTTG CGGTTAGAAT CCCATGGATG    1680
TTTCTTCTTT GACTATAACC AAATCTGGGG AGGACAAAGG TGATTTTCCT GTGTCCACAT    1740
CTAACAAAGT CAAGATTCCC GGCTGGACTT TTGCAGCTTC CTTCCAAGTC TTCCTGACCA    1800
CCTTGCACTA TTGGACTTTG GAAGGAGGTG CCTATAGAAA ACGATTTTGA ACATACTTCA    1860
TCGCAGTGGA CTGTGTCCCT CGGTGCAGAA ACTACCAGAT TGAGGGACG AGGTCAAGGA     1920
GATATGATAG GCCCGGAAGT TGCTGTGCCC CATCAGCAGC TTGACGCGTG GTCACAGGAC    1980
GATTTCACTG ACACTGCGAA CTCTCAGGAC TACCGGTTAC AAGAGGTTA GGTGAAGTGG     2040
TTTAAACCAA ACGGAACTCT TCATCTTAAA CTACACGTTG AAAATCAACC CAATAATTCT    2100
```

-continued

```
GTATTAACTG AATTCTGAAC TTTTCAGGAG GTACTGTGAG GAAGAGCAGG CACCAGCAGC    2160

AGAATGGGGA ATGGAGAGGT GGGCAGGGGT TCCAGCTTCC CTTTGATTTT TTGCTGCAGA    2220

CTCATCCTTT TTAAATGAGA CTTGTTTTCC CCTCTCTTTG AGTCAAGTCA AATATGTAGA    2280

TTGCCTTTGG CAATTCTTCT TCTCAAGCAC TGACACTCAT TACCGTCTGT GATTGCCATT    2340

TCTTCCCAAG GCCAGTCTGA ACCTGAGGTT GCTTTATCCT AAAAGTTTTA ACCTCAGGTT    2400

CCAAATTCAG TAAATTTTGG AAACAGTACA GCTATTTCTC ATCAATTCTC TATCATGTTG    2460

AAGTCAAATT TGGATTTTCC ACCAAATTCT GAATTTGTAG ACATACTTGT ACGCTCACTT    2520

GCCCCCAGAT GCCTCCTCTG TCCTCATTCT TCTCTCCCAC ACAAGCAGTC TTTTTCTACA    2580

GCCAGTAAGG CAGCTCTGTC RTGGTAGCAG ATGGTCCCAT TATTCTAGGG TCTTACTCTT    2640

TGTATGATGA AAAGAATGTG TTATGAATCG GTGCTGTCAG CCCTGCTGTC AGACCTTCTT    2700

CCACAGCAAA TGAGATGTAT GCCCAAAGCG GTAGAATTAA AGAAGAGTAA AATGGCTGTT    2760

GAAG                                                                2764
```

(2) INFORMATION FOR SEQ ID NO:10:

(i) SEQUENCE CHARACTERISTICS:
        (A) LENGTH: 467 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:10:

```
Met Thr Glu Leu Pro Ala Pro Leu Ser Tyr Phe Gln Asn Ala Gln Met
 1               5                  10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190
```

-continued

```
Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
                260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
        290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
                340                 345                 350

Ser Thr Pro Glu Ser Arg Ala Ala Val Gln Glu Leu Ser Ser Ser Ile
        355                 360                 365

Leu Ala Gly Glu Asp Pro Glu Glu Arg Gly Val Lys Leu Gly Leu Gly
370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Ala Ile Phe Lys Lys Ala Leu
                420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
450                 455                 460

Phe Tyr Ile
465
```

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:11:

CGGAATTCCG TATGCTGGTT GAAACA                                    26

(2) INFORMATION FOR SEQ ID NO:12:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:12:

| | |
|---|---:|
| CGGGATCCTC AGGCTACGAA ACAGGCTAT | 29 |

(2) INFORMATION FOR SEQ ID NO:13:

(i) SEQUENCE CHARACTERISTICS:
    (A) LENGTH: 1854 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:13:

| | |
|---|---:|
| TATATCAGCG GTATGACCGA CCTCTATGCG TGGGATGAAT ACCGACGTCT GATGGCCGTA | 60 |
| GAACAATAAC CAGGCTTTTG TAAAGACGAA CAATAAATTT TTACCTTTTG CAGAAACTTT | 120 |
| AGTTCGGAAC TTCAGGCTAT AAAACGAATC TGAAGAACAC AGCAATTTTG CGTTATCTGT | 180 |
| TAATCGAGAC TGAAATACAT GAAAAAAACC ACATTAGCAC TGAGTCGACT GGCTCTGAGT | 240 |
| TTAGGTTTGG CGTTATCTCC GCTCTCTGCA ACGGCGGCTG AGACTTCTTC AGCAACGACA | 300 |
| GCCCAGCAGA TGCCAAGCCT TGCACCGATG CTCGAAAAGG TGATGCCTTC AGTGGTCAGC | 360 |
| ATTAACGTAG AAGGTAGCAC AACCGTTAAT ACGCCGCGTA TGCCGCGTAA TTTCCAGCAG | 420 |
| TTCTTCGGTG ATGATTCTCC GTTCTGCCAG GAAGGTTCTC CGTTCCAGAG CTCTCCGTTC | 480 |
| TGCCAGGGTG GCCAGGGCGG TAATGGTGGC GGCCAGCAAC AGAAATTCAT GGCGCTGGGT | 540 |
| TCCGGCGTCA TCATTGATGC CGATAAAGGC TATGTCGTCA CCAACAACCA CGTTGTTGAT | 600 |
| AACGCGACGG TCATTAAAGT TCAACTGAGC GATGGCCGTA AGTTCGACGC GAAGATGGTT | 660 |
| GGCAAAGATC CGCGCTCTGA TATCGCGCTG ATCCAAATCC AGAACCCGAA AAACCTGACC | 720 |
| GCAATTAAGA TGGCGGATTC TGATGCACTG CGCGTGGGTG ATTACACCGT AGGGATTGGT | 780 |
| AACCCGTTTG GTCTGGGCGA GACGGTAACT TCCGGGATTG TCTCTGCGCT GGGGCGTAGC | 840 |
| GGCCTGAATG CCGAAAACTA CGAAAACTTC ATCCAGACCG ATGCAGCGAT CAACCGTGGT | 900 |
| AACTCCGGTG GTGCGCTGGT TAACCTGAAC GGCGAACTGA TCGGTATCAA CACCGCGATC | 960 |
| CTCGCACCGG ACGGCGGCAA CATCGGTATC GGTTTTGCTA TCCCGAGTAA CATGGTGAAA | 1020 |
| AACCTGACCT CGCAGATGGT GGAATACGGC CAGGTGAAAC GCGGTGAGCT GGGTATTATG | 1080 |
| GGGACTGAGC TGAACTCCGA ACTGGCGAAA GCGATGAAAG TTGACGCCCA GCGCGGTGCT | 1140 |

-continued

```
TTCGTAAGCC AGGTTCTGCC TAATTCCTCC GCTGCAAAAG CGGGCATTAA AGCGGGTGAT    1200

GTGATCACCT CACTGAACGG TAAGCCGATC AGCAGCTTTG CCGCACTGCG TGCTCAGGTG    1260

GGTACTATGC CGGTAGGCAG CAAACTGACC CTGGGCTTAC TGCGCGACGG TAAGCAGGTT    1320

AACGTGAACC TGGAACTGCA GCAGAGCAGC CAGAATCAGG TTGATTCCAG CTCCATCTTC    1380

AACGGCATTG AAGGCGCTGA GATGAGCAAC AAAGGCAAAG ATCAGGGCGT GGTAGTGAAC    1440

AACGTGAAAA CGGGCACTCC GGCTGCGCAG ATCGGCCTGA AGAAAGGTGA TGTGATTATT    1500

GGCGCGAACC AGCAGGCAGT GAAAAACATC GCTGAACTGC GTAAAGTTCT CGACAGCAAA    1560

CCGTCTGTGC TGGCACTCAA CATTCAGCGC GGCGACCGCC ATCTACCTGT TAATGCAGTA    1620

ATCTCCCTCA ACCCCTTCCT GAAAACGGGA AGGGGTTCTC CTTACAATCT GTGAACTTCA    1680

CCACAACTCC ATACATCTTC ATCATCCTTT AGGCATTTGC ACAATGCCGT ACGTTACGTA    1740

CTTCCTTATG CTAAGCCGTG CATAACGGAG GACTTATGGC TGGCTGGCAT CTTGATACCA    1800

AAATGGCGCA GGATATCGTG GCACGTACCA TGCGCATCAT CGATACCAAT ATCA          1854
```

(2) INFORMATION FOR SEQ ID NO:14:

(i) SEQUENCE CHARACTERISTICS:
        (A) LENGTH: 491 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:14:

```
Met Lys Lys Thr Thr Leu Ala Leu Ser Arg Leu Ala Leu Ser Leu Gly
  1               5                  10                  15

Leu Ala Leu Ser Pro Leu Ser Ala Thr Ala Ala Glu Thr Ser Ser Ala
                 20                  25                  30

Thr Thr Ala Gln Gln Met Pro Ser Leu Ala Pro Met Leu Glu Lys Val
             35                  40                  45

Met Pro Ser Val Val Ser Ile Asn Val Glu Gly Ser Thr Thr Val Asn
         50                  55                  60

Thr Pro Arg Met Pro Arg Asn Phe Gln Gln Phe Phe Gly Asp Asp Ser
 65                  70                  75                  80

Pro Phe Cys Gln Glu Gly Ser Pro Phe Gln Ser Pro Phe Cys Gln
                 85                  90                  95

Gly Gly Gln Gly Gly Asn Gly Gly Gln Gln Gln Lys Phe Met Ala
                100                 105                 110

Leu Gly Ser Gly Val Ile Ile Asp Ala Asp Lys Gly Tyr Val Val Thr
            115                 120                 125

Asn Asn His Val Val Asp Asn Ala Thr Val Ile Lys Val Gln Leu Ser
        130                 135                 140

Asp Gly Arg Lys Phe Asp Ala Lys Met Val Gly Lys Asp Pro Arg Ser
145                 150                 155                 160

Asp Ile Ala Leu Ile Gln Ile Gln Asn Pro Lys Asn Leu Thr Ala Ile
                165                 170                 175

Lys Met Ala Asp Ser Asp Ala Leu Arg Val Gly Asp Tyr Thr Val Gly
                180                 185                 190
```

```
Ile Gly Asn Pro Phe Gly Leu Gly Glu Thr Val Thr Ser Gly Ile Val
        195                 200                 205

Ser Ala Leu Gly Arg Ser Gly Leu Asn Ala Glu Asn Tyr Glu Asn Phe
210                 215                 220

Ile Gln Thr Asp Ala Ala Ile Asn Arg Gly Asn Ser Gly Gly Ala Leu
225                 230                 235                 240

Val Asn Leu Asn Gly Glu Leu Ile Gly Ile Asn Thr Ala Ile Leu Ala
                245                 250                 255

Pro Asp Gly Gly Asn Ile Gly Ile Gly Phe Ala Ile Pro Ser Asn Met
            260                 265                 270

Val Lys Asn Leu Thr Ser Gln Met Val Glu Tyr Gly Gln Val Lys Arg
        275                 280                 285

Gly Glu Leu Gly Ile Met Gly Thr Glu Leu Asn Ser Glu Leu Ala Lys
        290                 295                 300

Ala Met Lys Val Asp Ala Gln Arg Gly Ala Phe Val Ser Gln Val Leu
305                 310                 315                 320

Pro Asn Ser Ser Ala Ala Lys Ala Gly Ile Lys Ala Gly Asp Val Ile
                325                 330                 335

Thr Ser Leu Asn Gly Lys Pro Ile Ser Ser Phe Ala Ala Leu Arg Ala
            340                 345                 350

Gln Val Gly Thr Met Pro Val Gly Ser Lys Leu Thr Leu Gly Leu Leu
        355                 360                 365

Arg Asp Gly Lys Gln Val Asn Val Asn Leu Glu Leu Gln Gln Ser Ser
370                 375                 380

Gln Asn Gln Val Asp Ser Ser Ile Phe Asn Gly Ile Glu Gly Ala
385                 390                 395                 400

Glu Met Ser Asn Lys Gly Lys Asp Gln Gly Val Val Asn Asn Val
                405                 410                 415

Lys Thr Gly Thr Pro Ala Ala Gln Ile Gly Leu Lys Lys Gly Asp Val
            420                 425                 430

Ile Ile Gly Ala Asn Gln Gln Ala Val Lys Asn Ile Ala Glu Leu Arg
            435                 440                 445

Lys Val Leu Asp Ser Lys Pro Ser Val Leu Ala Leu Asn Ile Gln Arg
        450                 455                 460

Gly Asp Arg His Leu Pro Val Asn Ala Val Ile Ser Leu Asn Pro Phe
465                 470                 475                 480

Leu Lys Thr Gly Arg Gly Ser Pro Tyr Asn Leu
            485                 490
```

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:15:

CTGGATGGGG AGGTGATTGG AGTG                          24

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:16:

```
GTCTCTGGGC CCCGGTTGTC TGTTG                                          25
```

(2) INFORMATION FOR SEQ ID NO:17:

(i) SEQUENCE CHARACTERISTICS:
        (A) LENGTH: 2036 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:
        Feature polymorphism at 1325

(xi) SEQUENCE DESCRIPTION: SEQ ID NO:17:

```
CCGGCCCTCG CCCTGTCCGC CGCCACCGCC GCCGCCGCCA GAGTCGCCAT GCAGATCCCG    60
CGCGCCGCTC TTCTCCCGCT GCTGCTGCTG CTGCTGGCGG CGCCCGCCTC GGCGCAGCTG   120
TCCCGGGCCG GCCGCTCGGC GCCTTTGGCC GCCGGGTGCC CAGACCGCTG CGAGCCGGCG   180
CGCTGCCCGC CGCAGCCGGA GCACTGCGAG GGCGGCCGGG CCCGGGACGC GTGCGGCTGC   240
TGCGAGGTGT GCGGCGCGCC CGAGGGCGCC GCGTGCGGCC TGCAGGAGGG CCCGTGCGGC   300
GAGGGGCTGC AGTGCGTGGT GCCCTTCGGG GTGCCAGCCT CGGCCACGGT GCGGCGGCGC   360
GCGCAGGCCG GCCTCTGTGT GTGCGCCAGC AGCGAGCCGG TGTGCGGCAG CGACGCCAAC   420
ACCTACGCCA ACCTGTGCCA GCTGCGCGCC GCCAGCCGCC GCTCCGAGAG GCTGCACCGG   480
CCGCCGGTCA TCGTCCTGCA GCGCGGAGCC TGCGGCCAAG GGCAGGAAGA TCCCAACAGT   540
TTGCGCCATA AATATAACTT TATCGCGGAC GTGGTGGAGA AGATCGCCCC TGCCGTGGTT   600
CATATCGAAT TGTTTCGCAA GCTTCCGTTT TCTAAACGAG AGGTGCCGGT GGCTAGTGGG   660
TCTGGGTTTA TTGTGTCGGA AGATGGACTG ATCGTGACAA ATGCCCACGT GGTGACCAAC   720
AAGCACCGGG TCAAAGTTGA GCTGAAGAAC GGTGCCACTT ACGAAGCCAA AATCAAGGAT   780
GTGGATGAGA AAGCAGACAT CGCACTCATC AAAATTGACC ACCAGGGCAA GCTGCCTGTC   840
CTGCTGCTTG GCCGCTCCTC AGAGCTGCGG CCGGGAGAGT TCGTGGTCGC CATCGGAAGC   900
CCGTTTTCCC TTCAAAACAC AGTCACCACC GGGATCGTGA GCACCACCCA GCGAGGCGGC   960
AAAGAGCTGG GGCTCCGCAA CTCAGACATG GACTACATCC AGACCGACGC CATCATCAAC  1020
```

-continued

```
TATGGAAACT CGGGAGGCCC GTTAGTAAAC CTGGACGGTG AAGTGATTGG AATTAACACT    1080

TTGAAAGTGA CAGCTGGAAT CTCCTTTGCA ATCCCATCTG ATAAGATTAA AAAGTTCCTC    1140

ACGGAGTCCC ATGACCGACA GGCCAAAGGA AAAGCCATCA CCAAGAAGAA GTATATTGGT    1200

ATCCGAATGA TGTCACTCAC GTCCAGCAAA GCCAAAGAGC TGAAGGACCG GCACCGGGAC    1260

TTCCCAGACG TGATCTCAGG AGCGTATATA ATTGAAGTAA TTCCTGATAC CCAGCAGAA     1320

GCTGKTGGTC TCAAGGAAAA CGACGTCATA ATCAGCATCA ATGGACAGTC CGTGGTCTCC    1380

GCCAATGATG TCAGCGACGT CATTAAAAGG GAAAGCACCC TGAACATGGT GGTCCGCAGG    1440

GGTAATGAAG ATATCATGAT CACAGTGATT CCCGAAGAAA TTGACCCATA GGCAGAGGCA    1500

TGAGCTGGAC TTCATGTTTC CCTCAAAGAC TCTCCCGTGG ATGACGGATG AGGACTCTGG    1560

GCTGCTGGAA TAGGACACTC AAGACTTTTG ACTGCCATTT TGTTTGTTCA GTGGAGACTC    1620

CCTGGCCAAC AGAATCCTTC TTGATAGTTT GCAGGCAAAA CAAATGTAAT GTTGCAGATC    1680

CGCAGGCAGA AGCTCTGCCC TTCTGTATCC TATGTATGCA GTGTGCTTTT TCTTGCCAGC    1740

TTGGGCCATT CTTGCTTAGA CAGTCAGCAT TTGTCTCCTC CTTTAACTGA GTCATCATCT    1800

TAGTCCAACT AATGCAGTCG ATACAATGCG TAGATAGAAG AAGCCCCACG GGAGCCAGGA    1860

TGGGACTGGT CGTGTTTGTG CTTTTCTCCA AGTCAGCACC CAAAGGTCAA TGCACAGAGA    1920

CCCCGGGTGG GTGAGCGCTG GCTTCTCAAA CGGCCGAAGT TGCCTCTTTT AGGAATCTCT    1980

TTGGAATTGG GAGCACGATG ACTCTGAGTT TGAGCTATTA AAGTACTTCT TACAAA        2036
```

(2) INFORMATION FOR SEQ ID NO:18:

(i) SEQUENCE CHARACTERISTICS:
        (A) LENGTH: 480 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        Feature - 213 Gly/val polymorph (xi) SEQUENCE DESCRIPTION: SEQ ID NO:18:

```
Met Gln Ile Pro Arg Ala Ala Leu Leu Pro Leu Leu Leu Leu Leu
 1               5                  10                  15

Ala Ala Pro Ala Ser Ala Gln Leu Ser Arg Ala Gly Arg Ser Ala Pro
            20                  25                  30

Leu Ala Ala Gly Cys Pro Asp Arg Cys Glu Pro Ala Arg Cys Pro Pro
         35                  40                  45

Gln Pro Glu His Cys Glu Gly Gly Arg Ala Arg Asp Ala Cys Gly Cys
     50                  55                  60

Cys Glu Val Cys Gly Ala Pro Glu Gly Ala Ala Cys Gly Leu Gln Glu
 65                  70                  75                  80

Gly Pro Cys Gly Glu Gly Leu Gln Cys Val Val Pro Phe Gly Val Pro
                 85                  90                  95

Ala Ser Ala Thr Val Arg Arg Arg Ala Gln Ala Gly Leu Cys Val Cys
            100                 105                 110

Ala Ser Ser Glu Pro Val Cys Gly Ser Asp Ala Asn Thr Tyr Ala Asn
        115                 120                 125
```

```
Leu Cys Gln Leu Arg Ala Ala Ser Arg Arg Ser Glu Arg Leu His Arg
        130                 135                 140

Pro Pro Val Ile Val Leu Gln Arg Gly Ala Cys Gly Gln Gly Gln Glu
145                 150                 155                 160

Asp Pro Asn Ser Leu Arg His Lys Tyr Asn Phe Ile Ala Asp Val Val
                165                 170                 175

Glu Lys Ile Ala Pro Ala Val Val His Ile Glu Leu Phe Arg Lys Leu
            180                 185                 190

Pro Phe Ser Lys Arg Glu Val Pro Val Ala Ser Gly Ser Gly Phe Ile
        195                 200                 205

Val Ser Glu Asp Xaa Leu Ile Val Thr Asn Ala His Val Val Thr Asn
    210                 215                 220

Lys His Arg Val Lys Val Glu Leu Lys Asn Gly Ala Thr Tyr Glu Ala
225                 230                 235                 240

Lys Ile Lys Asp Val Asp Glu Lys Ala Asp Ile Ala Leu Ile Lys Ile
                245                 250                 255

Asp His Gln Gly Lys Leu Pro Val Leu Leu Leu Gly Arg Ser Ser Glu
            260                 265                 270

Leu Arg Pro Gly Glu Phe Val Val Ala Ile Gly Ser Pro Phe Ser Leu
        275                 280                 285

Gln Asn Thr Val Thr Thr Gly Ile Val Ser Thr Thr Gln Arg Gly Gly
    290                 295                 300

Lys Glu Leu Gly Leu Arg Asn Ser Asp Met Asp Tyr Ile Gln Thr Asp
305                 310                 315                 320

Ala Ile Ile Asn Tyr Gly Asn Ser Gly Gly Pro Leu Val Asn Leu Asp
                325                 330                 335

Gly Glu Val Ile Gly Ile Asn Thr Leu Lys Val Thr Ala Gly Ile Ser
            340                 345                 350

Phe Ala Ile Pro Ser Asp Lys Ile Lys Lys Phe Leu Thr Glu Ser His
        355                 360                 365

Asp Arg Gln Ala Lys Gly Lys Ala Ile Thr Lys Lys Lys Tyr Ile Gly
    370                 375                 380

Ile Arg Met Met Ser Leu Thr Ser Ser Lys Ala Lys Glu Leu Lys Asp
385                 390                 395                 400

Arg His Arg Asp Phe Pro Asp Val Ile Ser Gly Ala Tyr Ile Ile Glu
                405                 410                 415

Val Ile Pro Asp Thr Pro Ala Glu Ala Gly Gly Leu Lys Glu Asn Asp
            420                 425                 430

Val Ile Ile Ser Ile Asn Gly Gln Ser Val Val Ser Ala Asn Asp Val
        435                 440                 445

Ser Asp Val Ile Lys Arg Glu Ser Thr Leu Asn Met Val Val Arg Arg
    450                 455                 460

Gly Asn Glu Asp Ile Met Ile Thr Val Ile Pro Glu Glu Ile Asp Pro
465                 470                 475                 480

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO
```

(v) FRAGMENT TYPE:

(vi) ORIGINAL SOURCE:

(xi) SEQUENCE DESCRIPTION: SEQ ID NO:19:

ATGCTGAACA TCGGGAAAGC TTGGTTCTCG                                              30

(2) INFORMATION FOR SEQ ID NO:20:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:20:

CCAACAGACA ACCGGGCCCA GAGACT                                                  26

(2) INFORMATION FOR SEQ ID NO:21:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:21:

TGCCTCCTCG CCCGCCCTAC TCAGA                                                   25

(2) INFORMATION FOR SEQ ID NO:22:

(i) SEQUENCE CHARACTERISTICS:
            (A) LENGTH: 587 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:22:

CGTGGATCCC GAGAAAGAGG CGCAGGACGA GGAGGCAGAA CCCGACTGGC GCGTAGAGCA             60

GCAGCACGAG CAGTAGGAAG CAGTCACCCG GAAGCCTGGG GGCGAGAGGC GAAGTGGTCA            120

-continued

```
GGCGCCGAAG GCCGAGAGCA CGCGGGGATC GGTCTCTTCC CGCCGGGTCT CTTACCGGTG      180

CGAGTCAAAG AGCCGCTCCG GCCCCGGCCC TGAGGGAAGC TCCATAACTG CTGCTTCAGG      240

AGCGCCCGGC CGTCGCCGCC GCCGCCATTT TCGCGCCCGG CCGCAGGGGC TCTTGGGAAG      300

GCGGAGTCTT TGGGCATCCG CCCGGGGTGA GGGGACCCGA AGTCCTGAGG CGCGCCGGAA      360

GGGCTAGCGG TCCCAGCATA CCCCGCGGCC CCTTGGGCCG TCTCACAACT CGCGTCCGGC      420

GGAGACCACA ATTCCCGGCA TTCGTGGGGC AGGGAGGAGT CGGCCTCCCG GAATCCTGGT      480

CCCGGCGTGC ACTTCTGAAG GACTTCAGGT ACCGGCGTGC CCCGCGTCCT ACTGTCCGCC      540

TGCTCGCGTC CTGGGTGCCG CCTCTGAGTA GGGCGGGCGA GGAGGCA                   587
```

(2) INFORMATION FOR SEQ ID NO:23:

(i) SEQUENCE CHARACTERISTICS:
        (A) LENGTH: 2187 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 603...1976
        (D) OTHER INFORMATION:

(xi) SEQUENCE DESCRIPTION: SEQ ID NO:23:

```
CGTGGATCCC GAGAAAGAGG CGCAGGACGA GGAGGCAGAA CCCGACTGGC GCGTAGAGCA       60

GCAGCACGAG CAGTAGGAAG CAGTCACCCG GAAGCCTGGG GGCGAGAGGC GAAGTGGTCA      120

GGCGCCGAAG GCCGAGAGCA CGCGGGGATC GGTCTCTTCC CGCCGGGTCT CTTACCGGTG      180

CGAGTCAAAG AGCCGCTCCG GCCCCGGCCC TGAGGGAAGC TCCATAACTG CTGCTTCAGG      240

AGCGCCCGGC CGTCGCCGCC GCCGCCATTT TCGCGCCCGG CCGCAGGGGC TCTTGGGAAG      300

GCGGAGTCTT TGGGCATCCG CCCGGGGTGA GGGGACCCGA AGTCCTGAGG CGCGCCGGAA      360

GGGCTAGCGG TCCCAGCATA CCCCGCGGCC CCTTGGGCCG TCTCACAACT CGCGTCCGGC      420

GGAGACCACA ATTCCCGGCA TTCGTGGGGC AGGGAGGAGT CGGCCTCCCG GAATCCTGGT      480

CCCGGCGTGC ACTTCTGAAG GACTTCAGGT ACCGGCGTGC CCCGCGTCCT ACTGTCCGCC      540

TGCTCGCGTC CTGGGTGCCG CCTCTGAGTA GGGCGGGCGA GGAGGCAGCC AAGGCGGAGC      600

TG ATG GCT GCG CCG AGG GCG GGG CGG GGT GCA GGC TGG AGC CTT CGG        647
   Met Ala Ala Pro Arg Ala Gly Arg Gly Ala Gly Trp Ser Leu Arg
    1               5                  10                  15

GCA TGG CGG GCT TTG GGG GGC ATT TGC TGG GGG AGG AGA CCC CGT TTG        695
Ala Trp Arg Ala Leu Gly Gly Ile Cys Trp Gly Arg Arg Pro Arg Leu
                20                  25                  30

ACC CCT GAC CTC CGG GCC CTG CTG ACG TCA GGA ACT TCT GAC CCC CGG        743
Thr Pro Asp Leu Arg Ala Leu Leu Thr Ser Gly Thr Ser Asp Pro Arg
                35                  40                  45

GCC CGA GTG ACT TAT GGG ACC CCC AGT CTC TGG GCC CGG TTG TCT GTT        791
Ala Arg Val Thr Tyr Gly Thr Pro Ser Leu Trp Ala Arg Leu Ser Val
            50                  55                  60
```

| | | |
|---|---|---|
| GGG GTC ACT GAA CCC CGA GCA TGC CTG ACG TCT GGG ACC CCG GGT CCC<br>Gly Val Thr Glu Pro Arg Ala Cys Leu Thr Ser Gly Thr Pro Gly Pro<br>65                            70                      75 | 839 |
| CGG GCA CAA CTG ACT GCG GTG ACC CCA GAT ACC AGG ACC CGG GAG GCC<br>Arg Ala Gln Leu Thr Ala Val Thr Pro Asp Thr Arg Thr Arg Glu Ala<br>80                            85                      90                      95 | 887 |
| TCA GAG AAC TCT GGA ACC CGT TCG CGC GCG TGG CTG GCG GTG GCG CTG<br>Ser Glu Asn Ser Gly Thr Arg Ser Arg Ala Trp Leu Ala Val Ala Leu<br>                  100                     105                  110 | 935 |
| GGC GCT GGG GGG GCA GTG CTG TTG TTG TTG TGG GGC GGG GGT CGG GGT<br>Gly Ala Gly Gly Ala Val Leu Leu Leu Leu Trp Gly Gly Gly Arg Gly<br>        115                     120                    125 | 983 |
| CCT CCG GCC GTC CTC GCC GCC GTC CCT AGC CCG CCG CCC GCT TCT CCC<br>Pro Pro Ala Val Leu Ala Ala Val Pro Ser Pro Pro Pro Ala Ser Pro<br>           130                     135                    140 | 1031 |
| CGG AGT CAG TAC AAC TTC ATC GCA GAT GTG GTG GAG AAG ACA GCA CCT<br>Arg Ser Gln Tyr Asn Phe Ile Ala Asp Val Val Glu Lys Thr Ala Pro<br>145                          150                     155 | 1079 |
| GCC GTG GTC TAT ATC GAG ATC CTG GAC CGG CAC CCT TTC TTG GGC CGC<br>Ala Val Val Tyr Ile Glu Ile Leu Asp Arg His Pro Phe Leu Gly Arg<br>160                          165                     170                175 | 1127 |
| GAG GTC CCT ATC TCG AAC GGC TCA GGA TTC GTG GTG GCT GCC GAT GGG<br>Glu Val Pro Ile Ser Asn Gly Ser Gly Phe Val Val Ala Ala Asp Gly<br>                  180                     185                    190 | 1175 |
| CTC ATT GTC ACC AAC GCC CAT GTG GTG GCT GAT CGG CGC AGA GTC CGT<br>Leu Ile Val Thr Asn Ala His Val Val Ala Asp Arg Arg Arg Val Arg<br>        195                     200                    205 | 1223 |
| GTG AGA CTG CTA AGC GGC GAC ACG TAT GAG GCC GTG GTC ACA GCT GTG<br>Val Arg Leu Leu Ser Gly Asp Thr Tyr Glu Ala Val Val Thr Ala Val<br>           210                     215                    220 | 1271 |
| GAT CCC GTG GCA GAC ATC GCA ACG CTG AGG ATT CAG ACT AAG GAG CCT<br>Asp Pro Val Ala Asp Ile Ala Thr Leu Arg Ile Gln Thr Lys Glu Pro<br>225                          230                     235 | 1319 |
| CTC CCC ACG CTG CCT CTG GGA CGC TCA GCT GAT GTC CGG CAA GGG GAG<br>Leu Pro Thr Leu Pro Leu Gly Arg Ser Ala Asp Val Arg Gln Gly Glu<br>240                          245                     250                255 | 1367 |
| TTT GTT GTT GCC ATG GGA AGT CCC TTT GCA CTG CAG AAC ACG ATC ACA<br>Phe Val Val Ala Met Gly Ser Pro Phe Ala Leu Gln Asn Thr Ile Thr<br>           260                     265                    270 | 1415 |
| TCC GGC ATT GTT AGC TCT GCT CAG CGT CCA GCC AGA GAC CTG GGA CTC<br>Ser Gly Ile Val Ser Ser Ala Gln Arg Pro Ala Arg Asp Leu Gly Leu<br>        275                     280                    285 | 1463 |
| CCC CAA ACC AAT GTG GAA TAC ATT CAA ACT GAT GCA GCT ATT GAT TTT<br>Pro Gln Thr Asn Val Glu Tyr Ile Gln Thr Asp Ala Ala Ile Asp Phe<br>           290                     295                    300 | 1511 |
| GGA AAC TCT GGA GGT CCC CTG GTT AAC CTG GAT GGG GAG GTG ATT GGA<br>Gly Asn Ser Gly Gly Pro Leu Val Asn Leu Asp Gly Glu Val Ile Gly<br>        305                     310                    315 | 1559 |
| GTG AAC ACC ATG AAG GTC ACA GCT GGA ATC TCC TTT GCC ATC CCT TCT<br>Val Asn Thr Met Lys Val Thr Ala Gly Ile Ser Phe Ala Ile Pro Ser<br>320                          325                     330                335 | 1607 |
| GAT CGT CTT CGA GAG TTT CTG CAT CGT GGG GAA AAG AAG AAT TCC TCC<br>Asp Arg Leu Arg Glu Phe Leu His Arg Gly Glu Lys Lys Asn Ser Ser<br>           340                     345                    350 | 1655 |
| TCC GGA ATC AGT GGG TCC CAG CGG CGC TAC ATT GGG GTG ATG ATG CTG<br>Ser Gly Ile Ser Gly Ser Gln Arg Arg Tyr Ile Gly Val Met Met Leu<br>        355                     360                    365 | 1703 |
| ACC CTG AGT CCC AGC ATC CTT GCT GAA CTA CAG CTT CGA GAA CCA AGC<br>Thr Leu Ser Pro Ser Ile Leu Ala Glu Leu Gln Leu Arg Glu Pro Ser<br>           370                     375                    380 | 1751 |

| | | | | | | | | | | | | | | | | |
|---|---|---|---|---|---|---|---|---|---|---|---|---|---|---|---|---|
|TTT|CCC|GAT|GTT|CAG|CAT|GGT|GTA|CTC|ATC|CAT|AAA|GTC|ATC|CTG|GGC|1799|
|Phe|Pro|Asp|Val|Gln|His|Gly|Val|Leu|Ile|His|Lys|Val|Ile|Leu|Gly| |
| |385| | | | |390| | | | |395| | | | | |

| | | | | | | | | | | | | | | | | |
|---|---|---|---|---|---|---|---|---|---|---|---|---|---|---|---|---|
|TCC|CCT|GCA|CAC|CGG|GCT|GGT|CTG|CGG|CCT|GGT|GAT|GTG|ATT|TTG|GCC|1847|
|Ser|Pro|Ala|His|Arg|Ala|Gly|Leu|Arg|Pro|Gly|Asp|Val|Ile|Leu|Ala| |
|400| | | | |405| | | | |410| | | | |415| |

| | | | | | | | | | | | | | | | | |
|---|---|---|---|---|---|---|---|---|---|---|---|---|---|---|---|---|
|ATT|GGG|GAG|CAG|ATG|GTA|CAA|AAT|GCT|GAA|GAT|GTT|TAT|GAA|GCT|GTT|1895|
|Ile|Gly|Glu|Gln|Met|Val|Gln|Asn|Ala|Glu|Asp|Val|Tyr|Glu|Ala|Val| |
| | | | |420| | | | |425| | | | |430| | |

| | | | | | | | | | | | | | | | | |
|---|---|---|---|---|---|---|---|---|---|---|---|---|---|---|---|---|
|CGA|ACC|CAA|TCC|CAG|TTG|GCA|GTG|CAG|ATC|CGG|CGG|GGA|CGA|GAA|ACA|1943|
|Arg|Thr|Gln|Ser|Gln|Leu|Ala|Val|Gln|Ile|Arg|Arg|Gly|Arg|Glu|Thr| |
| | | |435| | | | |440| | | | |445| | | |

| | | | | | | | | | | |
|---|---|---|---|---|---|---|---|---|---|---|
|CTG|ACC|TTA|TAT|GTG|ACC|CCT|GAG|GTC|ACA|GAA|TGAATAGATC ACCAAGAGTA|1996|
|Leu|Thr|Leu|Tyr|Val|Thr|Pro|Glu|Val|Thr|Glu| |
| | |450| | | | |455| | | | |

```
TGAGGCTCCT GCTCTGATTT CCTCCTTGCC TTTCTGGCTG AGGTTCTGAG GGCACCGAGA    2056

CAGAGGGTTA AATGAACCAG TGGGGGCAGG TCCCTCCAAC CACCAGCACT GACTCCTGGG    2116

CTCTGAAGAA TCACAGAAAC ACTTTTTATA TAAAATAAAA TTATACCTAG CAACATAAAA    2176

AAAAAAAAA A                                                          2187
```

(2) INFORMATION FOR SEQ ID NO:24:

(i) SEQUENCE CHARACTERISTICS:
        (A) LENGTH: 2187 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 603...1976
        (D) OTHER INFORMATION:

(xi) SEQUENCE DESCRIPTION: SEQ ID NO:24:

```
CGTGGATCCC GAGAAAGAGG CGCAGGACGA GGAGGCAGAA CCCGACTGGC GCGTAGAGCA     60

GCAGCACGAG CAGTAGGAAG CAGTCACCCG GAAGCCTGGG GGCGAGAGGC GAAGTGGTCA    120

GGCGCCGAAG GCCGAGAGCA CGCGGGGATC GGTCTCTTCC CGCCGGGTCT CTTACCGGTG    180

CGAGTCAAAG AGCCGCTCCG GCCCCGGCCC TGAGGGAAGC TCCATAACTG CTGCTTCAGG    240

AGCGCCCGGC CGTCGCCGCC GCCGCCATTT TCGCGCCCGG CCGCAGGGGC TCTTGGGAAG    300

GCGGAGTCTT TGGGCATCCG CCCGGGGTGA GGGGACCCGA AGTCCTGAGG CGCGCCGGAA    360

GGGCTAGCGG TCCAGCATA  CCCCGCGGCC CCTTGGGCCG TCTCACAACT CGCGTCCGGC    420

GGAGACCACA ATTCCCGGCA TTCGTGGGGC AGGGAGGAGT CGGCCTCCCG GAATCCTGGT    480

CCCGGCGTGC ACTTCTGAAG GACTTCAGGT ACCGGCGTGC CCCGCGTCCT ACTGTCCGCC    540

TGCTCGCGTC CTGGGTGCCG CCTCTGAGTA GGGCGGGCGA GGAGGCAGCC AAGGCGGAGC    600
```

| | | | | | | | | | | | | | |
|---|---|---|---|---|---|---|---|---|---|---|---|---|---|
|TG|ATG|GCT|GCG|CCG|AGG|GCG|GGG|CGG|GGT|GCA|GGC|TGG AGC CTT CGG|647|
| |Met|Ala|Ala|Pro|Arg|Ala|Gly|Arg|Gly|Ala|Gly|Trp Ser Leu Arg| |
| |1| | | |5| | | | |10| | 15| |

| | | |
|---|---|---|
| GCA TGG CGG GCT TTG GGG GGC ATT CGC TGG GGG AGG AGA CCC CGT TTG<br>Ala Trp Arg Ala Leu Gly Gly Ile Arg Trp Gly Arg Arg Pro Arg Leu<br>              20                    25                    30 | 695 |
| ACC CCT GAC CTC CGG GCC CTG CTG ACG TCA GGA ACT TCT GAC CCC CGG<br>Thr Pro Asp Leu Arg Ala Leu Leu Thr Ser Gly Thr Ser Asp Pro Arg<br>              35                    40                    45 | 743 |
| GCC CGA GTG ACT TAT GGG ACC CCC AGT CTC TGG GCC CGG TTG TCT GTT<br>Ala Arg Val Thr Tyr Gly Thr Pro Ser Leu Trp Ala Arg Leu Ser Val<br>            50                    55                    60 | 791 |
| GGG GTC ACT GAA CCC CGA GCA TGC CTG ACG TCT GGG ACC CCG GGT CCC<br>Gly Val Thr Glu Pro Arg Ala Cys Leu Thr Ser Gly Thr Pro Gly Pro<br>65                    70                    75 | 839 |
| CGG GCA CAA CTG ACT GCG GTG ACC CCA GAT ACC AGG ACC CGG GAG GCC<br>Arg Ala Gln Leu Thr Ala Val Thr Pro Asp Thr Arg Thr Arg Glu Ala<br>80                    85                    90                    95 | 887 |
| TCA GAG AAC TCT GGA ACC CGT TCG CGC GCG TGG CTG GCG GTG GCG CTG<br>Ser Glu Asn Ser Gly Thr Arg Ser Arg Ala Trp Leu Ala Val Ala Leu<br>                    100                  105                110 | 935 |
| GGC GCT GGG GGG GCA GTG CTG TTG TTG TGG GGC GGG GGT CGG GGT<br>Gly Ala Gly Gly Ala Val Leu Leu Leu Trp Gly Gly Gly Arg Gly<br>              115                  120                125 | 983 |
| CCT CCG GCC GTC CTC GCC GCC GTC CCT AGC CCG CCG CCC GCT TCT CCC<br>Pro Pro Ala Val Leu Ala Ala Val Pro Ser Pro Pro Pro Ala Ser Pro<br>            130                  135                140 | 1031 |
| CGG AGT CAG TAC AAC TTC ATC GCA GAT GTG GTG GAG AAG ACA GCA CCT<br>Arg Ser Gln Tyr Asn Phe Ile Ala Asp Val Val Glu Lys Thr Ala Pro<br>            145                  150                155 | 1079 |
| GCC GTG GTC TAT ATC GAG ATC CTG GAC CGG CAC CCT TTC TTG GGC CGC<br>Ala Val Val Tyr Ile Glu Ile Leu Asp Arg His Pro Phe Leu Gly Arg<br>160                    165                  170                175 | 1127 |
| GAG GTC CCT ATC TCG AAC GGC TCA GGA TTC GTG GTG GCT GCC GAT GGG<br>Glu Val Pro Ile Ser Asn Gly Ser Gly Phe Val Val Ala Ala Asp Gly<br>                    180                  185                190 | 1175 |
| CTC ATT GTC ACC AAC GCC CAT GTG GTG GCT GAT CGG CGC AGA GTC CGT<br>Leu Ile Val Thr Asn Ala His Val Val Ala Asp Arg Arg Arg Val Arg<br>                    195                  200                205 | 1223 |
| GTG AGA CTG CTA AGC GGC GAC ACG TAT GAG GCC GTG GTC ACA GCT GTG<br>Val Arg Leu Leu Ser Gly Asp Thr Tyr Glu Ala Val Val Thr Ala Val<br>            210                  215                220 | 1271 |
| GAT CCC GTG GCA GAC ATC GCA ACG CTG AGG ATT CAG ACT AAG GAG CCT<br>Asp Pro Val Ala Asp Ile Ala Thr Leu Arg Ile Gln Thr Lys Glu Pro<br>225                    230                  235 | 1319 |
| CTC CCC ACG CTG CCT CTG GGA CGC TCA GCT GAT GTC CGG CAA GGG GAG<br>Leu Pro Thr Leu Pro Leu Gly Arg Ser Ala Asp Val Arg Gln Gly Glu<br>240                    245                  250                255 | 1367 |
| TTT GTT GTT GCC ATG GGA AGT CCC TTT GCA CTG CAG AAC ACG ATC ACA<br>Phe Val Val Ala Met Gly Ser Pro Phe Ala Leu Gln Asn Thr Ile Thr<br>                    260                  265                270 | 1415 |
| TCC GGC ATT GTT AGC TCT GCT CAG CGT CCA GCC AGA GAC CTG GGA CTC<br>Ser Gly Ile Val Ser Ser Ala Gln Arg Pro Ala Arg Asp Leu Gly Leu<br>            275                  280                285 | 1463 |
| CCC CAA ACC AAT GTG GAA TAC ATT CAA ACT GAT GCA GCT ATT GAT TTT<br>Pro Gln Thr Asn Val Glu Tyr Ile Gln Thr Asp Ala Ala Ile Asp Phe<br>                    290                  295                300 | 1511 |
| GGA AAC TCT GGA GGT CCC CTG GTT AAC CTG GAT GGG GAG GTG ATT GGA<br>Gly Asn Ser Gly Gly Pro Leu Val Asn Leu Asp Gly Glu Val Ile Gly<br>            305                  310                315 | 1559 |
| GTG AAC ACC ATG AAG GTC ACA GCT GGA ATC TCC TTT GCC ATC CCT TCT<br>Val Asn Thr Met Lys Val Thr Ala Gly Ile Ser Phe Ala Ile Pro Ser<br>320                    325                  330                335 | 1607 |

```
GAT CGT CTT CGA GAG TTT CTG CAT CGT GGG GAA AAG AAG AAT TCC TCC      1655
Asp Arg Leu Arg Glu Phe Leu His Arg Gly Glu Lys Lys Asn Ser Ser
            340                 345                 350

TCC GGA ATC AGT GGG TCC CAG CGG CGC TAC ATT GGG GTG ATG ATG CTG      1703
Ser Gly Ile Ser Gly Ser Gln Arg Arg Tyr Ile Gly Val Met Met Leu
            355                 360                 365

ACC CTG AGT CCC AGC ATC CTT GCT GAA CTA CAG CTT CGA GAA CCA AGC      1751
Thr Leu Ser Pro Ser Ile Leu Ala Glu Leu Gln Leu Arg Glu Pro Ser
            370                 375                 380

TTT CCC GAT GTT CAG CAT GGT GTA CTC ATC CAT AAA GTC ATC CTG GGC      1799
Phe Pro Asp Val Gln His Gly Val Leu Ile His Lys Val Ile Leu Gly
385                 390                 395

TCC CCT GCA CAC CGG GCT GGT CTG CGG CCT GGT GAT GTG ATT TTG GCC      1847
Ser Pro Ala His Arg Ala Gly Leu Arg Pro Gly Asp Val Ile Leu Ala
400                 405                 410                 415

ATT GGG GAG CAG ATG GTA CAA AAT GCT GAA GAT GTT TAT GAA GCT GTT      1895
Ile Gly Glu Gln Met Val Gln Asn Ala Glu Asp Val Tyr Glu Ala Val
                420                 425                 430

CGA ACC CAA TCC CAG TTG GCA GTG CAG ATC CGG CGG GGA CGA GAA ACA      1943
Arg Thr Gln Ser Gln Leu Ala Val Gln Ile Arg Arg Gly Arg Glu Thr
            435                 440                 445

CTG ACC TTA TAT GTG ACC CCT GAG GTC ACA GAA TGAATAGATC ACCAAGAGTA    1996
Leu Thr Leu Tyr Val Thr Pro Glu Val Thr Glu
            450                 455

TGAGGCTCCT GCTCTGATTT CCTCCTTGCC TTTCTGGCTG AGGTTCTGAG GGCACCGAGA    2056

CAGAGGGTTA AATGAACCAG TGGGGGCAGG TCCCTCCAAC CACCAGCACT GACTCCTGGG    2116

CTCTGAAGAA TCACAGAAAC ACTTTTTATA TAAAATAAAA TTATACCTAG CAACATAAAA    2176

AAAAAAAAAA A                                                         2187

(2) INFORMATION FOR SEQ ID NO:25:

(i) SEQUENCE CHARACTERISTICS:
        (A) LENGTH: 458 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:25:

Met Ala Ala Pro Arg Ala Gly Arg Gly Ala Gly Trp Ser Leu Arg Ala
1               5                   10                  15

Trp Arg Ala Leu Gly Gly Ile Arg Trp Gly Arg Arg Pro Arg Leu Thr
            20                  25                  30

Pro Asp Leu Arg Ala Leu Leu Thr Ser Gly Thr Ser Asp Pro Arg Ala
        35                  40                  45

Arg Val Thr Tyr Gly Thr Pro Ser Leu Trp Ala Arg Leu Ser Val Gly
    50                  55                  60

Val Thr Glu Pro Arg Ala Cys Leu Thr Ser Gly Thr Pro Gly Pro Arg
65                  70                  75                  80

Ala Gln Leu Thr Ala Val Thr Pro Asp Thr Arg Thr Arg Glu Ala Ser
                85                  90                  95
```

```
Glu Asn Ser Gly Thr Arg Ser Arg Ala Trp Leu Ala Val Ala Leu Gly
            100                 105                 110

Ala Gly Gly Ala Val Leu Leu Leu Trp Gly Gly Arg Gly Pro
        115                 120                 125

Pro Ala Val Leu Ala Ala Val Pro Ser Pro Pro Ala Ser Pro Arg
130                 135                 140

Ser Gln Tyr Asn Phe Ile Ala Asp Val Val Glu Lys Thr Ala Pro Ala
145                 150                 155                 160

Val Val Tyr Ile Glu Ile Leu Asp Arg His Pro Phe Leu Gly Arg Glu
                165                 170                 175

Val Pro Ile Ser Asn Gly Ser Gly Phe Val Ala Ala Asp Gly Leu
                180                 185                 190

Ile Val Thr Asn Ala His Val Val Ala Asp Arg Arg Arg Val Arg Val
        195                 200                 205

Arg Leu Leu Ser Gly Asp Thr Tyr Glu Ala Val Thr Ala Val Asp
    210                 215                 220

Pro Val Ala Asp Ile Ala Thr Leu Arg Ile Gln Thr Lys Glu Pro Leu
225                 230                 235                 240

Pro Thr Leu Pro Leu Gly Arg Ser Ala Asp Val Arg Gln Gly Glu Phe
                245                 250                 255

Val Val Ala Met Gly Ser Pro Phe Ala Leu Gln Asn Thr Ile Thr Ser
                260                 265                 270

Gly Ile Val Ser Ser Ala Gln Arg Pro Ala Arg Asp Leu Gly Leu Pro
            275                 280                 285

Gln Thr Asn Val Glu Tyr Ile Gln Thr Asp Ala Ala Ile Asp Phe Gly
        290                 295                 300

Asn Ser Gly Gly Pro Leu Val Asn Leu Asp Gly Glu Val Ile Gly Val
305                 310                 315                 320

Asn Thr Met Lys Val Thr Ala Gly Ile Ser Phe Ala Ile Pro Ser Asp
                325                 330                 335

Arg Leu Arg Glu Phe Leu His Arg Gly Glu Lys Lys Asn Ser Ser Ser
                340                 345                 350

Gly Ile Ser Gly Ser Gln Arg Arg Tyr Ile Gly Val Met Met Leu Thr
            355                 360                 365

Leu Ser Pro Ser Ile Leu Ala Glu Leu Gln Leu Arg Glu Pro Ser Phe
    370                 375                 380

Pro Asp Val Gln His Gly Val Leu Ile His Lys Val Ile Leu Gly Ser
385                 390                 395                 400

Pro Ala His Arg Ala Gly Leu Arg Pro Gly Asp Val Ile Leu Ala Ile
                405                 410                 415

Gly Glu Gln Met Val Gln Asn Ala Glu Asp Val Tyr Glu Ala Val Arg
                420                 425                 430

Thr Gln Ser Gln Leu Ala Val Gln Ile Arg Arg Gly Arg Glu Thr Leu
        435                 440                 445

Thr Leu Tyr Val Thr Pro Glu Val Thr Glu
    450                 455

(2) INFORMATION FOR SEQ ID NO:26:

(i) SEQUENCE CHARACTERISTICS:
        (A) LENGTH: 2551 base pairs
        (B) TYPE: nucleic acid
        (C) STRANDEDNESS: single
        (D) TOPOLOGY: linear (ii) MOLECULE TYPE: cDNA
```

(iii) HYPOTHETICAL: NO (iv) ANTI-SENSE: NO (v) FRAGMENT TYPE:

(vi) ORIGINAL SOURCE:

(ix) FEATURE:
    (A) NAME/KEY: Coding Sequence
    (B) LOCATION: 603...1733
    (D) OTHER INFORMATION:

(xi) SEQUENCE DESCRIPTION: SEQ ID NO:26:

```
CGTGGATCCC GAGAAAGAGG CGCAGGACGA GGAGGCAGAA CCCGACTGGC GCGTAGAGCA      60

GCAGCACGAG CAGTAGGAAG CAGTCACCCG GAAGCCTGGG GGCGAGAGGC GAAGTGGTCA     120

GGCGCCGAAG GCCGAGAGCA CGCGGGGATC GGTCTCTTCC CGCCGGGTCT CTTACCGGTG     180

CGAGTCAAAG AGCCGCTCCG GCCCCGGCCC TGAGGGAAGC TCCATAACTG CTGCTTCAGG     240

AGCGCCCGGC CGTCGCCGCC GCCGCCATTT TCGCGCCCGG CCGCAGGGGC TCTTGGGAAG     300

GCGGAGTCTT TGGGCATCCG CCCGGGGTGA GGGGACCCGA AGTCCTGAGG CGCGCCGGAA     360

GGGCTAGCGG TCCCAGCATA CCCCGCGGCC CCTTGGGCCG TCTCACAACT CGCGTCCGGC     420

GGAGACCACA ATTCCCGGCA TTCGTGGGGC AGGGAGGAGT CGGCCTCCCG GAATCCTGGT     480

CCCGGCGTGC ACTTCTGAAG GACTTCAGGT ACCGGCGTGC CCCGCGTCCT ACTGTCCGCC     540

TGCTCGCGTC CTGGGTGCCG CCTCTGAGTA GGGCGGGCGA GGAGGCAGCC AAGGCGGAGC     600
```

```
TG ATG GCT GCG CCG AGG GCG GGG CGG GGT GCA GGC TGG AGC CTT CGG         647
   Met Ala Ala Pro Arg Ala Gly Arg Gly Ala Gly Trp Ser Leu Arg
   1               5                   10                  15

GCA TGG CGG GCT TTG GGG GGC ATT CGC TGG GGG AGG AGA CCC CGT TTG        695
Ala Trp Arg Ala Leu Gly Gly Ile Arg Trp Gly Arg Arg Pro Arg Leu
                20                  25                  30

ACC CCT GAC CTC CGG GCC CTG CTG ACG TCA GGA ACT TCT GAC CCC CGG        743
Thr Pro Asp Leu Arg Ala Leu Leu Thr Ser Gly Thr Ser Asp Pro Arg
                35                  40                  45

GCC CGA GTG ACT TAT GGG ACC CCC AGT CTC TGG GCC CGG TTG TCT GTT        791
Ala Arg Val Thr Tyr Gly Thr Pro Ser Leu Trp Ala Arg Leu Ser Val
            50                  55                  60

GGG GTC ACT GAA CCC CGA GCA TGC CTG ACG TCT GGG ACC CCG GGT CCC        839
Gly Val Thr Glu Pro Arg Ala Cys Leu Thr Ser Gly Thr Pro Gly Pro
65                  70                  75

CGG GCA CAA CTG ACT GCG GTG ACC CCA GAT ACC AGG ACC CGG GAG GCC        887
Arg Ala Gln Leu Thr Ala Val Thr Pro Asp Thr Arg Thr Arg Glu Ala
80                  85                  90                  95

TCA GAG AAC TCT GGA ACC CGT TCG CGC GCG TGG CTG GCG GTG GCG CTG        935
Ser Glu Asn Ser Gly Thr Arg Ser Arg Ala Trp Leu Ala Val Ala Leu
                100                 105                 110

GGC GCT GGG GGG GCA GTG CTG TTG TTG TTG TGG GGC GGG GGT CGG GGT        983
Gly Ala Gly Gly Ala Val Leu Leu Leu Leu Trp Gly Gly Gly Arg Gly
            115                 120                 125

CCT CCG GCC GTC CTC GCC GCC GTC CCT AGC CCG CCG CCC GCT TCT CCC       1031
Pro Pro Ala Val Leu Ala Ala Val Pro Ser Pro Pro Pro Ala Ser Pro
        130                 135                 140

CGG AGT CAG TAC AAC TTC ATC GCA GAT GTG GTG GAG AAG ACA GCA CCT       1079
Arg Ser Gln Tyr Asn Phe Ile Ala Asp Val Val Glu Lys Thr Ala Pro
    145                 150                 155

GCC GTG GTC TAT ATC GAG ATC CTG GAC CGG CAC CCT TTC TTG GGC CGC       1127
Ala Val Val Tyr Ile Glu Ile Leu Asp Arg His Pro Phe Leu Gly Arg
160                 165                 170                 175
```

-continued

```
GAG GTC CCT ATC TCG AAC GGC TCA GGA TTC GTG GTG GCT GCC GAT GGG       1175
Glu Val Pro Ile Ser Asn Gly Ser Gly Phe Val Val Ala Ala Asp Gly
                180                 185                 190

CTC ATT GTC ACC AAC GCC CAT GTG GTG GCT GAT CGG CGC AGA GTC CGT       1223
Leu Ile Val Thr Asn Ala His Val Val Ala Asp Arg Arg Arg Val Arg
        195                 200                 205

GTG AGA CTG CTA AGC GGC GAC ACG TAT GAG GCC GTG GTC ACA GCT GTG       1271
Val Arg Leu Leu Ser Gly Asp Thr Tyr Glu Ala Val Val Thr Ala Val
                210                 215                 220

GAT CCC GTG GCA GAC ATC GCA ACG CTG AGG ATT CAG ACT AAG GAG CCT       1319
Asp Pro Val Ala Asp Ile Ala Thr Leu Arg Ile Gln Thr Lys Glu Pro
            225                 230                 235

CTC CCC ACG CTG CCT CTG GGA CGC TCA GCT GAT GTC CGG CAA GGG GAG       1367
Leu Pro Thr Leu Pro Leu Gly Arg Ser Ala Asp Val Arg Gln Gly Glu
240                 245                 250                 255

TTT GTT GTT GCC ATG GGA AGT CCC TTT GCA CTG CAG AAC ACG ATC ACA       1415
Phe Val Val Ala Met Gly Ser Pro Phe Ala Leu Gln Asn Thr Ile Thr
                260                 265                 270

TCC GGC ATT GTT AGC TCT GCT CAG CGT CCA GCC AGA GAC CTG GGA CTC       1463
Ser Gly Ile Val Ser Ser Ala Gln Arg Pro Ala Arg Asp Leu Gly Leu
                275                 280                 285

CCC CAA ACC AAT GTG GAA TAC ATT CAA ACT GAT GCA GCT ATT GAT TTT       1511
Pro Gln Thr Asn Val Glu Tyr Ile Gln Thr Asp Ala Ala Ile Asp Phe
                290                 295                 300

GGA AAC TCT GGA GGT CCC CTG GTT AAC CTG GTG AGT GAG ACA TCC TTC       1559
Gly Asn Ser Gly Gly Pro Leu Val Asn Leu Val Ser Glu Thr Ser Phe
            305                 310                 315

CTT CCA AGA ATC CCT GCC CCA GGT CAG TGT GGG AAG GGT AGG TTT CCC       1607
Leu Pro Arg Ile Pro Ala Pro Gly Gln Cys Gly Lys Gly Arg Phe Pro
320                 325                 330                 335

CTA ATT CAA GGA TGT TTG GTC AAG TTT CTG AGC AGT TCT TTG TTG GCT       1655
Leu Ile Gln Gly Cys Leu Val Lys Phe Leu Ser Ser Ser Leu Leu Ala
                340                 345                 350

ATC TCT CAA TAT CCA ACC AGA TCT CCC CAA CAC TTG CTG GTA CTT TTG       1703
Ile Ser Gln Tyr Pro Thr Arg Ser Pro Gln His Leu Leu Val Leu Leu
                355                 360                 365

TTC GGG TGC CCC CAT CCC CTA CTA TTT GTT TAGGCTAGGG AACTGGGGGC TGTA    1757
Phe Gly Cys Pro His Pro Leu Leu Phe Val
                370                 375

TCCCTGCAGG ATGGGGAGGT GATTGGAGTG AACACCATGA AGGTCACAGC TGGAATCTCC     1817

TTTGCCATCC CTTCTGATCG TCTTCGAGAG TTTCTGCATC GTGGGGAAAA GAAGAATTCC     1877

TCCTCCGGAA TCAGTGGGTC CCAGCGGCGC TACATTGGGG TGATGATGCT GACCCTGAGT     1937

CCCAGCATCC TTGCTGAACT ACAGCTTCGA GAACCAAGCT TTCCCGATGT TCAGCATGGT     1997

GTACTCATCC ATAAAGTCAT CCTGGGCTCC CCTGCACACC GGGCTGGTCT GCGGCCTGGT     2057

GATGTGATTT TGGCCATTGG GGAGCAGATG GTACAAAATG CTGAAGATGT TTATGAAGCT     2117

GTTCGAACCC AATCCCAGTT GGCAGTGCAG ATCCGGCGGG GACGAGAAAC ACTGACCTTA     2177

TATGTGACCC CTGAGGTCAC AGAATGAATA GATCACCAAG AGTATGAGGC TCCTGCTCTG     2237

ATTTCCTCCT TGCCTTTCTG GCTGAGGTTC TGAGGGCACC GAGACAGAGG GTTAAATGAA     2297

CCAGTGGGGG CAGGTCCCTC CAACCACCAG CACTGACTCC TGGGCTCTGA AGAATCACAG     2357

AAACACTTTT TATATAAAAT AAAATTATAC CTAGCAACAT ATTATAGTAA AAAATGAGGT     2417

GGGAGGGCTG GATCTTTTCC CCCACCAAAA GGCTAGAGGT AAAGCTGTAT CCCCCTAAAC     2477

TTAGGGGAGA TACTGGAGCT GACCATCCTG ACCTCCTATT AAAGAAAATG AGCTGCTGAA     2537

AAAAAAAAAA AAAA                                                      2551
```

(2) INFORMATION FOR SEQ ID NO:27:

(i) SEQUENCE CHARACTERISTICS:
        (A) LENGTH: 377 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:27:

```
Met Ala Ala Pro Arg Ala Gly Arg Gly Ala Gly Trp Ser Leu Arg Ala
 1               5                  10                  15

Trp Arg Ala Leu Gly Gly Ile Arg Trp Gly Arg Arg Pro Arg Leu Thr
                20                  25                  30

Pro Asp Leu Arg Ala Leu Leu Thr Ser Gly Thr Ser Asp Pro Arg Ala
            35                  40                  45

Arg Val Thr Tyr Gly Thr Pro Ser Leu Trp Ala Arg Leu Ser Val Gly
        50                  55                  60

Val Thr Glu Pro Arg Ala Cys Leu Thr Ser Gly Thr Pro Gly Pro Arg
65                  70                  75                  80

Ala Gln Leu Thr Ala Val Thr Pro Asp Thr Arg Thr Arg Glu Ala Ser
                85                  90                  95

Glu Asn Ser Gly Thr Arg Ser Arg Ala Trp Leu Ala Val Ala Leu Gly
            100                 105                 110

Ala Gly Gly Ala Val Leu Leu Leu Trp Gly Gly Arg Gly Pro
        115                 120                 125

Pro Ala Val Leu Ala Ala Val Pro Ser Pro Pro Ala Ser Pro Arg
            130                 135                 140

Ser Gln Tyr Asn Phe Ile Ala Asp Val Val Glu Lys Thr Ala Pro Ala
145                 150                 155                 160

Val Val Tyr Ile Glu Ile Leu Asp Arg His Pro Phe Leu Gly Arg Glu
                165                 170                 175

Val Pro Ile Ser Asn Gly Ser Gly Phe Val Val Ala Ala Asp Gly Leu
            180                 185                 190

Ile Val Thr Asn Ala His Val Val Ala Asp Arg Arg Arg Val Arg Val
        195                 200                 205

Arg Leu Leu Ser Gly Asp Thr Tyr Glu Ala Val Val Thr Ala Val Asp
    210                 215                 220

Pro Val Ala Asp Ile Ala Thr Leu Arg Ile Gln Thr Lys Glu Pro Leu
225                 230                 235                 240

Pro Thr Leu Pro Leu Gly Arg Ser Ala Asp Val Arg Gln Gly Glu Phe
                245                 250                 255

Val Val Ala Met Gly Ser Pro Phe Ala Leu Gln Asn Thr Ile Thr Ser
            260                 265                 270

Gly Ile Val Ser Ala Gln Arg Pro Ala Arg Asp Leu Gly Leu Pro
        275                 280                 285

Gln Thr Asn Val Glu Tyr Ile Gln Thr Asp Ala Ala Ile Asp Phe Gly
    290                 295                 300

Asn Ser Gly Gly Pro Leu Val Asn Leu Val Ser Glu Thr Ser Phe Leu
305                 310                 315                 320
```

```
Pro Arg Ile Pro Ala Pro Gly Gln Cys Gly Lys Gly Arg Phe Pro Leu
            325                 330                 335

Ile Gln Gly Cys Leu Val Lys Phe Leu Ser Ser Ser Leu Leu Ala Ile
        340                 345                 350

Ser Gln Tyr Pro Thr Arg Ser Pro Gln His Leu Leu Val Leu Leu Phe
        355                 360                 365

Gly Cys Pro His Pro Leu Leu Phe Val
    370                 375
```

(2) INFORMATION FOR SEQ ID NO:28:

(i) SEQUENCE CHARACTERISTICS:
        (A) LENGTH: 2144 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 603...1910
        (D) OTHER INFORMATION:

(xi) SEQUENCE DESCRIPTION: SEQ ID NO:28:

```
CGTGGATCCC GAGAAAGAGG CGCAGGACGA GGAGGCAGAA CCCGACTGGC GCGTAGAGCA      60

GCAGCACGAG CAGTAGGAAG CAGTCACCCG GAAGCCTGGG GGCGAGAGGC GAAGTGGTCA     120

GGCGCCGAAG GCCGAGAGCA CGCGGGGATC GGTCTCTTCC CGCCGGGTCT CTTACCGGTG     180

CGAGTCAAAG AGCCGCTCCG GCCCCGGCCC TGAGGGAAGC TCCATAACTG CTGCTTCAGG     240

AGCGCCCGGC CGTCGCCGCC GCCGCCATTT TCGCGCCCGG CCGCAGGGGC TCTTGGGAAG     300

GCGGAGTCTT TGGGCATCCG CCCGGGGTGA GGGGACCCGA AGTCCTGAGG CGCGCCGGAA     360

GGGCTAGCGG TCCCAGCATA CCCCGCGGCC CCTTGGGCCG TCTCACAACT CGCGTCCGGC     420

GGAGACCACA ATTCCCGGCA TTCGTGGGGC AGGGAGGAGT CGGCCTCCCG GAATCCTGGT     480

CCCGGCGTGC ACTTCTGAAG GACTTCAGGT ACCGGCGTGC CCCGCGTCCT ACTGTCCGCC     540

TGCTCGCGTC CTGGGTGCCG CCTCTGAGTA GGGCGGGCGA GGAGGCAGCC AAGGCGGAGC     600

TG ATG GCT GCG CCG AGG GCG GGG CGG GGT GCA GGC TGG AGC CTT CGG         647
   Met Ala Ala Pro Arg Ala Gly Arg Gly Ala Gly Trp Ser Leu Arg
     1               5                  10                  15

GCA TGG CGG GCT TTG GGG GGC ATT CGC TGG GGG AGG AGA CCC CGT TTG       695
Ala Trp Arg Ala Leu Gly Gly Ile Arg Trp Gly Arg Arg Pro Arg Leu
                20                  25                  30

ACC CCT GAC CTC CGG GCC CTG CTG ACG TCA GGA ACT TCT GAC CCC CGG       743
Thr Pro Asp Leu Arg Ala Leu Leu Thr Ser Gly Thr Ser Asp Pro Arg
            35                  40                  45

GCC CGA GTG ACT TAT GGG ACC CCC AGT CTC TGG GCC CGG TTG TCT GTT       791
Ala Arg Val Thr Tyr Gly Thr Pro Ser Leu Trp Ala Arg Leu Ser Val
        50                  55                  60

GGG GTC ACT GAA CCC CGA GCA TGC CTG ACG TCT GGG ACC CCG GGT CCC       839
Gly Val Thr Glu Pro Arg Ala Cys Leu Thr Ser Gly Thr Pro Gly Pro
    65                  70                  75
```

| | | |
|---|---|---|
| CGG GCA CAA CTG ACT GCG GTG ACC CCA GAT ACC AGG ACC CGG GAG GCC<br>Arg Ala Gln Leu Thr Ala Val Thr Pro Asp Thr Arg Thr Arg Glu Ala<br>80                          85                          90                          95 | 887 |
| TCA GAG AAC TCT GGA ACC CGT TCG CGC GCG TGG CTG GCG GTG GCG CTG<br>Ser Glu Asn Ser Gly Thr Arg Ser Arg Ala Trp Leu Ala Val Ala Leu<br>                          100                        105                        110 | 935 |
| GGC GCT GGG GGG GCA GTG CTG TTG TTG TTG TGG GGC GGG GGT CGG GGT<br>Gly Ala Gly Gly Ala Val Leu Leu Leu Leu Trp Gly Gly Gly Arg Gly<br>                        115                        120                        125 | 983 |
| CCT CCG GCC GTC CTC GCC GCC GTC CCT AGC CCG CCG CCC GCT TCT CCC<br>Pro Pro Ala Val Leu Ala Ala Val Pro Ser Pro Pro Pro Ala Ser Pro<br>            130                        135                        140 | 1031 |
| CGG AGT CAG TAC AAC TTC ATC GCA GAT GTG GTG GAG AAG ACA GCA CCT<br>Arg Ser Gln Tyr Asn Phe Ile Ala Asp Val Val Glu Lys Thr Ala Pro<br>145                          150                        155 | 1079 |
| GCC GTG GTC TAT ATC GAG ATC CTG GAC CGG CAC CCT TTC TTG GGC CGC<br>Ala Val Val Tyr Ile Glu Ile Leu Asp Arg His Pro Phe Leu Gly Arg<br>160                          165                        170                        175 | 1127 |
| GAG GTC CCT ATC TCG AAC GGC TCA GGA TTC GTG GTG GCT GCC GAT GGG<br>Glu Val Pro Ile Ser Asn Gly Ser Gly Phe Val Val Ala Ala Asp Gly<br>                        180                        185                        190 | 1175 |
| CTC ATT GTC ACC AAC GCC CAT GTG GTG GCT GAT CGG CGC AGA GTC CGT<br>Leu Ile Val Thr Asn Ala His Val Val Ala Asp Arg Arg Arg Val Arg<br>                        195                        200                        205 | 1223 |
| GTG AGA CTG CTA AGC GGC GAC ACG TAT GAG GCC GTG GTC ACA GCT GTG<br>Val Arg Leu Leu Ser Gly Asp Thr Tyr Glu Ala Val Val Thr Ala Val<br>            210                        215                        220 | 1271 |
| GAT CCC GTG GCA GAC ATC GCA ACG CTG AGG ATT CAG ACT AAG GAG CCT<br>Asp Pro Val Ala Asp Ile Ala Thr Leu Arg Ile Gln Thr Lys Glu Pro<br>225                          230                        235 | 1319 |
| CTC CCC ACG CTG CCT CTG GGA CGC TCA GCT GAT GTC CGG CAA GGG GAG<br>Leu Pro Thr Leu Pro Leu Gly Arg Ser Ala Asp Val Arg Gln Gly Glu<br>240                          245                        250                        255 | 1367 |
| TTT GTT GTT GCC ATG GGA AGT CCC TTT GCA CTG CAG AAC ACG ATC ACA<br>Phe Val Val Ala Met Gly Ser Pro Phe Ala Leu Gln Asn Thr Ile Thr<br>                        260                        265                        270 | 1415 |
| TCC GGC ATT GTT AGC TCT GCT CAG CGT CCA GCC AGA GAC CTG GGA CTC<br>Ser Gly Ile Val Ser Ser Ala Gln Arg Pro Ala Arg Asp Leu Gly Leu<br>            275                        280                        285 | 1463 |
| CCC CAA ACC AAT GTG GAA TAC ATT CAA ACT GAT GCA GCT ATT GAT TTT<br>Pro Gln Thr Asn Val Glu Tyr Ile Gln Thr Asp Ala Ala Ile Asp Phe<br>                        290                        295                        300 | 1511 |
| GGA AAC TCT GGA GGT CCC CTG GTT AAC CTG GCT AGG GAA CTG GGG GCT<br>Gly Asn Ser Gly Gly Pro Leu Val Asn Leu Ala Arg Glu Leu Gly Ala<br>305                          310                        315 | 1559 |
| GTA TCC CTG CAG GAT GGG GAG GTG ATT GGA GTG AAC ACC ATG AAG GTC<br>Val Ser Leu Gln Asp Gly Glu Val Ile Gly Val Asn Thr Met Lys Val<br>320                          325                        330                        335 | 1607 |
| ACA GCT GGA ATC TCC TTT GCC ATC CCT TCT GAT CGT CTT CGA GAG TTT<br>Thr Ala Gly Ile Ser Phe Ala Ile Pro Ser Asp Arg Leu Arg Glu Phe<br>                        340                        345                        350 | 1655 |
| CTG CAT CGT GGG GAA AAG AAG AAT TCC TCC TCC GGA ATC AGT GGG TCC<br>Leu His Arg Gly Glu Lys Lys Asn Ser Ser Ser Gly Ile Ser Gly Ser<br>            355                        360                        365 | 1703 |
| CAG CGG CGC TAC ATT GGG GTG ATG ATG CTG ACC CTG AGT CCC AGG GCT<br>Gln Arg Arg Tyr Ile Gly Val Met Met Leu Thr Leu Ser Pro Arg Ala<br>            370                        375                        380 | 1751 |
| GGT CTG CGG CCT GGT GAT GTG ATT TTG GCC ATT GGG GAG CAG ATG GTA<br>Gly Leu Arg Pro Gly Asp Val Ile Leu Ala Ile Gly Glu Gln Met Val<br>385                          390                        395 | 1799 |

-continued

```
CAA AAT GCT GAA GAT GTT TAT GAA GCT GTT CGA ACC CAA TCC CAG TTG    1847
Gln Asn Ala Glu Asp Val Tyr Glu Ala Val Arg Thr Gln Ser Gln Leu
400                 405                 410                 415

GCA GTG CAG ATC CGG CGG GGA CGA GAA ACA CTG ACC TTA TAT GTG ACC    1895
Ala Val Gln Ile Arg Arg Gly Arg Glu Thr Leu Thr Leu Tyr Val Thr
            420                 425                 430

CCT GAG GTC ACA GAA TGAATAGATC ACCAAGAGTA TGAGGCTCCT GCTCTGATTT CC 1952
Pro Glu Val Thr Glu
            435

TCCTTGCCTT TCTGGCTGAG GTTCTGAGGG CACCGAGACA GAGGGTTAAA TGAACCAGTG    2012

GGGGCAGGTC CCTCCAACCA CCAGCACTGA CTCCTGGGCT CTGAAGAATC ACAGAAACAC    2072

TTTTTATATA AAATAAAATT ATACCTAGCA AAAAAAAAAA AAAAAAAAAA AAAAAAAAAA    2132

AAAAAAAAAA AA                                                        2144
```

(2) INFORMATION FOR SEQ ID NO:29:

(i) SEQUENCE CHARACTERISTICS:
        (A) LENGTH: 436 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:29:

```
Met Ala Ala Pro Arg Ala Gly Arg Gly Ala Gly Trp Ser Leu Arg Ala
1               5                   10                  15

Trp Arg Ala Leu Gly Gly Ile Arg Trp Gly Arg Arg Pro Arg Leu Thr
            20                  25                  30

Pro Asp Leu Arg Ala Leu Leu Thr Ser Gly Thr Ser Asp Pro Arg Ala
        35                  40                  45

Arg Val Thr Tyr Gly Thr Pro Ser Leu Trp Ala Arg Leu Ser Val Gly
50                  55                  60

Val Thr Glu Pro Arg Ala Cys Leu Thr Ser Gly Thr Pro Gly Pro Arg
65                  70                  75                  80

Ala Gln Leu Thr Ala Val Thr Pro Asp Thr Arg Thr Arg Glu Ala Ser
                85                  90                  95

Glu Asn Ser Gly Thr Arg Ser Arg Ala Trp Leu Ala Val Ala Leu Gly
            100                 105                 110

Ala Gly Gly Ala Val Leu Leu Leu Leu Trp Gly Gly Gly Arg Gly Pro
        115                 120                 125

Pro Ala Val Leu Ala Ala Val Pro Ser Pro Pro Ala Ser Pro Arg
130                 135                 140

Ser Gln Tyr Asn Phe Ile Ala Asp Val Val Glu Lys Thr Ala Pro Ala
145                 150                 155                 160

Val Val Tyr Ile Glu Ile Leu Asp Arg His Pro Phe Leu Gly Arg Glu
                165                 170                 175

Val Pro Ile Ser Asn Gly Ser Gly Phe Val Val Ala Ala Asp Gly Leu
            180                 185                 190

Ile Val Thr Asn Ala His Val Val Ala Asp Arg Arg Val Arg Val
        195                 200                 205
```

```
Arg Leu Leu Ser Gly Asp Thr Tyr Glu Ala Val Val Thr Ala Val Asp
    210                 215                 220
Pro Val Ala Asp Ile Ala Thr Leu Arg Ile Gln Thr Lys Glu Pro Leu
225                 230                 235                 240
Pro Thr Leu Pro Leu Gly Arg Ser Ala Asp Val Arg Gln Gly Glu Phe
            245                 250                 255
Val Val Ala Met Gly Ser Pro Phe Ala Leu Gln Asn Thr Ile Thr Ser
            260                 265                 270
Gly Ile Val Ser Ser Ala Gln Arg Pro Ala Arg Asp Leu Gly Leu Pro
        275                 280                 285
Gln Thr Asn Val Glu Tyr Ile Gln Thr Asp Ala Ala Ile Asp Phe Gly
    290                 295                 300
Asn Ser Gly Gly Pro Leu Val Asn Leu Ala Arg Glu Leu Gly Ala Val
305                 310                 315                 320
Ser Leu Gln Asp Gly Glu Val Ile Gly Val Asn Thr Met Lys Val Thr
                325                 330                 335
Ala Gly Ile Ser Phe Ala Ile Pro Ser Asp Arg Leu Arg Glu Phe Leu
            340                 345                 350
His Arg Gly Glu Lys Lys Asn Ser Ser Ser Gly Ile Ser Gly Ser Gln
        355                 360                 365
Arg Arg Tyr Ile Gly Val Met Met Leu Thr Leu Ser Pro Arg Ala Gly
    370                 375                 380
Leu Arg Pro Gly Asp Val Ile Leu Ala Ile Gly Glu Gln Met Val Gln
385                 390                 395                 400
Asn Ala Glu Asp Val Tyr Glu Ala Val Arg Thr Gln Ser Gln Leu Ala
                405                 410                 415
Val Gln Ile Arg Arg Gly Arg Glu Thr Leu Thr Leu Tyr Val Thr Pro
            420                 425                 430
Glu Val Thr Glu
        435

(2) INFORMATION FOR SEQ ID NO:30:

(i) SEQUENCE CHARACTERISTICS:
        (A) LENGTH: 2187 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:Polymorphic variants at 672 and 1435
            aa24=Arg/Cys   aa278=Ala/Val
        (A) NAME/KEY: Coding Sequence
        (B) LOCATION: 603...1976
        (D) OTHER INFORMATION:

(xi) SEQUENCE DESCRIPTION: SEQ ID NO:30:

CGTGGATCCC GAGAAAGAGG CGCAGGACGA GGAGGCAGAA CCCGACTGGC GCGTAGAGCA      60

GCAGCACGAG CAGTAGGAAG CAGTCACCCG GAAGCCTGGG GGCGAGAGGC GAAGTGGTCA     120

GGCGCCGAAG GCCGAGAGCA CGCGGGGATC GGTCTCTTCC CGCCGGGTCT CTTACCGGTG     180

CGAGTCAAAG AGCCGCTCCG GCCCCGGCCC TGAGGGAAGC TCCATAACTG CTGCTTCAGG     240
```

-continued

```
AGCGCCCGGC CGTCGCCGCC GCCGCCATTT TCGCGCCCGG CCGCAGGGGC TCTTGGGAAG    300

GCGGAGTCTT TGGGCATCCG CCCGGGGTGA GGGGACCCGA AGTCCTGAGG CGCGCCGGAA    360

GGGCTAGCGG TCCCAGCATA CCCCGCGGCC CCTTGGGCCG TCTCACAACT CGCGTCCGGC    420

GGAGACCACA ATTCCCGGCA TTCGTGGGGC AGGGAGGAGT CGGCCTCCCG GAATCCTGGT    480

CCCGGCGTGC ACTTCTGAAG GACTTCAGGT ACCGGCGTGC CCCGCGTCCT ACTGTCCGCC    540

TGCTCGCGTC CTGGGTGCCG CCTCTGAGTA GGGCGGGCGA GGAGGCAGCC AAGGCGGAGC    600
```

```
TG ATG GCT GCG CCG AGG GCG GGG CGG GGT GCA GGC TGG AGC CTT CGG        647
   Met Ala Ala Pro Arg Ala Gly Arg Gly Ala Gly Trp Ser Leu Arg
   1               5                  10                 15

GCA TGG CGG GCT TTG GGG GGC ATT YGC TGG GGG AGG AGA CCC CGT TTG       695
Ala Trp Arg Ala Leu Gly Gly Ile Xaa Trp Gly Arg Arg Pro Arg Leu
            20                  25                  30

ACC CCT GAC CTC CGG GCC CTG CTG ACG TCA GGA ACT TCT GAC CCC CGG       743
Thr Pro Asp Leu Arg Ala Leu Leu Thr Ser Gly Thr Ser Asp Pro Arg
            35                  40                  45

GCC CGA GTG ACT TAT GGG ACC CCC AGT CTC TGG GCC CGG TTG TCT GTT       791
Ala Arg Val Thr Tyr Gly Thr Pro Ser Leu Trp Ala Arg Leu Ser Val
            50                  55                  60

GGG GTC ACT GAA CCC CGA GCA TGC CTG ACG TCT GGG ACC CCG GGT CCC       839
Gly Val Thr Glu Pro Arg Ala Cys Leu Thr Ser Gly Thr Pro Gly Pro
65                  70                  75

CGG GCA CAA CTG ACT GCG GTG ACC CCA GAT ACC AGG ACC CGG GAG GCC       887
Arg Ala Gln Leu Thr Ala Val Thr Pro Asp Thr Arg Thr Arg Glu Ala
80                  85                  90                  95

TCA GAG AAC TCT GGA ACC CGT TCG CGC GCG TGG CTG GCG GTG GCG CTG       935
Ser Glu Asn Ser Gly Thr Arg Ser Arg Ala Trp Leu Ala Val Ala Leu
                100                 105                 110

GGC GCT GGG GGG GCA GTG CTG TTG TTG TTG TGG GGC GGG GGT CGG GGT       983
Gly Ala Gly Gly Ala Val Leu Leu Leu Leu Trp Gly Gly Gly Arg Gly
                115                 120                 125

CCT CCG GCC GTC CTC GCC GCC GTC CCT AGC CCG CCG CCC GCT TCT CCC      1031
Pro Pro Ala Val Leu Ala Ala Val Pro Ser Pro Pro Pro Ala Ser Pro
        130                 135                 140

CGG AGT CAG TAC AAC TTC ATC GCA GAT GTG GTG GAG AAG ACA GCA CCT      1079
Arg Ser Gln Tyr Asn Phe Ile Ala Asp Val Val Glu Lys Thr Ala Pro
    145                 150                 155

GCC GTG GTC TAT ATC GAG ATC CTG GAC CGG CAC CCT TTC TTG GGC CGC      1127
Ala Val Val Tyr Ile Glu Ile Leu Asp Arg His Pro Phe Leu Gly Arg
160                 165                 170                 175

GAG GTC CCT ATC TCG AAC GGC TCA GGA TTC GTG GTG GCT GCC GAT GGG      1175
Glu Val Pro Ile Ser Asn Gly Ser Gly Phe Val Val Ala Ala Asp Gly
                180                 185                 190

CTC ATT GTC ACC AAC GCC CAT GTG GTG GCT GAT CGG CGC AGA GTC CGT      1223
Leu Ile Val Thr Asn Ala His Val Val Ala Asp Arg Arg Arg Val Arg
                195                 200                 205

GTG AGA CTG CTA AGC GGC GAC ACG TAT GAG GCC GTG GTC ACA GCT GTG      1271
Val Arg Leu Leu Ser Gly Asp Thr Tyr Glu Ala Val Val Thr Ala Val
        210                 215                 220

GAT CCC GTG GCA GAC ATC GCA ACG CTG AGG ATT CAG ACT AAG GAG CCT      1319
Asp Pro Val Ala Asp Ile Ala Thr Leu Arg Ile Gln Thr Lys Glu Pro
225                 230                 235

CTC CCC ACG CTG CCT CTG GGA CGC TCA GCT GAT GTC CGG CAA GGG GAG      1367
Leu Pro Thr Leu Pro Leu Gly Arg Ser Ala Asp Val Arg Gln Gly Glu
240                 245                 250                 255

TTT GTT GTT GCC ATG GGA AGT CCC TTT GCA CTG CAG AAC ACG ATC ACA      1415
Phe Val Val Ala Met Gly Ser Pro Phe Ala Leu Gln Asn Thr Ile Thr
                260                 265                 270
```

| | | |
|---|---|---|
| TCC GGC ATT GTT AGC TCT YCT CAG CGT CCA GCC AGA GAC CTG GGA CTC<br>Ser Gly Ile Val Ser Ser Xaa Gln Arg Pro Ala Arg Asp Leu Gly Leu<br>                 275                                 280                             285 | 1463 | |
| CCC CAA ACC AAT GTG GAA TAC ATT CAA ACT GAT GCA GCT ATT GAT TTT<br>Pro Gln Thr Asn Val Glu Tyr Ile Gln Thr Asp Ala Ala Ile Asp Phe<br>                 290                                 295                             300 | 1511 | |
| GGA AAC TCT GGA GGT CCC CTG GTT AAC CTG GAT GGG GAG GTG ATT GGA<br>Gly Asn Ser Gly Gly Pro Leu Val Asn Leu Asp Gly Glu Val Ile Gly<br>305                               310                                 315 | 1559 | |
| GTG AAC ACC ATG AAG GTC ACA GCT GGA ATC TCC TTT GCC ATC CCT TCT<br>Val Asn Thr Met Lys Val Thr Ala Gly Ile Ser Phe Ala Ile Pro Ser<br>320                             325                               330                       335 | 1607 | |
| GAT CGT CTT CGA GAG TTT CTG CAT CGT GGG GAA AAG AAG AAT TCC TCC<br>Asp Arg Leu Arg Glu Phe Leu His Arg Gly Glu Lys Lys Asn Ser Ser<br>                 340                                 345                             350 | 1655 | |
| TCC GGA ATC AGT GGG TCC CAG CGG CGC TAC ATT GGG GTG ATG ATG CTG<br>Ser Gly Ile Ser Gly Ser Gln Arg Arg Tyr Ile Gly Val Met Met Leu<br>                 355                                 360                             365 | 1703 | |
| ACC CTG AGT CCC AGC ATC CTT GCT GAA CTA CAG CTT CGA GAA CCA AGC<br>Thr Leu Ser Pro Ser Ile Leu Ala Glu Leu Gln Leu Arg Glu Pro Ser<br>                 370                                 375                             380 | 1751 | |
| TTT CCC GAT GTT CAG CAT GGT GTA CTC ATC CAT AAA GTC ATC CTG GGC<br>Phe Pro Asp Val Gln His Gly Val Leu Ile His Lys Val Ile Leu Gly<br>385                               390                                 395 | 1799 | |
| TCC CCT GCA CAC CGG GCT GGT CTG CGG CCT GGT GAT GTG ATT TTG GCC<br>Ser Pro Ala His Arg Ala Gly Leu Arg Pro Gly Asp Val Ile Leu Ala<br>400                               405                               410                       415 | 1847 | |
| ATT GGG GAG CAG ATG GTA CAA AAT GCT GAA GAT GTT TAT GAA GCT GTT<br>Ile Gly Glu Gln Met Val Gln Asn Ala Glu Asp Val Tyr Glu Ala Val<br>                              420                               425                             430 | 1895 | |
| CGA ACC CAA TCC CAG TTG GCA GTG CAG ATC CGG CGG GGA CGA GAA ACA<br>Arg Thr Gln Ser Gln Leu Ala Val Gln Ile Arg Arg Gly Arg Glu Thr<br>                 435                                 440                             445 | 1943 | |
| CTG ACC TTA TAT GTG ACC CCT GAG GTC ACA GAA TGAATAGATC ACCAAGAGTA<br>Leu Thr Leu Tyr Val Thr Pro Glu Val Thr Glu<br>                 450                                 455 | 1996 | |
| TGAGGCTCCT GCTCTGATTT CCTCCTTGCC TTTCTGGCTG AGGTTCTGAG GGCACCGAGA | 2056 | |
| CAGAGGGTTA AATGAACCAG TGGGGGCAGG TCCCTCCAAC CACCAGCACT GACTCCTGGG | 2116 | |
| CTCTGAAGAA TCACAGAAAC ACTTTTTATA TAAAATAAAA TTATACCTAG CAACATAAAA | 2176 | |
| AAAAAAAAA A | 2187 | |

(2) INFORMATION FOR SEQ ID NO:31:

(i) SEQUENCE CHARACTERISTICS:
        (A) LENGTH: 458 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:
        Feature
           24 Xaa = Arg or Cys
          278 Xaa = Ala or Val (xi) SEQUENCE DESCRIPTION: SEQ ID NO:31:

-continued

```
Met Ala Ala Pro Arg Ala Gly Arg Gly Ala Gly Trp Ser Leu Arg Ala
 1               5                  10                  15

Trp Arg Ala Leu Gly Gly Ile Xaa Trp Gly Arg Arg Pro Arg Leu Thr
             20                  25                  30

Pro Asp Leu Arg Ala Leu Leu Thr Ser Gly Thr Ser Asp Pro Arg Ala
         35                  40                  45

Arg Val Thr Tyr Gly Thr Pro Ser Leu Trp Ala Arg Leu Ser Val Gly
     50                  55                  60

Val Thr Glu Pro Arg Ala Cys Leu Thr Ser Gly Thr Pro Gly Pro Arg
 65              70                  75                  80

Ala Gln Leu Thr Ala Val Thr Pro Asp Thr Arg Thr Arg Glu Ala Ser
                 85                  90                  95

Glu Asn Ser Gly Thr Arg Ser Arg Ala Trp Leu Ala Val Ala Leu Gly
                100                 105                 110

Ala Gly Gly Ala Val Leu Leu Leu Trp Gly Gly Arg Gly Pro
            115                 120                 125

Pro Ala Val Leu Ala Ala Val Pro Ser Pro Pro Ala Ser Pro Arg
130                 135                 140

Ser Gln Tyr Asn Phe Ile Ala Asp Val Val Glu Lys Thr Ala Pro Ala
145                 150                 155                 160

Val Val Tyr Ile Glu Ile Leu Asp Arg His Pro Phe Leu Gly Arg Glu
                165                 170                 175

Val Pro Ile Ser Asn Gly Ser Gly Phe Val Val Ala Ala Asp Gly Leu
                180                 185                 190

Ile Val Thr Asn Ala His Val Val Ala Asp Arg Arg Arg Val Arg Val
        195                 200                 205

Arg Leu Leu Ser Gly Asp Thr Tyr Glu Ala Val Val Thr Ala Val Asp
    210                 215                 220

Pro Val Ala Asp Ile Ala Thr Leu Arg Ile Gln Thr Lys Glu Pro Leu
225                 230                 235                 240

Pro Thr Leu Pro Leu Gly Arg Ser Ala Asp Val Arg Gln Gly Glu Phe
                245                 250                 255

Val Val Ala Met Gly Ser Pro Phe Ala Leu Gln Asn Thr Ile Thr Ser
                260                 265                 270

Gly Ile Val Ser Ser Xaa Gln Arg Pro Ala Arg Asp Leu Gly Leu Pro
            275                 280                 285

Gln Thr Asn Val Glu Tyr Ile Gln Thr Asp Ala Ala Ile Asp Phe Gly
    290                 295                 300

Asn Ser Gly Gly Pro Leu Val Asn Leu Asp Gly Glu Val Ile Gly Val
305                 310                 315                 320

Asn Thr Met Lys Val Thr Ala Gly Ile Ser Phe Ala Ile Pro Ser Asp
                325                 330                 335

Arg Leu Arg Glu Phe Leu His Arg Gly Glu Lys Lys Asn Ser Ser Ser
                340                 345                 350

Gly Ile Ser Gly Ser Gln Arg Arg Tyr Ile Gly Val Met Met Leu Thr
            355                 360                 365

Leu Ser Pro Ser Ile Leu Ala Glu Leu Gln Leu Arg Glu Pro Ser Phe
    370                 375                 380

Pro Asp Val Gln His Gly Val Leu Ile His Lys Val Ile Leu Gly Ser
385                 390                 395                 400

Pro Ala His Arg Ala Gly Leu Arg Pro Gly Asp Val Ile Leu Ala Ile
                405                 410                 415

Gly Glu Gln Met Val Gln Asn Ala Glu Asp Val Tyr Glu Ala Val Arg
                420                 425                 430
```

```
Thr Gln Ser Gln Leu Ala Val Gln Ile Arg Arg Gly Arg Glu Thr Leu
        435                 440                 445
Thr Leu Tyr Val Thr Pro Glu Val Thr Glu
    450                 455
```

(2) INFORMATION FOR SEQ ID NO:32:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:32:

CATCCGGCAT TGTTAGCTCT GC                                      22

(2) INFORMATION FOR SEQ ID NO:33:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:33:

CATCCGGCAT TGTTAGCTCT GT                                      22

(2) INFORMATION FOR SEQ ID NO:34:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:34:

CAATAGCTGC ATCAGTTTGA ATG                                    23

(2) INFORMATION FOR SEQ ID NO:35:

(i) SEQUENCE CHARACTERISTICS:

(A) LENGTH: 22 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:35:

TGGCGGGCTT TGGGGGGCAT TC                                               22

(2) INFORMATION FOR SEQ ID NO:36:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:36:

TGGCGGGCTT TGGGGGGCAT TT                                               22

(2) INFORMATION FOR SEQ ID NO:37:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:37:

GACGTCAGCA GGGCCCGGAG GTC                                              23

(2) INFORMATION FOR SEQ ID NO:38:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO -continued

```
        (v) FRAGMENT TYPE:

(vi) ORIGINAL SOURCE:

(xi) SEQUENCE DESCRIPTION: SEQ ID NO:38:

GATACCCCAG CAGAAGCTGG                                              20

(2) INFORMATION FOR SEQ ID NO:39:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:39:

GATACCCCAG CAGAAGCTGT                                              20

(2) INFORMATION FOR SEQ ID NO:40:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:40:

GCTGACATCA TTGGCGGAGA C                                            21
```

HUMAN SERINE PROTEASE

CROSS-REFERENCE TO RELATED APPLICATIONS

This application claims the benefit of U.S. Provisional Application Ser. No. 60/032,875, filed Dec. 13, 1996, U.S. Provisional Application Ser. No. 60/027,873, filed Oct. 25, 1996, and U.S. Provisional Application Ser. No. 60/025,436, filed Sep. 6, 1996.

FIELD OF THE INVENTION

The present invention relates to isolated human serine protease (PSP1) polynucleotides, their homologs and isoforms and polymorphic variants and their detection; to essentially pure PSP1 proteins; and to compositions and methods of producing and using PSP1 polynucleotides and proteins.

BACKGROUND OF THE INVENTION

Mutations in the presenilins (PS-1 and PS-2) account for ~95% (75% and 20%, respectively) of all cases of early onset familial Alzheimer's disease (FAD). See R. Sherrington et al., Nature 375, 754–760 (1995); E. I. Rogaev et al., Nature 376, 775–778 (1995); and E. Levy-Lahad et al., Science 269, 973–977 (1995). The presenilins are highly homologous (67% identical), multi-membrane spanning proteins whose function is unknown.

It has been demonstrated that the 46 kDa full-length PS-1 protein is normally processed to 28 kDa and 18 kDa fragments; PS-2 has been reported to be similarly cleaved. See M. Mercken et al., FEBS Letters 389, 297–303 (1996). The predicted cleavage site(s) to account for fragments of this size would be in a region of the protein coded for by exon 8 and exon 9. Exon 8 is a hot spot for mutations leading to FAD. Thus, this region of PS-1, and potentially the cleavage of PS-1 in this region by a preseninilinase protease, are important events in the functionality of the protein. A region of PS-1 spanning exons 8–11 has been demonstrated in the present invention to specifically bind a protease, PSP1, whose activity against its endogenous substrates and/or ability to bind to PS-1 are important in the pathology of neurodegeneration associated with AD, frontal lobe dementia, cortical lewy body disease, dementia of parkinson's disease, acute and chronic phases of degeneration following stroke or head injury, neuronal degeneration found in motor neurone disease, AIDS dementia and chronic epileps. Thus, a need exists for provision of the nucleotide and amino acid sequences corresponding to PSP1, for modulators of PSP1 binding to PS-1, and/or modulators of PSP1's proteolytic activity, for methods to identify such modulators and for reagents useful in such methods.

SUMMARY OF THE INVENTION

Accordingly, one aspect of the present invention is an isolated polynucleotide encoding a biologically active PSP1 polypeptide.

Another aspect of the invention is an isolated polynucleotide selected from the group consisting of:
 (a) a polynucleotide encoding PSP1-1 having the nucleotide sequence as set forth in SEQ ID NO: 24 from nucleotide 603 to 1979; and
 (b) a polynucleotide substantially similar to SEQ ID NO: 24.

Another aspect of the invention is an isolated polynucleotide selected from the group consisting of:
 (a) a polynucleotide encoding PSP1-2 having the nucleotide sequence as set forth in SEQ ID NO: 23 from nucleotide 603 to 1979; and
 (b) a polynucleotide substantially similar to SEQ ID NO: 23.

Another aspect of the invention is an isolated polynucleotide selected from the group consisting of:
 (a) a polynucleotide encoding PSP1-3 having the nucleotide sequence as set forth in SEQ ID NO: 26 from nucleotide 603 to 1736; and
 (b) a polynucleotide substantially similar to SEQ ID NO: 26.

Another aspect of the invention is an isolated polynucleotide selected from the group consisting of:
 (a) a polynucleotide encoding PSP1-4 having the nucleotide sequence as set forth in SEQ ID NO: 28 from nucleotide 603 to 1913; and
 (b) a polynucleotide substantially similar to SEQ ID NO: 28.

In a further aspect the invention provides any isolated polynucleotide as above defined wherein nucleotides 672 and 1435 are independently selected from C and T. hereinafter referred to as 'polymorphic variants'.

Another aspect of the invention is the functional polypeptides encoded by the polynucleotides of the invention.

Another aspect of the invention is an antisense oligonucleotide comprising a sequence which is capable of binding to the polynucleotides of the invention or D87258.

Another aspect of the invention is modulators of the polypeptides of the invention or of D87258.

Another aspect of the invention is a method for assaying a medium for the presence of a substance that modulates PSP1 or D87258 activity by affecting the binding of PSP1 or D87258 to cellular binding partners comprising the steps of:
 (a) providing a PSP1 or D87258 protein having the amino acid sequence of PSP1-1, PSP1-2, PSP1-3 or PSP1-4 or D87258, or a functional derivative or polymorphic variant thereof and a cellular binding partner or synthetic analog thereof;
 (b) incubating with a test substance which is suspected of modulating PSP1 or D87258 activity under conditions which permit the formation of a PSP1 or D87258 protein/cellular binding partner complex;
 (c) assaying for the presence of the complex, free PSP1 or D87258 protein or free cellular binding partner; and
 (d) comparing to a control to determine the effect of the substance.

Another aspect of the invention is a method for assaying a medium for the presence of a substance that modulates PSP1 or D87258 activity by inhibiting proteolytic activity on a cellular substrate comprising the steps of:
 (a) providing a PSP1 or D87258 protein having the amino acid sequence of PSP1-1, PSP1-2, PSP1-3 or PSP1-4 or D87258, or a functional fragment or polymorphic variant thereof and a cellular substrate or synthetic analog thereof;
 (b) incubating with a test substance which is suspected of inhibiting PSP1 or D87258 activity under conditions which permit the formation of a PSP1 enzyme/substrate complex and subsequent cleavage of the substrate;
 (c) assaying for the presence of proteolytically cleaved substrate; and
 (d) comparing to a control to determine the effect of the substance.

Another aspect of the invention is a method for assaying for the presence of a substance that modulates PSP1 or D87258 activity by direct binding to PSP1 or D87258 protein comprising the steps of:

(a) providing a labelled PSP1 or D87258 protein having the amino acid sequence of PSP1-1, PSP1-2, PSP1-3 or PSP1-4 or D87258 or a functional derivative or polymorphic variant thereof;

(b) providing solid support-associated modulator candidates;

(c) incubating a mixture of the labelled PSP1 or D87258 protein with the support-associated modulator candidates under conditions which can permit the formation of a PSP1 protein/modulator candidate complex;

(d) separating the solid support from free soluble labelled PSP1 or D87258 protein;

(e) assaying for the presence of solid support-associated labelled protein;

(f) isolating the solid support complexed with labelled PSP1 or D87258 protein; and (g) identifying the modulator candidate.

Another aspect of the invention is PSP1 or D87258 protein modulating compounds identified by the methods of the invention.

Another aspect of the invention is a method for the treatment of a patient having need to modulate PSP1 or D87258 activity comprising administering to the patient a therapeutically effective amount of the modulating compounds of the invention.

Another aspect of the invention is a method of diagnosing conditions associated with PSP1 or D87258 protein deficiency which comprises:

(a) isolating a polynucleotide sample from an individual;

(b) assaying the polynucleotide sample and a polynucleotide of the invention encoding PSP1 or D87258; and (c) comparing differences between the polynucleotide sample and the PSP1 or D87258 polynucleotide, wherein any differences indicate mutations in the PSP1 or D87258 sequence.

Another aspect of the invention is a method of treating conditions which are related to insufficient PSP1 or D87258 protein function which comprises:

(a) isolating cells from a patient deficient in PSP1 or D87258 protein function;

(b) altering the cells by transfecting the polynucleotide of the invention or D87258 into the cells wherein a PSP1 or D87258 protein is expressed; and (c) introducing the cells back to the patient to alleviate the condition.

Another aspect of the invention is a method of treating conditions which are related to insufficient PSP1 or D87258 protein function which comprises administering the polynucleotide of the invention to a patient deficient in PSP1 protein function wherein a PSP1 or D87258 protein is expressed and alleviates the condition.

Another aspect of the invention is an antibody immunoreactive with PSP1 or D87258 or an immunogen thereof.

Another aspect of the invention is a transgenic non-human animal capable of expressing in any cell thereof the polynucleotide of the invention.

Another aspect of the invention is a method for determining the genetic predisposition to neurodegeneration in a patient comprising detecting PSP1 or D87258 polymorphisms in a sample from a patient.

Yet another aspect of the invention is isolated polynucleotide having the nucleotide sequence as set forth in SEQ ID NO: 32, 33, 34, 35, 36, 37, 38, 39, or 40.

BRIEF DESCRIPTION OF THE FIGURES

FIG. 1 is an amino acid sequence alignment of PSP1-1 with E. coli htrA.

FIG. 2 is a multiple cDNA sequence alignment of the PSP1 isolates PSP1-1, PSP1-2, PSP1-3 and PSP1-4.

FIG. 3 is an amino acid sequence alignment of PSP1-1 with a putative human serine protease.

DETAILED DESCRIPTION OF THE INVENTION

As used herein, the term "PSP1 polynucleotide" or "PSP1" refers to DNA molecules comprising a nucleotide sequence that encodes PSP1 and alternative splice variants, i.e., homologs and isoforms, and polymorphic variants. PSP1 binds to a region encompassing amino acids 269–413 of the human PS-1 protein, contains a conserved serine protease motif and exhibits homology to the E. coli serine protease htrA described by Lipinska et al. in *Nucl. Acids Res.* 16, 10053–10066 (1988) and a putative human serine protease with an IGF-binding motif (Ohno, I., et al., Genbank Accession No. D87258 (1996)), hereinafter referred to as D87258.

The PSP1-1 sequence is listed in SEQ ID NO: 24. The coding region of this sequence consists of nucleotides 603–1979 of SEQ ID NO: 24. The deduced 458 amino acid sequence of the encoded product PSP1-1 is listed in SEQ ID NO: 25.

The PSP1-1 sequence listed in SEQ ID NO: 30 includes two polymorphic variants, at nucleotides 672 (C/T) and 1435 (C/T) resulting in alternative amino acid residues at position 24 (arg/cys) and 278 (ala/val), both in the conserved region of nucleotides 1–1540. The deduced 458 amino acid sequence of the encoded product PSP1-1 is listed in SEQ ID NO: 31.

The PSP1-2 sequence is listed in SEQ ID NO: 23. The coding region of this sequence consists of nucleotides 603–1979 of SEQ ID NO: 23. The deduced 458 amino acid sequence of the encoded product PSP1-2 is listed in SEQ ID NO: 8. The PSP1-3 sequence is listed in SEQ ID NO: 26. The coding region of this sequence consists of nucleotides 603–1736 of SEQ ID NO: 26. The deduced 377 amino acid sequence of the encoded product PSP1-3 is listed in SEQ ID NO: 27. The PSP1-4 sequence is listed in SEQ ID NO: 28. The coding region of this sequence consists of nucleotides 603–1913 of SEQ ID NO: 28. The deduced 436 amino acid sequence of the encoded product PSP1-4 is listed in SEQ ID NO: 29.

The D87258 sequence is listed in SEQ ID NO: 17. The coding region of this sequence consists of nucleotides 49–1491 of SEQ ID NO: 17. The deduced 480 amino acid sequence of the encoded product D87258 is listed in SEQ ID NO: 18. The D87258 sequence listed in SEQ ID NO: 17 includes a polymorphic variant at nucleotide 1325 (G/T) resulting in alternative amino acid residues at position 213 (gly/val). The sequence in Genbank Accession No. D87258 (1996), describes only 1325G. The novel polynucleotide polymorph of D87258 having 1325T, is hereinafter referred to as D87258 (1325T) and the novel encoded product having valine at 213 is D87258 (1325T) protein. The novel polynucleotide D87258 (1325T) and its encoded protein can replace PSP-1 in any of the composition, uses or methods herein described and such novel polypeptide, encoded protein, compositions, uses and methods also form part of the invention.

As used herein, the term "functional fragments" when used to modify a specific gene or gene product means a less than full length portion of the gene or gene product which retains substantially all of the biological function associated with the full length gene or gene product to which it relates. An example of a functional fragment of PSP1 is the minimal catalytic domain. To determine whether a fragment of a particular gene or gene product is a functional fragment, fragments are generated by well-known nucleolytic or proteolytic techniques or by the polymerase chain reaction and the fragments tested for the described biological function.

As used herein, an "antigen" refers to a molecule containing one or more epitopes that will stimulate a host's immune system to make a humoral and/or cellular antigen-specific response. The term is also used herein interchangeably with "immunogen."

As used herein, the term "epitope" refers to the site on an antigen or hapten to which a specific antibody molecule binds. The term is also used herein interchangeably with "antigenic determinant" or "antigenic determinant site."

As used herein, "monoclonal antibody" is understood to include antibodies derived from one species (e.g., murine, rabbit, goat, rat, human, etc.) as well as antibodies derived from two (or perhaps more) species (e.g., chimeric and humanized antibodies).

As used herein, a coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequence is ultimately processed to produce the desired protein.

As used herein, "recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

As used herein, a "replicon" is any genetic element (e.g., plasmid, chromosome, virus) that functions as an autonomous unit of DNA replication in vivo; i.e., capable of replication under its own control.

As used herein, a "vector" is a replicon, such as a plasmid, phage, or cosmid, to which another DNA segment may be attached so as to bring about the replication of the attached segment.

As used herein, a "reference" gene refers to the wild type PSP1 sequence of the invention and is understood to include the various sequence polymorphisms that exist, wherein nucleotide substitutions in the gene sequence exist, but do not affect the essential function of the gene product.

As used herein, a "mutant" gene refers to PSP1 sequences different from the reference gene wherein nucleotide substitutions and/or deletions and/or insertions result in perturbation of the essential function of the gene product.

As used herein, a DNA "coding sequence of" or a "nucleotide sequence encoding" a particular protein, is a DNA sequence which is transcribed and translated into a polypeptide when placed under the control of appropriate regulatory sequences.

As used herein, a "promoter sequence" is a DNA regulatory region capable of binding RNA polymerase in a cell and initiating transcription of a downstream (3' direction) coding sequence. For purposes of defining the present invention, the promoter sequence is bound at its 3' terminus by a translation start codon (e.g., ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease Si), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

As used herein, DNA "control sequences" refers collectively to promoter sequences, ribosome binding sites, polyadenylation signals, transcription termination sequences, upstream regulatory domains, enhancers and the like, which collectively provide for the expression (i.e., the transcription and translation) of a coding sequence in a host cell.

As used herein, a control sequence "directs the expression" of a coding sequence in a cell when RNA polymerase will bind the promoter sequence and transcribe the coding sequence into mRNA, which is then translated into the polypeptide encoded by the coding sequence.

As used herein, a "host cell" is a cell which has been transformed or transfected, or is capable of transformation or transfection by an exogenous DNA sequence.

As used herein, a cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cells containing the exogenous DNA.

As used herein, "transfection" or "transfected" refers to a process by which cells take up foreign DNA and integrate that foreign DNA into their chromosome. Transfection can be accomplished, for example, by various techniques in which cells take up DNA (e.g., calcium phosphate precipitation, electroporation, assimilation of liposomes, etc.) or by infection, in which viruses are used to transfer DNA into cells.

As used herein, a "target cell" is a cell that is selectively transfected over other cell types (or cell lines).

As used herein, a "clone" is a population of cells derived from a single cell or common ancestor by mitosis. A "cell line" is a clone of a primary cell that is capable of stable growth in vitro for many generations.

As used herein, a "heterologous" region of a DNA construct is an identifiable segment of DNA within or attached to another DNA molecule that is not found in association with the other molecule in nature. Thus, when the heterologous region encodes a gene, the gene will usually be flanked by DNA that does not flank the gene in the genome of the source animal. Another example of a heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

As used herein, a "modulator" of a polypeptide is a substance which can affect the polypeptide function, such as an inhibitor of enzymatic activity.

An aspect of the present invention is isolated polynucleotides encoding a PSP1 protein and substantially similar sequences. Isolated polynucleotide sequences are substantially similar if they are capable of hybridizing under moderately stringent conditions to SEQ ID NOs: 23, 24, 26 or 28 or they encode DNA sequences which are degenerate to SEQ ID NOs: 23, 24, 26 or 28 or are degenerate to those sequences capable of hybridizing under moderately stringent conditions to SEQ ID NOs: 23, 24, 26 or 28.

Moderately stringent conditions is a term understood by the skilled artisan and has been described in, for example, Sambrook et al. *Molecular Cloning: A Laboratory Manual*, 2nd edition, Vol. 1, pp. 101–104, Cold Spring Harbor Laboratory Press (1989). An exemplary hybridization protocol using moderately stringent conditions is as follows. Nitrocellulose filters are prehybridized at 65° C. in a solution containing 6× SSPE, 5× Denhardt's solution (10 g Ficoll, 10 g BSA and 10 g polyvinylpyrrolidone per liter solution), 0.05% SDS and 100 ug/ml tRNA. Hybridization probes are labeled, preferably radiolabelled (e.g., using the Bios TAG-IT® kit). Hybridization is then carried out for approximately 18 hours at 65° C. The filters are then washed twice in a solution of 2× SSC and 0.5% SDS at room temperature for 15 minutes. Subsequently, the filters are washed at 58° C., air-dried and exposed to X-ray film overnight at –70° C. with an intensifying screen.

Degenerate DNA sequences encode the same amino acid sequence as SEQ ID NOs: 8, 25, 27 or 29 or the proteins encoded by that sequence capable of hybridizing under moderately stringent conditions to SEQ ID NOs: 8, 25, 27, 29, but have variation(s) in the nucleotide coding sequences because of the degeneracy of the genetic code. For example, the degenerate codons UUC and UUU both code for the amino acid phenylalanine, whereas the four codons GGX, where X=U, C, A, or G, all code for glycine.

Alternatively, substantially similar sequences are defined as those nucleotide sequences encoding proteins having PSP1 activity in which about 70%, preferably about 80%, and most preferably about 90%, of the nucleotides share identity with PSP1, i.e., a sequence encoding a protein having PSP1 activity is substantially similar to any of SEQ ID NOs: 23, 24, 26 or 28 when at least about 70% of all of the nucleotides of the sequence match SEQ ID NOs: 23, 24, 26 or 28. Nucleotide sequences that are substantially similar can be identified by hybridization or by sequence comparison.

Embodiments of the isolated polynucleotides of the invention include DNA, genomic DNA and RNA, preferably of human origin. A method for isolating a nucleic acid molecule encoding a PSP1 protein is to probe a genomic or cDNA library with a natural or artificially designed probe using art recognized procedures. See, e.g., "Current Protocols in Molecular Biology", Ausubel et al. (eds.) Greene Publishing Association and John Wiley Interscience, New York, 1989,1992. The ordinarily skilled artisan will appreciate that SEQ ID NOs: 23, 24, 26 or 28 or fragments thereof comprising at least 15 contiguous nucleotides are particularly useful probes. It is also appreciated that such probes can be and are preferably labeled with an analytically detectable reagent to facilitate identification of the probe. Useful reagents include, but are not limited to, radioisotopes, fluorescent dyes or enzymes capable of catalyzing the formation of a detectable product. The probes would enable the ordinarily skilled artisan to isolate complementary copies of genomic DNA, cDNA or RNA polynucleotides encoding PSP1 proteins from human, mammalian or other animal sources or to screen such sources for related sequences, e.g., additional members of the family, type and/or subtype, including transcriptional regulatory and control elements as well as other stability, processing, translation and tissue specificity-determining regions from 5' and/or 3' regions relative to the coding sequences disclosed herein, all without undue experimentation.

Another aspect of the invention is functional polypeptides encoded by the polynucleotides of the invention and substantially similar polypeptides. An embodiment of a functional polypeptide of the invention is the PSP1 protein having the amino acid sequence set forth in SEQ ID NO: 8, 25, 27 or 29.

Polypeptide sequences that are substantially similar are those sequences having PSP1 activity in which about 50%, preferably 70%, and most preferably about 90%, of the amino acids share identity with PSP1, i.e., a sequence representing a polypeptide having PSP1 activity is substantially similar to any of SEQ ID NOs: 8, 24, 26 or 28 when at least about 50% of all of the amino acids of the sequence match SEQ ID NOs: 8, 25, 27 or 29. Substantially similar polypeptide sequences can be identified by techniques such as proteolytic digestion, gel electrophoresis, microsequencing and/or sequence comparison, e.g., through use of the GAP algorithm available from the University of Wisconsin Genetics Computer Group.

Another aspect of the invention is a method for preparing essentially pure PSP1 protein. Yet another aspect is the PSP1 protein produced by the preparation method of the invention. This protein has the amino acid sequence listed in SEQ ID NOs: 8, 25, 27 or 29 and includes variants with a substantially similar amino acid sequence that have the same function. The proteins of this invention are preferably made by recombinant genetic engineering techniques by culturing a recombinant host cell containing a vector encoding the polynucleotides of the invention under conditions promoting the expression of the protein and recovery thereof.

The isolated polynucleotides, particularly the DNAs, can be introduced into expression vectors by operatively linking the DNA to the necessary expression control regions, e.g., regulatory regions, required for gene expression. The vectors can be introduced into an appropriate host cell such as a prokaryotic, e.g., bacterial, or eukaryotic, e.g., yeast or mammalian cell by methods well known in the art. See Ausubel et al., supra. The coding sequences for the desired proteins, having been prepared or isolated, can be cloned into any suitable vector or replicon. Numerous cloning vectors are known to those of skill in the art and the selection of an appropriate cloning vector is a matter of choice. Examples of recombinant DNA vectors for cloning and host cells which they can transform include, but are not limited to, the bacteriophage (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), a baculovirus insect cell system, a Drosophila insect system, YCp19 (Saccharomyces) and pSV2neo (mammalian cells). See generally, "DNA Cloning": Vols. I & II, Glover et al. ed. IRL Press Oxford (1985) (1987); and T. Maniatis et al. ("Molecular Cloning" Cold Spring Harbor Laboratory (1982).

The gene can be placed under the control of control elements such as a promoter, ribosome binding site (for bacterial expression) and, optionally, an operator, so that the DNA sequence encoding the desired protein is transcribed into RNA in the host cell transformed by a vector containing the expression construct. The coding sequence may or may not contain a signal peptide or leader sequence. The proteins of the present invention can be expressed using, for example, the E. coli tac promoter or the protein A gene (spa) promoter and signal sequence. Leader sequences can be removed by the bacterial host in post-translational processing. See, e.g., U.S. Pat. Nos. 4,431,739; 4,425,437 and 4,338,397.

In addition to control sequences, it may be desirable to add regulatory sequences which allow for regulation of the expression of the protein sequences relative to the growth of the host cell. Regulatory sequences are known to those of skill in the art. Exemplary are those which cause the expression of a gene to be turned on or off in response to a chemical or physical stimulus, including the presence of a regulatory compound or to various temperature or metabolic conditions. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences, i.e., RNA polymerase which binds to the DNA molecule at the control sequences transcribes the coding sequence. Modification of the sequences encoding the particular antigen of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to produce mutants or analogues of PSP1 protein. Mutants or analogues may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., T. Maniatis et al., supra; "DNA Cloning," Vols. I and II, supra; and "Nucleic Acid Hybridization", supra.

Depending on the expression system and host selected, the proteins of the present invention are produced by growing host cells transformed by an expression vector described above under conditions whereby the protein of interest is expressed. Preferred mammalian cells include human embryonic kidney cells (293), monkey kidney cells, fibroblast (COS) cells, Chinese hamster ovary (CHO) cells, Drosophila or murine L-cells. If the expression system secretes the protein into growth media, the protein can be purified directly from the media. If the protein is not secreted, it is isolated from cell lysates or recovered from the cell membrane fraction. The selection of the appropriate growth conditions and recovery methods are within the skill of the art.

An alternative method to identify proteins of the present invention is by constructing gene libraries, using the resulting clones to transform E. coli and pooling and screening individual colonies using polyclonal serum or monoclonal antibodies to PSP1.

The proteins of the present invention may also be produced by chemical synthesis such as solid phase peptide synthesis on an automated peptide synthesizer, using known amino acid sequences or amino acid sequences derived from the DNA sequence of the genes of interest. Such methods are known to those skilled in the art.

The proteins of the present invention or their immunogenic fragments comprising at least one epitope can be used to produce antibodies, both polyclonal and monoclonal, directed to epitopes corresponding to amino acid sequences disclosed herein. If polyclonal antibodies are desired, a selected mammal such as a mouse, rabbit, goat or horse is immunized with a protein of the present invention, or its fragment, or a mutant protein. Serum from the immunized animal is collected and treated according to known procedures. Serum polyclonal antibodies can be purified by immunoaffinity chromatography or other known procedures.

Monoclonal antibodies to the proteins of the present invention, and to the immunogenic fragments thereof, can also be readily produced by one skilled in the art. The general methodology for making monoclonal antibodies by using hybridoma technology is well known. Immortal antibody-producing cell lines can be created by cell fusion and also by other techniques such as direct transformation of B lymphocytes with oncogenic DNA or transfection with Epstein-Barr virus. See, e.g., M. Schreier et al., "Hybridoma Techniques" (1980); Hammerling et al., "Monoclonal Antibodies and T-cell Hybridomas" (1981); Kennett et al., "Monoclonal Antibodies" (1980); and U.S. Pat. Nos. 4,341,761; 4,399,121; 4,427,783; 4,444,887; 4,452,570; 4,466,917; 4,472,500; 4,491,632; and 4,493,890. Panels of monoclonal antibodies produced against the antigen of interest, or fragment thereof, can be screened for various properties, i.e., for isotype, epitope, affinity, etc. Monoclonal antibodies are useful in purification, using immunoaffinity techniques, of the individual antigens which they are directed against. Alternatively, genes encoding the monoclonals of interest may be isolated from the hybridomas by PCR techniques known in the art and cloned and expressed in the appropriate vectors. The antibodies of this invention, whether polyclonal or monoclonal have additional utility in that they may be employed as reagents in immunoassays, RIA, ELISA, and the like. The antibodies of the invention can be labeled with an analytically detectable reagent such as a radioisotope, fluorescent molecule or enzyme.

Chimeric antibodies, in which non-human variable regions are joined or fused to human constant regions (see, e.g., Liu et al., Proc. Natl Acad. Sci. USA, 84, 3439 (1987)), may also be used in assays or therapeutically. Preferably, a therapeutic monoclonal antibody would be "humanized" as described in Jones et al., Nature, 321, 522 (1986); Verhoeyen et al., Science, 239, 1534 (1988); Kabat et al., J. Immunol., 147, 1709 (1991); Queen et al., Proc. Natl Acad. Sci. USA, 86, 10029 (1989); Gorman et al., Proc. Natl Acad. Sci. USA, 88, 34181 (1991); and Hodgson et al., Bio/Technology, 9:, 421 (1991).

Another aspect of the present invention is modulators of the polypeptides of the invention or of D87258. Functional modulation of PSP1 or D87258 by a substance includes partial to complete inhibition of function, such as inhibition of proteolytic activity, identical function, as well as enhancement of function. Embodiments of modulators of the invention include peptides, oligonucleotides and small organic molecules including peptidomimetics. Modulators of the invention may be useful as therapeutics or prophylactics for all forms of neurodegeneration including AD. Modulators of PSP1 or D87258 proteolytic activity relative to other endogenous substrates may be also be useful for the treatment of other types of human disease states.

Another aspect of the invention is antisense oligonucleotides comprising a sequence which is capable of binding to the polynucleotides of the invention. Synthetic oligonucleotides or related antisense chemical structural analogs can be designed to recognize, specifically bind to and prevent transcription of a target nucleic acid encoding PSP1 or D87258 protein by those of ordinary skill in the art. See generally, Cohen, J. S., *Trends in Pharm. Sci.,* 10, 435(1989) and Weintraub, H. M., *Scientific American,* January (1990) at page 40.

Another aspect of the invention is a method for assaying a medium for the presence of a substance that modulates PSP1 or D87258 protein function by affecting the binding of PSP1 or D87258 protein to cellular binding partners. Examples of modulators include, but are not limited to peptides and small organic molecules including peptidomimetics. A PSP1 or D87258 protein is provided having the amino acid sequence of PSP1 (SEQ ID NOs: 8, 25, 27 or 29) or D87258 (SEQ ID NO: 18) or a functional fragment thereof together with a cellular binding partner or synthetic analog thereof. The mixture is incubated with a test substance which is suspected of modulating PSP1 or D87258 activity, under conditions which permit the formation of a PSP1 or D87258 gene product/cellular binding partner complex. An assay is performed for the presence of the complex, free PSP1 or D87258 protein or free cellular binding partner and the result compared to a control to determine the effect of the test substance.

Another aspect of the invention is a method for assaying a medium for the presence of a substance that modulates PSP1 or D87258 protein function by inhibiting its proteolytic activity on cellular substrates. Examples of modulators include, but are not limited to peptides and small organic molecules including peptidomimetics. Cellular substrates can include PS-1, PS-2, APP or other substrates. A PSP1 or D87258 protein is provided having the amino acid sequence of PSP1 (SEQ ID NOs: 8, 25, 27 or 29) or D87258 (SEQ ID NO: 18) or a functional fragment thereof together with a cellular substrate or synthetic analog thereof. The mixture is incubated with a test substance which is suspected of inhibiting PSP1 or D87258 activity, under conditions which permit the formation of a PSP1 or D87258 enzyme/substrate complex and subsequent cleavage of the substrate.

Another aspect of the invention is a method for assaying for the presence of a substance that modulates PSP1 or D87258 activity by direct binding to PSP1 or D87258 protein. Examples of modulators include, but are not limited to, peptides and small organic molecules including peptidomimetics. Modulator candidates are synthesized on a solid support by techniques such as those disclosed in Lam et al., *Nature* 354, 82 (1991) or Burbaum et al., *Proc. Natl. Acad. Sci. USA* 92, 6027 (1995) to provide solid support-associated modulator candidates. A labelled PSP1 or D87258 protein is provided having the amino acid sequence of PSP1 (SEQ ID NOs: 8, 25, 27 or 29) or D87258 (SEQ ID NO: 18) or a functional derivative thereof. Exemplary labels include directly attached fluorescent or colored dyes, biotin, radioisotopes or epitope tags, which are detectable by a suitable antibody. A mixture of solid support-associated modulator candidates and labelled PSP1 or D87258 protein is incubated under conditions which can permit the formation of a PSP1 or D87258 protein/modulator candidate complex. The solid support is separated from free soluble labelled PSP1 or D87258 protein. An assay is performed for the presence of solid support-associated labelled protein. Solid supports complexed with labelled protein are isolated and the identity of the modulator candidate determined by techniques well known to those skilled in the art, such as the TOF-SIMS method in Brummel et al., *Science* 264, 399–402 (1994).

Modulation of PSP1 or D87258 function would be expected to have effects on presenilin cleavage, the cleavage of other proteins or βA4 production. Any modulators so identified would be expected to be useful as a therapeutic for the treatment and prevention of neurodegeneration including FAD and AD.

Further, PSP1 or D87258 could be used to isolate proteins which interact with it and this interaction could be a target for interference. Inhibitors of protein-protein interactions between PSP1 or D87258 and other factors could lead to the development of pharmaceutical agents for the modulation of PSP1 or D87258 activity.

Methods to assay for protein-protein interactions, such as that of a PSP1 or D87258 gene product/binding partner complex, and to isolate proteins interacting with PSP1 or D87258 are known to those skilled in the art. Use of the methods discussed below enable one of ordinary skill in the art to accomplish these aims without undue experimentation.

The yeast two-hybrid system provides methods for detecting the interaction between a first test protein and a second test protein, in vivo, using reconstitution of the activity of a transcriptional activator. The method is disclosed in U.S. Pat. No. 5,283,173; reagents are available from Clontech and Stratagene. Briefly, PSP1 cDNA is fused to a Gal4 or LexA transcription factor DNA binding domain and expressed in yeast cells. cDNA library members obtained from cells of interest are fused to a transactivation domain of Gal4 or another transactivation domain. cDNA clones which express proteins which can interact with PSP1 will lead to reconstitution of transcription factor activity such as Gal4 and transactivation of a reporter gene expression such as Gal1-lacZ.

An alternative method is screening of λgt11, λZAP (Stratagene) or equivalent cDNA expression libraries with recombinant PSP1. Recombinant PSP1 protein or fragments thereof are fused to small peptide tags such as FLAG, HSV or GST. The peptide tags can possess convenient phosphorylation sites for a kinase such as heart muscle creatine kinase or they can be biotinylated. Recombinant PSP1 can be phosphorylated with $^{32}$[P] or used unlabeled and detected with streptavidin or antibodies against the tags. λgt11cDNA expression libraries are made from cells of interest and are incubated with the recombinant PSP1, washed and cDNA clones isolated which interact with PSP1. See, e.g., T. Maniatis et al., supra.

Another method is the screening of a mammalian expression library in which the cDNAs are cloned into a vector between a mammalian promoter and polyadenylation site and transiently transfected in COS or 293 cells followed by detection of the binding protein 48 hours later by incubation of fixed and washed cells with a labelled PSP1, prefereably iodinated, and detection of bound PSP1 by autoradiography (See Sims et al., *Science* 241, 585–589 (1988) and McMahan et al., *EMBO J.* 10, 2821–2832 (1991)). In this manner, pools of cDNAs containing the cDNA encoding the binding protein of interest can be selected and the cDNA of interest can be isolated by further subdivision of each pool followed by cycles of transient transfection, binding and autoradiography. Alternatively, the cDNA of interest can be isolated by transfecting the entire cDNA library into mammalian cells and panning the cells on a dish containing PSP1 bound to the plate. Cells which attach after washing are lysed and the plasmid DNA isolated, amplified in bacteria, and the cycle of transfection and panning repeated until a single cDNA clone is obtained (See Seed et al, *Proc. Natl. Acad. Sci. USA* 84, 3365 (1987) and Aruffo et al., *EMBO J.* 6, 3313 (1987)). If the binding protein is secreted, its cDNA can be obtained by a similar pooling strategy once a binding or neutralizing assay has been established for assaying supernatants from transiently transfected cells. General methods for screening supernatants are disclosed in Wong et al., *Science* 228, 810–815 (1985).

Another alternative method is isolation of proteins interacting with PSP1 directly from cells. Fusion proteins of PSP1 with GST or small peptide tags are made and immobilized on beads. Biosynthetically labeled or unlabeled protein extracts from the cells of interest are prepared, incubated with the beads and washed with buffer. Proteins interacting with PSP1 are eluted specifically from the beads and analyzed by SDS-PAGE. Binding partner primary amino acid sequence data are obtained by microsequencing. Optionally, the cells can be treated with agents that induce a functional response such as tyrosine phosphorylation of cellular proteins. An example of such an agent would be a growth factor or cytokine such as erythropoietin or interleukin-3.

Another alternative method is immunoaffinity purification. Recombinant PSP1 is incubated with labeled or unlabeled cell extracts and immunoprecipitated with anti-PSP1 antibodies. The immunoprecipitate is recovered with protein A-Sepharose and analyzed by SDS-PAGE. Unlabelled proteins are labeled by biotinylation and detected on SDS gels with streptavidin. Binding partner proteins are analyzed by microsequencing. Further, standard biochemical purification steps known to those skilled in the art may be used prior to microsequencing.

Yet another alternative method is screening of peptide libraries for binding partners. Recombinant tagged or labeled PSP1 is used to select peptides from a peptide or phosphopeptide library which interact with PSP1. Sequencing of the peptides leads to identification of consensus peptide sequences which might be found in interacting proteins.

PSP1 or D87258 binding partners identified by any of these methods or other methods which would be known to those of ordinary skill in the art as well as those putative binding partners discussed above can be used in the assay method of the invention. Assaying for the presence of PSP1 or D87258/binding partner complex are accomplished by, for example, the yeast two-hybrid system, ELISA or immunoassays using antibodies specific for the complex. In the presence of test substances which interrupt or inhibit formation of PSP1 or D87258/binding partner interaction, a decreased amount of complex will be determined relative to a control lacking the test substance.

Assays for free PSP1 or D87258, or binding partner are accomplished by, for example, ELISA or immunoassay using specific antibodies or by incubation of radiolabeled PSP1 or D87258 with cells or cell membranes followed by centrifugation or filter separation steps. In the presence of test substances which interrupt or inhibit formation of PSP1 or D87258/binding partner interaction, an increased amount of free PSP1 or D87258, or free binding partner will be determined relative to a control lacking the test substance.

Another aspect of the invention is pharmaceutical compositions comprising an effective amount of a PSP1 or D87258 modulator of the invention and a pharmaceutically acceptable carrier. Pharmaceutical compositions of modulators of this invention for parenteral administration, i.e., subcutaneously, intramuscularly or intravenously or oral administration can be prepared.

The compositions for parenteral administration will commonly comprise a solution of the modulators of the invention or a cocktail thereof dissolved in an acceptable carrier, preferably an aqueous carrier. A variety of aqueous carriers may be employed, e.g., water, buffered water, 0.4% saline, 0.3% glycine and the like. These solutions are sterile and generally free of particulate matter. These solutions may be sterilized by conventional, well-known sterilization techniques. The compositions may contain pharmaceutically acceptable auxiliary substances as required to approximate physiological conditions such as pH adjusting and buffering agents, etc. The concentration of the modulator of the invention in such pharmaceutical formulation can vary widely, i.e., from less than about 0.5%, usually at or at least about 1% to as much as 15 or 20% by weight and will be selected primarily based on fluid volumes, viscosities, etc. according to the particular mode of administration selected.

Thus, a pharmaceutical composition of the modulator of the invention for intramuscular injection could be prepared to contain 1 mL sterile buffered water, and 50 mg of a protein of the invention. Similarly, a pharmaceutical composition of the modulator of the invention for intravenous infusion could be made up to contain 250 mL of sterile Ringer's solution, and 150 mg of a modulator of the invention. Actual methods for preparing parenterally administrable compositions are well known or will be apparent to those skilled in the art and are described in more detail in, for example, *Remington's Pharmaceutical Science,* 15th ed., Mack Publishing Company, Easton, Pa.

The physician will determine the dosage of the present therapeutic agents which will be most suitable and it will vary with the form of administration and the particular compound chosen, and furthermore, it will vary with the particular patient under treatment. Generally, the physician will wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The therapeutic dosage will generally be from 0.1 to 1000 milligrams per day and higher although it may be administered in several different dosage units.

Depending on the patient condition, the pharmaceutical composition of the invention can be administered for prophylactic and/or therapeutic treatments. In therapeutic applications, compositions containing the present compounds or a cocktail thereof are administered to a patient already suffering from a disease in an amount sufficient to cure or at least partially arrest the disease and its complications. In prophylactic applications, compositions containing the present compounds or a cocktail thereof are administered to a patient not already in a disease state to enhance the patient's resistance to the disease.

Single or multiple administrations of the pharmaceutical compositions can be carried out with dose levels and pattern being selected by the treating physician. In any event, the pharmaceutical composition of the invention should provide a quantity of the modulators of the invention sufficient to effectively treat the patient.

Additionally, some diseases result from inherited defective genes. These genes can be detected by comparing the sequence of the defective gene with that of a normal one. Individuals carrying mutations in the PSP1 or D87258 gene may be detected at the DNA level by a variety of techniques. Nucleic acids used for diagnosis (genomic DNA, mRNA, etc.) may be obtained from a patient's cells, such as from blood, urine, saliva or tissue biopsy, e.g., chorionic villi sampling or removal of amniotic fluid cells and autopsy material. The genomic DNA may be used directly for detection or may be amplified enzymatically by using PCR, ligase chain reaction (LCR), strand displacement amplification (SDA), etc. prior to analysis. See, e.g., Saiki et al., Nature, 324, 163–166 (1986), Bej, et al., Crit. Rev. Biochem. Molec. Biol., 26, 301–334 (1991), Birkenmeyer et al., J. Virol. Meth., 35, 117–126 (1991), Van Brunt, J., Bio/Technology, 8, 291–294 (1990)). RNA or cDNA may also be used for the same purpose. As an example, PCR primers complementary to the nucleic acid of the instant invention can be used to identify and analyze PSP1 or D87258 mutations. For example, deletions and insertions can be detected by a change in size of the amplified product in comparison to the normal PSP1 or D87258 genotype. Point mutations can be identified by hybridizing amplified DNA to rabiolabeled PSP1 or D87258 RNA of the invention or alternatively, radiolabelled PSP1 or D87258 antisense DNA sequences of the invention. Perfectly matched sequences can be distinguished from mismatched duplexes by RNase A digestion or by differences in melting temperatures (Tm). Such a diagnostic would be particularly useful for prenatal and even neonatal testing.

In addition, point mutations and other sequence differences between the reference gene and "mutant" genes can be identified by yet other well-known techniques, e.g., direct DNA sequencing, single-strand conformational polymorphism. See Orita et al., Genomics, 5, 874–879 (1989). For example, a sequencing primer is used with double-stranded PCR product or a single-stranded template molecule generated by a modified PCR. The sequence determination is performed by conventional procedures with radiolabeled nucleotides or by automatic sequencing procedures with fluorescent-tags. Cloned DNA segments may also be used as probes to detect specific DNA segments. The sensitivity of this method is greatly enhanced when combined with PCR. Further, point mutations and other sequence variations, such as polymorphisms, can be detected as described above, e.g., through the use of allele-specific oligonucleotides for PCR amplification of sequences that differ by single nucleotides. Oligonucleotides having sequences as set forth in SEQ ID Nos: 32, 33, 34, 35, 36, 37, 38, 39 and 40 are useful in such a method.

These methods are useful for determining the genetic predisposition to neurodegeneration in a patient by detecting polymorphisms within PSP1 or D87258 in a sample from a patient. Preferably, the polymorphisms detected are at nucleotide 672 of PSP1, at nucleotide 1435 of PSP1 or at nucleotide 1325 of D87258. Preferably, the polymorphisms are detected by PCR; most preferably, the polymorphisms are detected by PCR with oligonucleotides having a nucleotide sequence selected from the group consisting of SEQ ID NOs: 32, 33, 34, 35, 36, 37, 38, 39 and 40. Preferably, the neurodegeneration predisposition determined is to Alzheimer's disease.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures. See, e.g., Myers et al., Science, 230, 1242 (1985). In addition, sequence alterations, in particular small deletions, may be detected as changes in the migration pattern of DNA heteroduplexes in non-denaturing gel electrophoresis such as heteroduplex electrophoresis. See, e.g., Nagamine et al., Am. J. Hum. Genet., 45, 337–339 (1989). Sequence changes at specific locations may also be revealed by nuclease protection assays, such as RNase and S1 protection or the chemical cleavage method as disclosed by Cotton et al. in Proc. Natl. Acad. Sci. USA, 85, 4397–4401 (1985).

Thus, the detection of a specific DNA sequence may be achieved by methods such as hybridization (e.g., heteroduplex electroporation, see, White et al., Genomics, 12, 301–306 (1992), RNAse protection (e.g., Myers et al., Science, 230, 1242 (1985)) chemical cleavage (e.g., Cotton et al., Proc. Natl. Acad. Sci. USA, 85, 4397–4401 (1985)), direct DNA sequencing, or the use of restriction enzymes (e.g., restriction fragment length polymorphisms (RFLP) in which variations in the number and size of restriction fragments can indicate insertions, deletions, presence of nucleotide repeats and any other mutation which creates or destroys an endonuclease restriction sequence). Southen blotting of genomic DNA may also be used to identify large (i.e., greater than 100 base pair) deletions and insertions.

In addition to conventional gel electrophoresis and DNA sequencing, mutations such as microdeletions, aneuploidies, translocations, inversions, can also be detected by in situ analysis. See, e.g., Keller et al., DNA Probes, 2nd Ed., Stockton Press, New York, N.Y., USA (1993). That is, DNA or RNA sequences in cells can be analyzed for mutations without isolation and/or immobilization onto a membrane. Fluorescence in situ hybridization (FISH) is presently the most commonly applied method and numerous reviews of FISH have appeared. See, e.g., Trachuck et al., Science, 250, 559–562 (1990), and Trask et al., Trends, Genet., 7, 149–154 (1991). Hence, by using nucleic acids based on the structure of the PSP1 or D87258 genes, one can develop diagnostic tests for genetic mutations.

In addition, some diseases are a result of, or are characterized by, changes in gene expression which can be detected by changes in the mRNA. Alternatively, the PSP1 or D87258 gene can be used as a reference to identify individuals expressing an increased or decreased level of PSP1 or D87258 mRNA, e.g., by Northern blotting or in situ hybridization.

Defining appropriate hybridization conditions is within the skill of the art. See, e.g., "Current Protocols in Mol. Biol." Vol. I & II, Wiley Interscience. Ausbel et al. (eds.) (1992). Probing technology is well known in the art and it is appreciated that the size of the probes can vary widely but it is preferred that the probe be at least 15 nucleotides in length. It is also appreciated that such probes can be and are preferably labeled with an analytically detectable reagent to facilitate identification of the probe. Useful reagents include but are not limited to radioisotopes, fluorescent dyes or enzymes capable of catalyzing the formation of a detectable product. As a general rule, the more stringent the hybridization conditions the more closely related genes will be that are recovered.

The putative role of PSP1 or D87258 in presenilin biochemistry establishes yet another aspect of the invention which is gene therapy. "Gene therapy" means gene supplementation where an additional reference copy of a gene of interest is inserted into a patient's cells. As a result, the protein encoded by the reference gene corrects the defect and permits the cells to function normally, thus alleviating disease symptoms. The reference copy would be a wild-type form of the PSP1 or D87258 gene or a gene encoding a protein or peptide which modulates the activity of the endogenous PSP1 or D87258.

Gene therapy of the present invention can occur in vivo or ex vivo. Ex vivo gene therapy requires the isolation and purification of patient cells, the introduction of a therapeutic gene and introduction of the genetically altered cells back into the patient. A replication-deficient virus such as a modified retrovirus can be used to introduce the therapeutic PSP1 or D87258 gene into such cells. For example, mouse Moloney leukemia virus (MMLV) is a well-known vector in clinical gene therapy trials. See, e.g., Boris-Lauerie et al., Curr. Opin. Genet. Dev., 3, 102–109 (1993).

In contrast, in vivo gene therapy does not require isolation and purification of a patient's cells. The therapeutic gene is typically "packaged" for administration to a patient such as in liposomes or in a replication-deficient virus such as adenovirus as described by Berkner, K. L., in Curr. Top. Microbiol. Immunol., 158, 39–66 (1992) or adeno-associated virus (AAV) vectors as described by Muzyczka, N., in Curr. Top. Microbiol. Immunol., 158, 97–129 (1992) and U.S. Pat. No. 5,252,479. Another approach is administration of "naked DNA" in which the therapeutic gene is directly injected into the bloodstream or muscle tissue. Another approach is administration of "naked DNA" in which the therapeutic gene is introduced into the target tissue by microparticle bombardment using gold particles coated with the DNA.

Cell types useful for gene therapy of the present invention include lymphocytes, hepatocytes, myoblasts, fibroblasts, any cell of the eye such as retinal cells, epithelial and endothelial cells. Preferably the cells are T lymphocytes drawn from the patient to be treated, hepatocytes, any cell of the eye or respiratory or pulmonary epithelial cells. Transfection of pulmonary epithelial cells can occur via inhalation of a neubulized preparation of DNA vectors in liposomes, DNA-protein complexes or replication-deficient adenoviruses. See, e.g., U.S. Pat. No. 5,240,846.

Another aspect of the invention is transgenic, non-human mammals capable of expressing the polynucleotides of the invention or D87258 in any cell. Transgenic, non-human animals may be obtained by transfecting appropriate fertilized eggs or embryos of a host with the polynucleotides of the invention, with D87258 or with mutant forms found in human diseases. See, e.g., U.S. Pat. Nos. 4,736,866; 5,175,385; 5,175,384 and 5,175,386. The resultant transgenic animal may be used as a model for the study of PSP1 or D87258 gene function. Particularly useful transgenic animals are those which display a detectable phenotype associated with the expression of the PSP1 or D87258 protein. Drug development candidates may then be screened for their ability to reverse or exacerbate the relevant phenotype.

The present invention will now be described with reference to the following specific, non-limiting examples.

EXAMPLE 1

Identification of the PS-1 Binding Partner PSP1

A portion of PS-1 cDNA (GenBank Accession No. L42110) (SEQ ID NO: 9) encoding residues 269–413 of the PS-1 amino acid sequence (SEQ ID NO: 10) was PCR amplified with the oligonucleotide primers 5'-CGGAATTCCGTATGCTGGTTGAAACA-3' (SEQ ID NO: 11) and 5'-CGGGATCCTCAGGCTACGAAACAGGCTAT-3' (SEQ ID NO: 12). The product was digested with EcoRI and BamHI and cloned into pEG202 (Golemis et al., in Current Protocols in Molecular Biology, John Wiley & Sons, New York (1994)). The resulting plasmid, pCC352, encoded a fusion protein in which the DNA binding protein, LexA, was fused in-frame to amino acids 269–413 of PS-1. The parent vector, pEG202, was a yeast expression vector which uses the alcohol dehydrogenase (ADH1) promoter to express the LexA fusion proteins and HIS3 as the selectable marker. Sequence analysis using an automated DNA sequencer (Applied Biosystems, Inc.) confirmed that the amplified region had the correct sequence and was fused in-frame to LexA.

All procedures, plasmids and strains used in the two-hybrid screen have been described in detail by Golemis et al., supra. Yeast strain EGY48 (MATa, trp1, his3, ura3, 6ops-LEU2) was cotransformed with the plasmids pCC352 and pSH18-34. Transformants were selected using complete minimal media lacking uracil and histidine. The plasmid pSH18-34 is a yeast expression vector in which eight LexA operator sites are located upstream of a minimal GAL1 promoter which drives the expression of the LacZ gene and URA3 as a selectable marker. Synthesis of the full length LexA-PS-1 fusion was confirmed by Western blot analysis of yeast extracts using polyclonal antisera directed against LexA. It was confirmed that the LexA-PS-1 fusion alone was unable to activate neither the LEU2 nor LacZ reporter strains. In addition, the ability of the LexA-PS-1 fusion to enter the nucleus and bind DNA was confirmed using a repression assay.

A strain containing the LexA-PS-1 fusion and pSH18-34 (CCY321) was transformed with a human fetal brain cDNA library (Clontech) in plasmid pJG4-5 using a library scale transformation protocol. This library plasmid contains the TRP1 selectable marker and allows the expression of cDNAs as fusions (AD fusions) to a cassette containing the SV40 nuclear localization sequence, the acid blob B42, and the hemagglutinin epitope tag. See Gyuris et al., Cell 75, 791–803 (1993). Expression of this fusion is under control of the galactose inducible promoter GAL1. Transformation reactions were plated onto complete minimal media lacking uracil, histidine and tryptophan. Approximately 4.5×10$^6$ individual transformants were obtained, pooled and frozen. To ensure that each primary colony was replated during the selection procedure, 2×10$^7$ viable cells (approximately 3 times the number of individual transformants) were plated onto minimal media lacking uracil, histidine, tryptophan and leucine with galactose/raffinose as the carbon source to induce expression of AD fusions. Colonies arising after 3 and 4 days of growth at 30° C. were picked to complete minimal media lacking uracil, histidine and tryptophan. Colonies containing potential interacting fusion proteins were then tested for galactose dependence and LacZ expression. Those isolates which activated both the LEU2 and LacZ reporters in a galactose dependent fashion were considered positive and pursued further. Plasmids were isolated from yeast, used to transform *E. coli* strain KC8, and AD fusion plasmids selected by growth on minimal *E. coli* media lacking tryptophan. Each AD fusion plasmid containing a potential interacting fusion was used to transform CCY321. Several transformants were subjected to screening for galactose dependent LEU2 and LacZ activation. To ensure that the interaction was specific, the ability of each AD fusion plasmid to interact with 22 nonrelated LexA fusion proteins was tested. AD fusion plasmids which passed this second round of screening and interacted specifically with the LexA-PS-1 fusion were identified.

EXAMPLE 2

PSP1 cDNA Cloning and Sequence Analysis

The AD fusion plasmids were subjected to restriction digest analysis and sequencing as indicated above. Sequence analysis of one of the interacting fusion protein cDNAs revealed a 519 nucleotide open reading frame (SEQ ID NO: 1) encoding a 173 amino acid (SEQ ID NO: 2) protein starting with an GGA at position 2 and terminating with a TGA at position 523 of SEQ ID NO: 1. GenBank searches using the BLASTX and BLASTN algorithms with the cDNA sequence or with the deduced amino acid sequence indicated homology to a portion of the E. coli serine protease htrA described by Lipinska et al., supra, (SEQ ID NOs: 13 and 14). This novel cDNA was designated PSP1.

To obtain a greater portion of the cDNA, the oligonucleotide, 5'-CTGGATGGGGAGGTGATTGGAGTG-3' (SEQ ID NO: 15) representing bp 83–106 of SEQ ID NO: 1, was used to screen a Superscript human brain cDNA library (Gibco BRL) using the Genetrapper cDNA positive selection system (Gibco BRL). Colonies were screened using whole cell PCR or standard hybridization conditions as described by Innis et al., *PCR Protocols: A Guide to Methods and Applications*, Academic Press, San Diego, CA (1990) and Sambrook et al., *Molecular Cloning: A Laboratory Manual*, 2nd ed., Cold Spring Harbor Press, Cold Spring Harbor, N.Y. (1989). Those isolates which contained PSP1 were subjected to restriction digest analysis and sequencing. The longest clones, SEQ ID NO:

3 and SEQ ID NO: 5 were sequenced in their entirety. Sequence analysis of SEQ ID NO: 3 revealed a 969 nucleotide open reading frame encoding a 323 amino acid (SEQ ID NO: 4) protein starting with a CCC at position 1 and terminating with a TGA at position 972 of SEQ ID NO: 3. Sequence analysis of SEQ ID NO: 5 revealed a 1500 nucleotide open reading frame encoding a 423 amino acid (SEQ ID NO: 6) protein starting with an CTT at position 1 and terminating with a TGA at position 1272 of SEQ ID NO: 5.

A second round of screening was performed using the oligonucleotide, 51-GTCTCTGGGCCCCGGTTGTCTGTTG-3' (SEQ ID NO: 16) representing bp 5-28 of SEQ ID NO: 5; the library and screening protocol remained unchanged. In the second round of screening, the isolate designated SEQ ID NO: 7 contained the longest cDNA clone. Sequence analysis of SEQ ID NO: 7 revealed a 1374 nucleotide open reading frame encoding a 458 amino acid (SEQ ID NO: 8) protein starting with an ATG at position 251 and terminating with a TGA at position 1627 of SEQ ID NO: 7. However, SEQ ID NO: 7 does not have a stop codon upstream from the potential initiation codon. To confirm that the predicted start codon is authentic, the 5' nucleotide sequence was extended with 5' RACE using "Marathon Ready" human brain cDNA (Clontech) and a nested set of primers. A SEQ ID NO: 7 specific primer 5'-CCAACAGACAACCGGGCCCAGAGACT-3' (SEQ ID NO: 20) and a 5' anchor primer-1 (Clontech) was used in the first PCR amplification and a SEQ ID NO: 7 specific primer 5'-TGCCTCCTCGCCCGCCCTACTCAGA-3' (SEQ ID NO: 21) and 5' anchor primer-2 (Clontech) was used in the second PCR amplification. PCR products were T/A cloned into pCR2.1 (Invitrogen). Eighteen isolates with staggered 5' ends were analyzed and a 5' consensus sequence of 587 nucleotides was generated (SEQ ID NO: 22). Alignment of SEQ ID NO: 22 and SEQ ID NO:7 to generate a consensus sequence (SEQ ID NO: 23) indicates that at nucleotide position 225 there is an in frame stop codon and the first methionine corresponds to that predicted in SEQ ID NO: 7. This gene is designated PSP1-2.

Consensus full length sequences for the genes designated PSP1-1 (SEQ ID NOs: 24 and 25), PSP1-3 (SEQ ID NOs: 26 and 27) and PSP1-4 (SEQ ID NOs: 28 and 29) were generated from alignment of the 5' consensus sequence (SEQ ID NO: 22), other partial PSP1 clones, and with SEQ ID NOs: 7, 3 and 5, respectively.

Alignment of the deduced amino acid sequence of PSP1-1 (SEQ ID NO: 25) to E. coli htrA (SEQ ID NO: 14) was accomplished using the BESTFIT algorithm (University of Wisconsin Genetics Computer Group). An approximate similarity of 55% and an identity of 33.5% at the amino acid level was observed and is shown in FIG. 1 (top, PSP1-1; bottom, E. coli htrA). The critical histidine and serine motif GXSXG conserved in all serine proteases is present in PSP1-1 at amino acid positions 198 and 304–308, respectively, and are indicated in bold. Amino acid numbers are indicated at the left and right of the sequence alignment.

Nucleotide sequence comparison of PSP1-2, PSP1-1, PSP1-3 and PSP1-4 using the PILEUP and PRETTY algorithms (University of Wisconsin Genetics Computer Group) with gap creation and extension penalties of 5.0 and 0.3, respectively, is shown in FIG. 2. The alignment results indicate that at nucleotide position 1541 of the alignment, PSP1-2 and PSP1-1 contain a 225 bp deletion and PSP1-4 contains a 195 bp deletion. Within the same alignment at nucleotide position 1942, PSP1-4 lacks 96 bp that are present in PSP1-2, PSP1-1 and PSP1-3. At the junction of each deletion site there is a splice site consensus sequence AGG or TGG (indicated in bold), suggesting that these alternate forms are due to alternative splicing. See Mount, S. in *Nucl. Acids Res* 10, 458–472 (1982). The apparent splicing event at position 1541 results in the removal of a stop codon (underlined in FIG. 2) that is present in PSP1-3. In addition, PSP1-2 and PSP1-1 contain a single nucleotide difference at position 672 of the alignment. PSP1-2 contains a T at this position producing the codon TGC which codes for a cysteine while PSP1-1 contains a C at the same position producing the codon CGC which codes for a cysteine.

Nucleotide sequence comparison of PSP1-1 (SEQ ID NO: 24) to the putative human serine protease of Ohno et al., supra, (SEQ ID NO: 17) indicated a 49% identity using the GAP algorithm and 65% using the BESTFIT algorithm (data not shown). Alignment of the deduced amino acid sequence of PSP1-1 (SEQ ID NO: 25) to the D87258 protease of Ohno et al., supra, (SEQ ID NO: 18) was accomplished using the BESTFIT algorithm and is shown in FIG. 3 (top, PSP1-1; bottom, Ohno et al. D87258 protease). An approximate identity of 46% at the amino acid level was observed.

EXAMPLE 3

Tissue Distribution of PSP1

Northern analysis was carried out to determine the distribution of PSP1 mRNA in human tissues. A 30-base oligonucleotide probe directed against the PSP1 sequence was used (5'-ATGCTGAACATCGGGAAAGCTTGGTTCTCG-3') (SEQ ID NO: 19). This probe was 3'-end labelled with [$^{32}$P]-dATP. Northern blots containing mRNA from multiple human tissues (Clontech #7750-1, #7760-1, and #7755-1) were hybridized with this probe under stringent conditions. A major band of approximately 1.9kb was detected in all regions investigated: heart, brain, lung, placenta, liver, skeletal muscle, kidney, pancreas, amygdala, caudate nucleus, corpus callosum, hippocampus, substantia nigra, subthalamic nucleus, thalamus, cerebellum, cerebral cortex, medulla, spinal cord, occipital pole, frontal lobe, temporal pole, and putamen. PSP1 mRNA was also detected in Alzheimer's disease brain.

EXAMPLE 4

Detecting the PSP1 Polymorphisms

PSP1 oligonucleotides 1AFC, 1AFT and 1AR were designed for detecting the polymorphism at nucleotide 672 (cytidine to thymine) causing the Arg to Cys amino acid change. The Allele Specific Oligonucleotides (ASO) 1AFC and 1AFT are identical apart from their 3' end bases and provide the specificity for screening for the polymorphism.

| | |
|---|---|
| 1AFC: CAT CCG GCA TTG TTA GCT CTG C 22 mer | (SEQ ID NO:32) |
| 1AFT: CAT CCG GCA TTG TTA GCT CTG T 22 mer | (SEQ ID NO:33) |
| 1AR: CAA TAG CTG CAT CAG TTT GAA TG 23 mer | (SEQ ID NO:34) |

Pairs of oligonucleotides (1AFC+1AR, or 1AFT+1AR) were used in a PCR under the following conditions: 94° C. for 40 seconds, 60° C. for 30 seconds, for 35 cycles in a reaction containing 1 U KlenTaq1 (GenPak Ltd.), 50 mM Tris-Cl pH 9.1, 16 mM ammonium sulphate, 3.5 mM MgCl$_2$, 150 ug ml$^{-1}$ BSA and 25 ng of human genomic DNA of unknown source. Each pair of oligonucleotides was tested against 12 random samples of genomic DNA and the products electrophoresed on a 4% agarose (Gibco-BRL) gel. The expected product of 95 base pairs was seen for both ASOs in 8 of the 12 DNAs indicating that these individuals are heterozygous for this polymorphism. Two of the DNAs amplified with only the 1AFC oligonucleotide and are thus homozygous for the allele with the cytidine at this position. Two of the DNAs amplified with only the 1AFT oligonucleotide and are thus homozygous for the allele with the thymine at this position.

PSP1 oligonucleotides 1BFC, 1BFT and 1BR were designed for detecting the polymorphism at nucleotide 1435 (cytidine to thymine) causing the Ala to Val amino acid change.

| | |
|---|---|
| 1BFC: TGG CGG GCT TTG GGG GGC ATT C 22 mer | (SEQ ID NO:35) |
| 1BFT: TGG CGG GCT TTG GGG GGC ATT T 22 mer | (SEQ ID NO:36) |
| 1BR: GAC GTC AGC AGG GCC CGG AGG TC 23 mer | (SEQ ID NO:37) |

Pairs of oligonucleotides (1BFC+1BR, or 1BFT+1BR) were used in a PCR under the following conditions: 94° C. for 40 seconds, 67° C. for 30 seconds, for 35 cycles in a reaction containing 1 U KlenTaq1 (GenPak Ltd.), 50 mM Tris-Cl pH 9.1, 16 mM ammonium sulphate, 3.5 mM MgCl$_2$, 150 ug ml$^{-1}$ BSA and 25 ng of human genomic DNA of unknown source. Each pair of oligonucleotides was tested against 12 random samples of genomic DNA and the products electrophoresed on a 4% agarose (Gibco-BRL) gel. The expected product of 75 base pairs was seen using the 1BFT ASO in 9 of the 12 samples indicating that the other 3 individuals have a different allele at this position.

EXAMPLE 5

Detecting the D87258 Polymorphism

Oligonucleotides 2AFG, 2AFT and 2AR were designed for detecting the polymorphism at nucleotide 1325 (guanine to thymine) causing the Gly to Val amino acid change.

| | |
|---|---|
| 2AFG: GAT ACC CCA GCA GAA GCT GG 20 mer | (SEQ ID NO:38) |
| 2AFT: GAT ACC CCA GCA GAA GCT GT 20 mer | (SEQ ID NO:39) |
| 2AR: GCT GAC ATC ATT GGC GGA GAC 21 mer | (SEQ ID NO:40) |

Pairs of oligonucleotides (2AFG+2AR, or 2AFT+2AR) were used in a PCR under the following conditions: 94° C. for 40 seconds, 62° C. for 30 seconds, for 35 cycles in a reaction containing 1 U KlenTaq1 (GenPak Ltd.), 50 mM Tris-Cl pH 9.1, 16 mM ammonium sulphate, 3.5 mM MgCl$_2$, 150 ug ml$^{-1}$ BSA and 25 ng of human genomic DNA of unknown source. Each pair of oligonucleotides was tested against 12 random samples of genomic DNA and the products electrophoresed on a 4% agarose (Gibco-BRL) gel. The 2AFT ASO generated a band of approximately 1000 bp. The predicted band was 90 bp. Presumably, the presence of the larger bands was due to the presence of an intron in the region flanked by oligonucletides 2AR and 2AFT. Bands were observed in all of the samples amplified with 2AFT indicating that the allele containing the thymine is present in all 12 individuals.

The present invention may be embodied in other specific forms without departing from the spirit or essential attributes thereof, and, accordingly, reference should be made to the appended claims, rather than to the foregoing specification, as indicating the scope of the invention.

What is claimed is:

1. An isolated polynucleotide encoding a biologically active PSP1 polypeptide.

2. An isolated polynucleotide selected from the group consisting of:
   (a) a polynucleotide encoding PSP1-1 having the nucleotide sequence as set forth in SEQ ID NO: 24 from nucleotide 603 to 1979;
   (b) a polynucleotide encoding PSP1-2 having the nucleotide sequence as set forth in SEQ ID NO: 23 from nucleotide 603 to 1979;
   (c) a polynucleotide encoding PSP1-3 having the nucleotide sequence as set forth in SEQ ID NO: 26 from nucleotide 603 to 1736; and
   (d) a polynucleotide encoding PSP1-4 having the nucleotide sequence as set forth in SEQ ID NO: 28 from nucleotide 603 to 1913.

3. The isolated polynucleotide of claim 2 wherein nucleotides 672 and 1435 are independently selected from C and T.

4. An isolated polynucleotide having the nucleotide sequence as set forth in SEQ ID NOs: 23, 24, 26, 28 or 30.

5. An isolated human polynucleotide selected from the group consisting of:
   (a) a polynucleotide capable of hybridizing under moderately stringent conditions to SEQ ID NOs: 23, 24, 26 or 28;
   (b) a polynucleotide degenerate to SEQ ID NOs: 23, 24, 26 or 28; and
   (c) a polynucleotide degenerate to the polynucleotide capable of hybridizing under moderately stringent conditions to SEQ ID NOs: 23, 24, 26 or 28.

6. The polynucleotide of claim 1 which is DNA or RNA.

7. A vector comprising the DNA of claim 6.

8. A recombinant host cell comprising the vector of claim 7.

9. A method for preparing essentially pure PSP1 protein comprising culturing the recombinant host cell of claim 8 under conditions promoting expression of the protein and recovering the expressed protein.

10. PSP1 produced by the process of claim 9.

11. An isolated functional polypeptide encoded by the polynucleotide of claim 1.

12. The functional polypeptide of claim 1 selected from the group consisting of:
 (a) PSP1-1 having the amino acid sequence set forth in SEQ ID NO: 25 or 31;
 (b) PSP1-2 having the amino acid sequence set forth in SEQ ID NO: 8;
 (c) PSP1-3 having the amino acid sequence set forth in SEQ ID NO: 27; and
 (d) PSP1-4 having the amino acid sequence set forth in SEQ ID NO: 29.

13. A method for preparing essentially pure D87257 (1325T) protein comprising culturing a recombinant host cell comprising an isolated polynucleotide encoding D87257 (1325T) protein under conditions promoting expression of the protein and recovering the expressed protein.

14. D87257 (1325T) produced by the process of claim 13.

* * * * *